US012784478B2

(12) United States Patent
Beaini et al.

(10) Patent No.: US 12,784,478 B2
(45) Date of Patent: Nov. 3, 2026

(54) UTILIZING CONTRASTIVE MACHINE LEARNING MODELS TO EXTRACT JOINT-SPACE MOLECULAR-PHENOMIC EMBEDDINGS FROM MOLECULAR STRUCTURES OR PHENOMIC IMAGES

(71) Applicant: Recursion Pharmaceuticals, Inc., Salt Lake City, UT (US)

(72) Inventors: Dominique Beaini, Kirkland (CA); Jan Frederik Wenkel, Montreal (CA); Karush Suri, Montreal (CA); Maciej Sypetkowski, Warsaw (PL); Philip Fradkin, Toronto (CA); Puria Azadi Moghadam, Burnaby (CA)

(73) Assignee: Recursion Pharmaceuticals, Inc., Salt Lake City, UT (US)

( * ) Notice: Subject to any disclaimer, the term of this patent is extended or adjusted under 35 U.S.C. 154(b) by 170 days.

(21) Appl. No.: 18/930,066

(22) Filed: Oct. 29, 2024

(65) Prior Publication Data

US 2026/0120486 A1 Apr. 30, 2026

(51) Int. Cl.
*G16B 15/00* (2019.01)
*G06V 10/74* (2022.01)
(Continued)

(52) U.S. Cl.
CPC .......... *G06V 20/698* (2022.01); *G06V 10/761* (2022.01); *G06V 10/7715* (2022.01); *G06V 10/776* (2022.01); *G16B 15/00* (2019.02)

(58) Field of Classification Search
None
See application file for complete search history.

(56) References Cited

U.S. PATENT DOCUMENTS

| | | | |
|---|---|---|---|
| 11,715,551 | B2 | 8/2023 | Victors et al. |
| 2022/0180975 | A1 | 6/2022 | Regev et al. |

(Continued)

FOREIGN PATENT DOCUMENTS

| | | | |
|---|---|---|---|
| WO | 01/88760 | A2 | 11/2001 |
| WO | 2021/183956 | A1 | 9/2021 |

OTHER PUBLICATIONS

A. Dosovitskiy, L. Beyer, A. Kolesnikov, D.Weissenborn, X. Zhai, T. Unterthiner, M. Dehghani, M. Minderer, G. Heigold, S. Gelly, et al. "An image is Worth 16x16 Words: Transformers for Image Recognition at Scale". 21 pages, arXiv preprint arXiv:2010. 11929v1, Oct. 22, 2020.

(Continued)

*Primary Examiner* — Idowu O Osifade
(74) *Attorney, Agent, or Firm* — Keller Preece PLLC

(57) ABSTRACT

The present disclosure relates to systems, non-transitory computer-readable media, and methods for utilizing a contrastive molecular-phenomic embedding model that learns joint latent space embeddings between molecular structures and phenomic images to generate molecular-phenomic embeddings that represent molecular impacts on cellular functions. Indeed, the disclosed systems can utilize phenomic image embeddings generated from a pretrained phenomic image encoder model and corresponding molecular structural embeddings with a contrastive molecular-phenomic embedding model to learn a joint latent space between molecular structures and phenomic images (with an inter-sample similarity aware loss (S2L), explicit and implicit concentration encoding, and under sampling of inactive molecular data). In addition, the disclosed systems can utilize molecular structures and/or phenomic images with the contrastive molecular-phenomic embedding model to generate molecular-phenomic embeddings that enable a variety of molecular inferences (e.g., similar molecule deter- (Continued)

minations, similar phenomic image determinations, phenotypic impact determinations from particular molecules, and/or molecular activity classifications).

20 Claims, 17 Drawing Sheets

(51) Int. Cl.
*G06V 10/77* (2022.01)
*G06V 10/776* (2022.01)
*G06V 20/69* (2022.01)

(56) References Cited

U.S. PATENT DOCUMENTS

2024/0331417 A1 10/2024 Kappel
2024/0398989 A1* 12/2024 Claussnitzer ...... A61K 48/0058

OTHER PUBLICATIONS

A. Fürst, E. Rumetshofer, J. Lehner, V. T. Tran, F. Tang, H. Ramsauer, D. Kreil, M. Kopp, 400 G. Klambauer, A. Bitto, et al. "CLOOB: Modern Hopfield Networks with InfoLOOB Outperform CLIP". Advances in Neural Information Processing Systems, 35:20450-20468, 2022.
A. Radford, J. W. Kim, C. Hallacy, A. Ramesh, G. Goh, S. Agarwal, G. Sastry, A. Askell, p. Mishkin, J. Clark, et al. "Learning Transferable Visual Models from Natural Language Supervision". In International Conference on Machine Learning (PMLR), pp. 8748-8763. PMLR, 2021.
A. Radford, J. Wu, R. Child, D. Luan, D. Amodei, and I. Sutskever. "Language Models are Unsupervised Multitask Learners". 24 pages, 2019.
A. Sanchez-Fernandez, E. Rumetshofer, S. Hochreiter, and G. Klambauer. "CLOOME: Contrastive Learning Unlocks Bioimaging Databases for Queries with Chemical Structures". Nature Communications, 14 pages, 2023.
A. v. d. Oord, Y. Li, and O. Vinyals. "Representation Learning with Contrastive Predictive Coding". 13 pages, arXiv preprint arXiv:1807.03748v1, Jul. 10, 2018.
B. Poole, S. Ozair, A. Van Den Oord, A. Alemi, and G. Tucker. "On Variational Bounds of Mutual Information". In International Conference on Machine Learning (PMLR), pp. 5171-5180, 2019.
C. Bock, P. Datlinger, F. Chardon, M. A. Coelho, M. B. Dong, K. A. Lawson, T. Lu, L. Maroc, T. M. Norman, B. Song, G. Stanley, S. Chen, M. Garnett, W. Li, J. Moffat, L. S. Qi, R. S. Shapiro, J. Shendure, J. S. Weissman, and X. Zhuang. "High-Content Crispr Screening". Nature Reviews Methods Primers, 2(1), 53 pages, Feb. 2022.
C. Feichtenhofer, Y. Li, K. He, et al. "Masked Autoencoders as Spatiotemporal Learners". Advances in Neural Information Processing Systems (NeurIPS), 35:35946-35958, 2022.
C. Knox, M. Wilson, C. M. Klinger, M. Franklin, E. Oler, A. Wilson, A. Pon, J. Cox, N. E. L. Chin, S. A. Strawbridge, et al., "DrugBank 6.0: the DrugBank Knowledgebase for 2024". Nucleic Acids Research, 52(D1):D1265-D1275, Nov. 2023.
C. Schuhmann, R. Beaumont, R. Vencu, C. Gordon, R. Wightman, M. Cherti, T. Coombes, A. Katta, C. Mullis, M. Wortsman, et al. "LAION-5B: An Open Large-Scale Dataset for Training Next Generation Image-Text Models". Advances in Neural Information Processing Systems (NeurIPS), 35:25278-25294, 2022.
C. Soneson, S. Gerster, and M. Delorenzi. "Batch Effect Confounding Leads to Strong Bias in Performance Estimates Obtained by Cross-Validation". PloS one, 9(6):e100335, 13 pages, 2014.
D. Masters, J. Dean, K. Klaser, Z. Li, S. Maddrell-Mander, A. Sanders, H. Helal, D. Beker, A. Fitzgibbon, S. Huang, et al. "GPS++: Reviving the Art of Message Passing for Molecular Property Prediction". 15 pages, arXiv preprint arXiv:2302.02947v2, May 12, 2023.
D. Mendez, A. Gaulton, A. P. Bento, J. Chambers, M. De Veij, E. Félix, M. P. Magariños, J. F. Mosquera, P. Mutowo, M. Nowotka, et al. "ChEMBL: Towards Direct Deposition of Bioassay Data". Nucleic Acids Research, 47(D1):D930-D940, 2019.
D. Rogers and M. Hahn. "Extended-Connectivity Fingerprints". Journal of Chemical Information and Modeling, 50(5):742-754, 2010.
F. Lanusse, L. Parker, S. Golkar, M. Cranmer, A. Bietti, M. Eickenberg, G. Krawezik, M. McCabe, R. Ohana, M. Pettee, B. R.-S. Blancard, T. Tesileanu, K. Cho, and S. Ho. AstroCLIP: Cross-Modal Pre-Training for Astronomical Foundation Models, 15 pages, arXiv preprint arXiv:231003024v1, Oct. 4, 2023.
F. Vincent, A. Nueda, J. Lee, M. Schenone, M. Prunotto, and M. Mercola. "Phenotypic Drug Discovery: Recent Successes, Lessons Learned and New Directions". Nature Reviews Drug Discovery, 21(12):899-914, 2022.
G. Landrum et al. "RDKit: A Software Suite for Cheminformatics, Computational Chemistry, and Predictive Modeling". Greg Landrum, 8(31.10):5281, 2013.
G. Zhou, Z. Gao, Q. Ding, H. Zheng, H. Xu, Z.Wei, L. Zhang, and G. Ke. UNI-MOL: A Universal 3D Molecular Representation Learning Framework. In The Eleventh International Conference on Learning Representations, 31 pages, 2023.
H. Kuwahara and X. Gao. "Analysis of the Effects of Related Fingerprints on Molecular Similarity Using an Eigenvalue Entropy Approach". Journal of Cheminformatics, 13:1-12, 2021.
H. Ramsauer, B. Schäfl, J. Lehner, P. Seidl, M. Widrich, T. Adler, L. Gruber, M. Holzleitner, M. Pavlovic, G. K. Sandve, et al. "Hopfield Networks is All You Need". 95 pages, arXiv preprint arXiv:2008.02217v2, Dec. 22, 2020.
H. S. Parker and J. T. Leek. "The Practical Effect of Batch on Genomic Prediction". Statistical Applications in Genetics and Molecular Biology, 11(3), 2012.
J. Kaplan, S. McCandlish, T. Henighan, T. B. Brown, B. Chess, R. Child, S. Gray, A. Radford, J. Wu, and D. Amodei. "Scaling Laws for Neural Language Models". 30 pages, arXiv preprint 418 arXiv:2001.08361v1, Jan. 23, 2020.
J. Simm, G. Klambauer, A. Arany, M. Steijaert, J. K. Wegner, E. Gustin, V. Chupakhin, Y. T. Chong, J. Vialard, P. Buijnsters, et al. "Repurposing High-Throughput Image Assays Enables Biological Activity Prediction for Drug Discovery". Cell Chemical Biology, 25(5):611-618, 2018.
J.-B. Alayrac, et al. "Flamingo: A Visual Language Model for Few-Shot Learning", In Conference on Neural Information Processing Ssytems (NEURIPS) 21 pages, 2022.
J.-B. Grill, F. Strub, F. Altché, C. Tallec, P. H. Richemond, E. Buchatskaya, C. Doersch, B. A. Pires, Z. D. Guo, M. G. Azar, B. Piot, K. Kavukcuoglu, R. Munos, and M. Valko. "Bootstrap Your Own Latent: A New Approach to Self-Supervised Learning", Conference on Neural Information Processing Systems (NeurIPS), 14 pages, 2020.
J. T. Leek, R. B. Scharpf, H. C. Bravo, D. Simcha, B. Langmead, W. E. Johnson, D. Geman, K. Baggerly, and R. A. Irizarry. "Tackling the Widespread and Critical Impact of Batch Effects in High-Throughput Data". Nature Reviews Genetics, 11(10):733-739, 2010.
K. He, X. Chen, S. Xie, Y. Li, p. Dollár, and R. Girshick. "Masked Autoencoders Are Scalable Vision Learners". In Proceedings of the IEEE/CVF Conference on Computer Vision and Pattern Recognition (CVPR), pp. 16000-16009, 2022.
K. He, H. Fan, Y. Wu, S. Xie, and R. Girshick. "Momentum Contrast for Unsupervised Visual Representation Learning", In Proceedings of the IEEE/CVF Conference on Computer Vision and Pattern Recognition (CVPR), pp. 9729-9738, 2020.
K. Sohn. "Improved Deep Metric Learning with Multi-Class N-Pair Loss Objective". In Proceedings of the 30th International Conference on Neural Information Processing Systems, NIPS'16, p. 1857-1865, Red Hook, NY, USA, 2016. Curran Associates Inc.
M. Boutros, F. Heigwer, and C. Laufer. "Microscopy-Based High-Content Screening". Cell, 363 163(6):1314-1325, 2015.
M. Dehghani, J. Djolonga, B. Mustafa, p. Padlewski, J. Heek, J. Gilmer, A. P. Steiner, M. Caron, R. Geirhos, I. Alabdulmohsin, et al.

(56) References Cited

OTHER PUBLICATIONS

"Scaling Vision Transformers to 22 Billion Parameters". In International Conference on Machine Learning (PMLR), pp. 7480-7512. 2023.

M. Hofmarcher, E. Rumetshofer, D.-A. Clevert, S. Hochreiter, and G. Klambauer. "Accurate Prediction of Biological Assays with High-Throughput Microscopy Images and Convolutional Networks". Journal of Chemical Information and Modeling, 59(3):1163-1171, 2019.

M. Sypetkowski, M. Rezanejad, S. Saberian, O. Kraus, J. Urbanik, J. Taylor, B. Mabey, M. Victors, J. Yosinski, A. R. Sereshkeh, et al. Rxrx1: A dataset for evaluating experimental batch correction methods. In Proceedings of the IEEE/CVF Conference on Computer Vision and Pattern Recognition (CVPR), pp. 4284-4293, 2023.

M. Sypetkowski, F. Wenkel, F. Poursafaei, N. Dickson, K. Suri, P. Fradkin, and D. Beaini. "On the Scalability of GNNs for Molecular Graphs". 30 pages, arXiv preprint arXiv:2404.11568v4, Sep. 11, 2024.

M.-A. Bray, S. Singh, H. Han, C. T. Davis, B. Borgeson, C. Hartland, M. Kost-Alimova, 365 S. M. Gustafsdottir, C. C. Gibson, and A. E. Carpenter. "Cell Painting, A High-Content Image Based Assay for Morphological Profiling Using Multiplexed Fluorescent Dyes". Nature protocols, 11(9):1757-1774, 2016.

M. M. Fay, O. Kraus, M. Victors, L. Arumugam, K. Vuggumudi, J. Urbanik, K. Hansen, S. Celik, N. Cernek, G. Jagannathan, et al. "Rxrx3: Phenomics Map of Biology". Biorxiv, pp. 2023-2030, 2023.

O. Kraus, K. Kenyon-Dean, S. Saberian, M. Fallah, P. McLean, J. Leung, V. Sharma, A. Khan, J. Balakrishnan, et al. "Masked Autoencoders for Microscopy are Scalable Learners of Cellular Biology", In Generative AI and Biology Workshop (NeurIPS) 12 pages, 2024.

O. Méndez-Lucio, C. Nicolaou, and B. Earnshaw. "MolE: A Molecular Foundation Model for Drug Discovery", Conference on Neural Information Processing Systems (NeurIPS) 13 pages, 2022.

O. Z. Kraus, B. T. Grys, J. Ba, Y. Chong, B. J. Frey, C. Boone, and B. J. Andrews. "Automated Analysis of High-Content Microscopy Data with Deep Learning". Molecular Systems Biology, 13(4):924, 2017.

R. Balestriero, M. Ibrahim, V. Sobal, A. Morcos, S. Shekhar, T. Goldstein, F. Bordes, A. Bardes, G. Mialon, Y. Tian, A. Schwarzschild, A. G. Wilson, J. Geiping, Q. Garrido, P. Fernandez, A. Bar, H. Pirsiavash, Y. LeCun, and M. Goldblum. "A Cookbook of Self-Supervised Learning", 71 pages, arXiv preprint arXiv:2304.12210v2, Jun. 28, 2023.

R. M. Walmsley and N. Billinton. "How Accurate is in Vitro Prediction of Carcinogenicity?" British Journal of Pharmacology, 162(6):1250-1258, Feb. 2011.

R. S. Bohacek, C. McMartin, and W. C. Guida. "The Art and Practice of Structure-Based Drug Design: A Molecular Modeling Perspective". Medicinal Research Reviews, 16(1):3-50, Jan. 1996.

R. S. Srinivasa, J. Cho, C. Yang, Y. M. Saidutta, C.-H. Lee, Y. Shen, and H. Jin. "CWCL: Cross Modal Transfer with Continuously Weighted Contrastive Loss". Advances in Neural Information Processing Systems (NeurIPS), 36, 18 pages, 2023.

R. Xie, K. Pang, G. D. Bader, and B. Wang. "MAESTER: Masked Autoencoder Guided Segmentation at Pixel Resolution for Accurate, Self-Supervised Subcellular Structure Recognition". In 2023 IEEE/CVF Conference on Computer Vision and Pattern Recognition (CVPR). pp. 3292-3301, Jun. 2023.

S. Albelwi. "Survey on Self-Supervised Learning: Auxiliary Pretext Tasks and Contrastive Learning Methods in Imaging". Entropy, 24(4):551, 22 pages, 2022.

S. Cao, P. Xu, and D. A. Clifton. "How to Understand Masked Autoencoders". 15 pages, arXiv preprint arXiv:2202.03670v2, Feb. 9, 2022.

S. Huang, L. Dong, W. Wang, Y. Hao, S. Singhal, S. Ma, T. Lv, L. Cui, O. K. Mohammed, B. Patra, Q. Liu, K. Aggarwal, Z. Chi, J. Bjorck, V. Chaudhary, S. Som, X. Song, and F. Wei. "Language Is Not All You Need: Aligning Perception with Language Models", 28 pages, arXiv preprint arXiv:2302.14045v2, Mar. 1, 2023.

S. N. Chandrasekaran, J. Ackerman, E. Alix, D. M. Ando, J. Arevalo, M. Bennion, et al. "JUMP Cell Painting dataset: morphological impact of 136,000 chemical and genetic perturbations". bioRxiv, 16 pages, 2023.

S. Zaidi, M. Schaarschmidt, J. Martens, H. Kim, Y. W. Teh, A. Sanchez-Gonzalez, P. Battaglia, R. Pascanu, and J. Godwin. "Pre-Training Via Denoising for Molecular Property Prediction", 24 pages, arXiv preprint arXiv:2206.00133v2, Oct. 25, 2022.

T. Chen, S. Kornblith, K. Swersky, M. Norouzi, and G. E. Hinton. "Big Self-Supervised Models are Strong Semi-Supervised Learners". Advances in Neural Information Processing Systems (NeurIPS), 33:22243-22255, 2020.

X. Zhai, B. Mustafa, A. Kolesnikov, and L. Beyer. "Sigmoid Loss for Language Image Pre-Training". In Proceedings of the IEEE/CVF International Conference on Computer Vision (ICCV), pp. 11975-11986, 2023.

X. Zhai, X. Wang, B. Mustafa, A. Steiner, D. Keysers, A. Kolesnikov, and L. Beyer. "LiT: Zero-Shot Transfer with Locked-Image Text Tuning", Conference on Computer Vision and Pattern Recognition (CVPR), pp. 18123-18133, 2022.

Y. Rong, Y. Bian, T. Xu, W. Xie, Y. Wei, W. Huang, and J. Huang. Self-Supervised Graph Transformer on Large-Scale Molecular Data, Conference on Neural Information Processing Systems (NeurIPS), 13 pages, 2020.

Y. Zhong, H. Tang, J. Chen, J. Peng, and Y.-X. Wang. "Is Self-Supervised Learning More Robust Than Supervised Learning?", 16 pages, arXiv preprint arXiv:2206.05259v1, Jun. 10, 2022.

International Search Report and Written Opinion as received in PCT/US2025/050547 dated Feb. 13, 2026.

* cited by examiner

| Method | Explicit Concentration | Modality | top-1% Unseen Images | top-1% Unseen Images + Unseen Molecules | top-1% Unseen Dataset (0-shot) | top-1% Avg. | top-5% Unseen Images | top-5% Unseen Images + Unseen Molecules | top-5% Unseen Dataset (0-shot) | top-5% Avg. |
|---|---|---|---|---|---|---|---|---|---|---|
| CLIP | ✗ | Ph-1 | **.3373** | **.4228** | **.1514** | .3038 | **.6162** | **.7182** | **.3660** | .5668 |
| Hopfield-CLIP | ✗ | Ph-1 | **.2578** | **.3559** | **.1256** | .2464 | **.5457** | **.6751** | **.3270** | .5159 |
| InfoLOOB | ✗ | Ph-1 | **.3351** | **.4206** | **.1563** | .3040 | **.6128** | **.7204** | **.3730** | .5687 |
| CLOOME | ✗ | Ph-1 | **.3572** | **.4348** | **.1658** | .3193 | **.6330** | **.7259** | **.3918** | .5836 |
| DCL | ✗ | Ph-1 | .6363 | .6177 | .3184 | .5241 | .8638 | .8180 | .5632 | .7483 |
| DCL | sigmoid | Ph-1 | .8858 | .6694 | .4527 | .6693 | **.9600** | .8472 | .6845 | .8305 |
| DCL | logarithm | Ph-1 | .8934 | .6952 | .4511 | .6799 | .9581 | **.8788** | **.6889** | **.8419** |
| DCL | one-hot | Ph-1 | **.8901** | **.7002** | **.4601** | **.6834** | .9591 | .8770 | .6873 | .8411 |
| CWCL | ✗ | Ph-1 | .7091 | .6529 | .3556 | .5725 | .9018 | .8368 | .6027 | .7804 |
| CWCL | sigmoid | Ph-1 | .9138 | .6985 | .4810 | .6977 | .9681 | .8643 | .7070 | .8464 |
| CWCL | logarithm | Ph-1 | .9141 | .7248 | .4815 | .7068 | .9651 | .8920 | **.7131** | **.8567** |
| CWCL | one-hot | Ph-1 | **.9128** | **.7261** | **.4850** | **.7079** | **.9665** | **.8927** | .6998 | .8530 |
| SigLip | ✗ | Ph-1 | .7763 | .6401 | .3396 | .5853 | .9361 | .83038 | .5714 | .7792 |
| SigLip | sigmoid | Ph-1 | .9463 | .6931 | .4576 | .6990 | .9816 | .8606 | .6759 | .8393 |
| SigLip | logarithm | Ph-1 | **.9493** | .7256 | .4868 | **.7205** | .9814 | **.8926** | .7015 | **.8586** |
| SigLip | one-hot | Ph-1 | .9489 | **.7210** | **.4859** | .7186 | **.9823** | .8868 | **.7045** | .8578 |
| MolPhenix | ✗ | Ph-1 | .9097 | .6759 | .4181 | .6679 | .9768 | .8539 | .6436 | .8247 |
| MolPhenix | sigmoid | Ph-1 | .9423 | .7155 | .4573 | .7050 | .9808 | .8775 | .6778 | .8453 |
| MolPhenix | logarithm | Ph-1 | .9426 | .7451 | .4727 | .7201 | .9808 | .8964 | .6952 | .8574 |
| MolPhenix | one-hot | Ph-1 | **.9430** | **.7490** | **.4850** | **.7256** | **.9816** | **.8984** | **.7040** | **.8613** |
| MolPhenix | ✗ | Ph-1 + Mol-1 | .9105 | .6710 | .4501 | .6772 | .9755 | .8527 | .7098 | .8460 |
| MolPhenix | sigmoid | Ph-1 + Mol-1 | .9395 | .7034 | .5252 | .7227 | .9811 | .8729 | .7630 | .8723 |
| MolPhenix | logarithm | Ph-1 + Mol-1 | .9413 | .7505 | .5473 | .7463 | .9811 | **.9065** | **.7878** | **.8924** |
| MolPhenix | one-hot | Ph-1 + Mol-1 | **.9430** | **.7514** | **.5577** | **.7507** | **.9830** | .9043 | .7821 | .8898 |

*Fig. 9B*

UTILIZING CONTRASTIVE MACHINE LEARNING MODELS TO EXTRACT JOINT-SPACE MOLECULAR-PHENOMIC EMBEDDINGS FROM MOLECULAR STRUCTURES OR PHENOMIC IMAGES

BACKGROUND

Recent years have seen significant improvements in hardware and software platforms for utilizing computing devices to extract and analyze digital signals corresponding to biological relationships. For example, existing systems often utilize computer-based models to extract latent features from molecular structures or images portraying cells. In addition, some existing systems conduct analyses of the features extracted from the cell images or the molecular structures to determine biological (or chemical) relationships between the images and the molecular structures. Although existing systems can utilize computer-based models to extract and analyze digital signals for images portraying cells and molecular structures, these conventional systems often have a number of technical deficiencies with regard to computational inefficiencies, extraction inaccuracies, and inflexibilities in utilizing machine learning to align features (or digital signals) from molecular structures and microscopy images.

SUMMARY

Embodiments of the present disclosure provide benefits and/or solve one or more of the foregoing or other problems in the art with systems, non-transitory computer-readable media, and computer-implemented methods for utilizing a contrastive molecular-phenomic embedding model that learns joint latent space embeddings between molecular structures and phenomic images to generate molecular-phenomic embeddings that represent molecular impacts on cellular functions. In particular, the disclosed systems can utilize phenomic image embeddings generated from a pre-trained phenomic image embedding model and corresponding molecular structural embeddings with a contrastive molecular-phenomic embedding model to learn a joint latent space between molecular structures and phenomic images of cells. Furthermore, the disclosed systems can utilize molecular structures and/or phenomic images with the contrastive molecular-phenomic embedding model to generate molecular-phenomic embeddings that enable a variety of molecular inferences (e.g., similar molecule determinations, similar phenomic image determinations, phenotypic impact determinations from particular molecules, and/or molecular activity classifications).

Additionally, in one or more implementations, the disclosed systems train the contrastive molecular-phenomic embedding model to align relationships between molecular structural embeddings and phenomic image embeddings in the joint molecular-phenomic embeddings. Indeed, in one or more instances, the disclosed systems train the contrastive molecular-phenomic embedding model by under sampling training data corresponding to inactive molecules (determined via the phenomic image embeddings) and/or utilizing an inter-sample similarity aware loss (S2L) for the contrastive loss. Furthermore, in one or more instances, the disclosed systems also explicitly and implicitly utilize (during training and inference) concentration doses with molecule structures with the contrastive molecular-phenomic embedding model to generate informative molecular-phenomic embeddings.

Additional features and advantages of one or more embodiments of the present disclosure are outlined in the description which follows, and in part can be determined from the description, or may be learned by the practice of such example embodiments.

BRIEF DESCRIPTION OF THE DRAWINGS

The detailed description is described with reference to the accompanying drawings in which:

FIGS. 9A, 9B, and 10-12 illustrate experimental results of one or more implementation of a digital molecular-phenomic embedding system in accordance with one or more implementations.

DETAILED DESCRIPTION

This disclosure describes one or more embodiments of a digital molecular-phenomic embedding system that generates joint latent space molecular-phenomic embeddings that align relationships between molecular structures and impacts of the molecular structures on cellular functions (via phenomic images). In one or more implementations, the digital molecular-phenomic embedding system generates phenomic image embeddings from phenomic images (e.g., using a pretrained embedding model) and, subsequently, utilizes a vision encoder of a contrastive molecular-phenomic embedding model to map the phenomic image embeddings into a joint molecular-phenomic feature space. Moreover, the digital molecular-phenomic embedding system can also utilize a molecular encoder (e.g., structural encoder) for the contrastive molecular-phenomic embedding model to generate molecular structural embeddings for the joint molecular-phenomic feature space. Indeed, the digital molecular-phenomic embedding system can train the contrastive molecular-phenomic embedding model to align molecular structural embeddings and phenomic image embeddings in the joint latent space to determine relationships between molecular structures and impacts of the molecular structures on cellular functions (via phenomic images). Moreover, the digital molecular-phenomic embedding system can utilize molecular structures and/or phenomic images with the molecular encoder and/or vision encoder of contrastive molecular-phenomic embedding model to generate molecular-phenomic embeddings in the joint molecular-phenomic feature space that enable a variety of molecular inferences.

Figure 1:
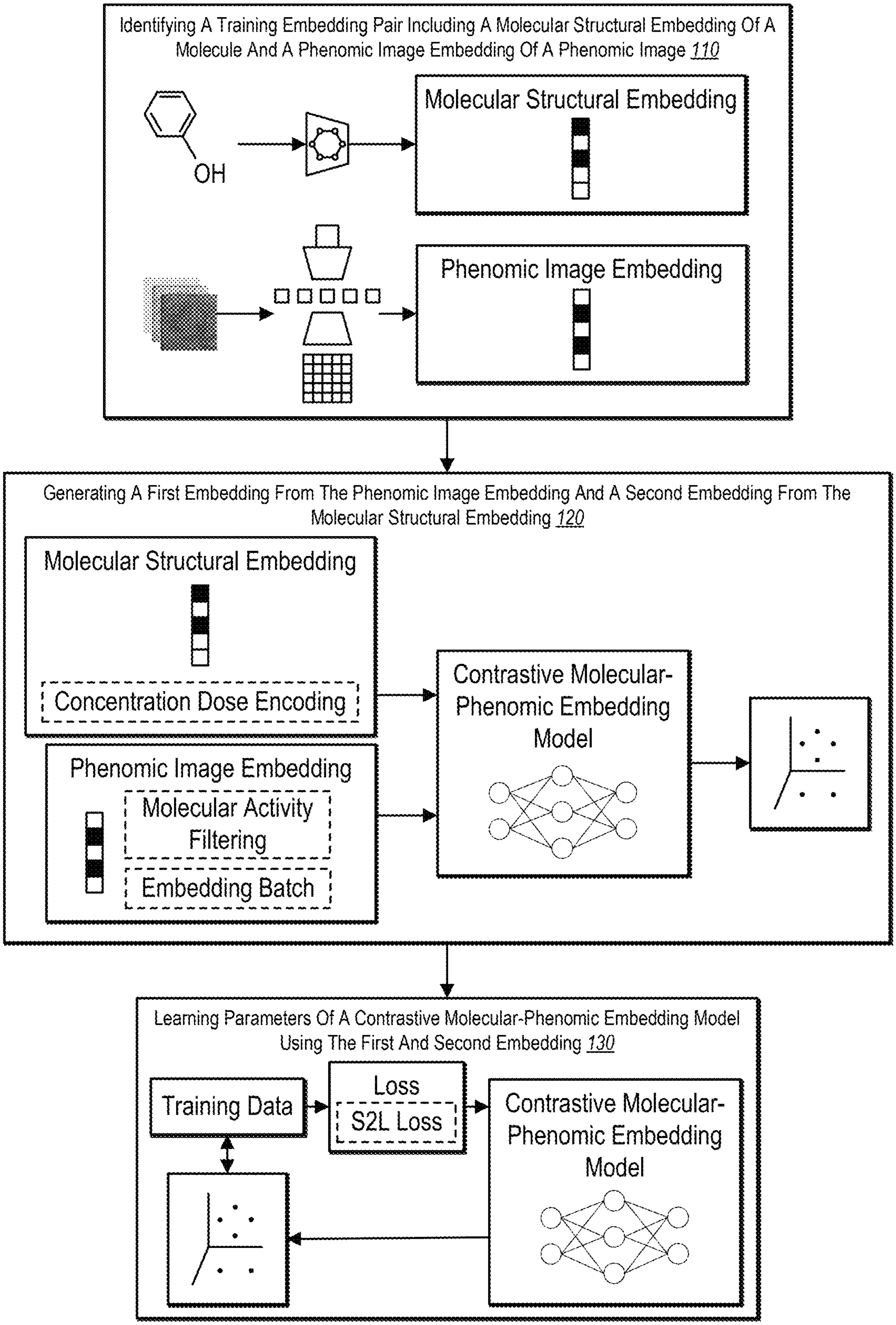
FIG. 1 illustrates an overview of a digital molecular-phenomic embedding system training a contrastive molecular-phenomic embedding model in accordance with one or more implementations.

For example, FIG. 1 illustrates an overview of a digital molecular-phenomic embedding system 106 training a contrastive molecular-phenomic embedding model utilizing phenomic image embeddings from phenomic images (e.g., using a pretrained embedding model) and molecular structural embeddings. For instance, as shown in FIG. 1, the digital molecular-phenomic embedding system 106 identifies a training embedding pair including a molecular structural embedding of a molecule and a phenomic image embedding, generates a first embedding from the phenomic image embedding and a second embedding from the molecular structural embedding, and learns parameters of the contrastive molecular-phenomic embedding generator model using the first and second embedding.

For instance, as shown in an act 110 of FIG. 1, the digital molecular-phenomic embedding system 106 identifies a training embedding pair that includes a molecular structural embedding of a molecule and a phenomic image embedding of a phenomic image. For instance, the digital molecular-phenomic embedding system 106 identifies a pairing of a molecule and a phenomic image portraying a cellular perturbation from the molecule. Moreover, as shown in FIG. 1, the digital molecular-phenomic embedding system 106 can utilize the molecular structure of the molecule to generate a molecular structural embedding (e.g., using a molecular structural embedding model). Furthermore, as shown in FIG. 1, the digital molecular-phenomic embedding system 106 can utilize a pretrained phenomic image encoding model (e.g., a masked autoencoder model) to generate phenomic image embedding from one or more phenomic images portraying a cellular perturbation from the molecule (e.g., to improve retrieval accuracy from a joint latent space).

Moreover, as shown in an act 120 of FIG. 1, the digital molecular-phenomic embedding system 106 generates a first embedding from the phenomic image embedding and a second embedding from the molecular structural embedding (for a joint latent feature space). In particular, the digital molecular-phenomic embedding system 106 can utilize a structural (or molecular) encoder of a contrastive molecular-phenomic embedding model to map molecular structural embeddings, generated from a pre-trained molecular structure model, into a joint molecular-phenomic feature space (as a first embedding). In some cases, the digital molecular-phenomic embedding system 106 also combines the molecular structural embedding with a concentration dose encoding and utilizes the combined concentration structural embedding with the structural encoder of the contrastive molecular-phenomic embedding model to map the combined concentration structural embedding into the joint molecular-phenomic feature space (e.g., to improve granularity for molecule and phenomic image relationships during training).

Furthermore, the digital molecular-phenomic embedding system 106 can utilize a vision encoder of the contrastive molecular-phenomic embedding model to map the phenomic image embeddings into a joint molecular-phenomic feature space (as a first embedding). As shown in FIG. 1, in some cases, the digital molecular-phenomic embedding system 106 performs embedding batching to batch embeddings corresponding to multiple phenomic images corresponding a particular molecule to reduce an introduction of noise in the latent space. Moreover, as shown in FIG. 1, in one or more implementations, the digital molecular-phenomic embedding system 106 performs molecular activity filtering to filter (or under sample) molecules determined as inactive molecules by determining, via a null distribution of phenomic embeddings, that a particular molecule results in a non-distinct phenomic image embedding (to utilize in training data).

Indeed, the digital molecular-phenomic embedding system 106 can map the joint molecular-phenomic feature space embedding for the phenomic image embedding and the joint molecular-phenomic feature space embedding for the molecular structural embedding in a joint latent space. In one or more instances, the digital molecular-phenomic embedding system 106 utilizes the joint latent space from the contrastive molecular-phenomic embedding model to determine relationships between molecules and phenomic images (e.g., to indicate phenotypic effects for molecules). In one or more instances, the digital molecular-phenomic embedding system 106 generates molecular-phenomic embeddings in a joint latent space from molecular structural embeddings and phenomic image embeddings as described in greater detail below (e.g., in reference to FIGS. 3-5).

Furthermore, as illustrated in act 130 of FIG. 1, the digital molecular-phenomic embedding system 106 learns parameters of a contrastive molecular-phenomic embedding model using the first and second embedding (generated as described in the acts 110 and 120). In particular, the digital molecular-phenomic embedding system 106 can modify parameters of the contrastive molecular-phenomic embedding model with an objective to enable the contrastive molecular-phenomic embedding model to map molecular-phenomic embeddings in a joint latent space from molecular structural embeddings and phenomic image embeddings closer in the joint latent space to represent similarities and further apart to represent dissimilarities.

Indeed, the digital molecular-phenomic embedding system 106 can determine a measure of loss from similarity distances between the embeddings in the joint molecular-phenomic feature space and positive (ground truth pairs) and utilize the measure of loss to modify parameters of the contrastive molecular phenomic embedding model (e.g., to improve embedding and retrieval accuracy). In some cases, the digital molecular-phenomic embedding system 106 utilizes an inter-sample similarity aware loss that weighs the measure of contrastive loss based on similarity measurements between the phenomic image embedding and additional phenomic image embeddings (e.g., to emphasize distinct phenomic image embeddings). Moreover, in some implementations, the implicitly utilizes molecule concentration doses in training by utilizing molecular dose concentrations as separate classes while determining a measure of loss for the contrastive molecular-phenomic embedding model. In one or more instances, the digital molecular-phenomic embedding system 106 trains the contrastive molecular phenomic embedding model as described in greater detail below (e.g., in reference to FIGS. 5 and 6).

Figure 2:
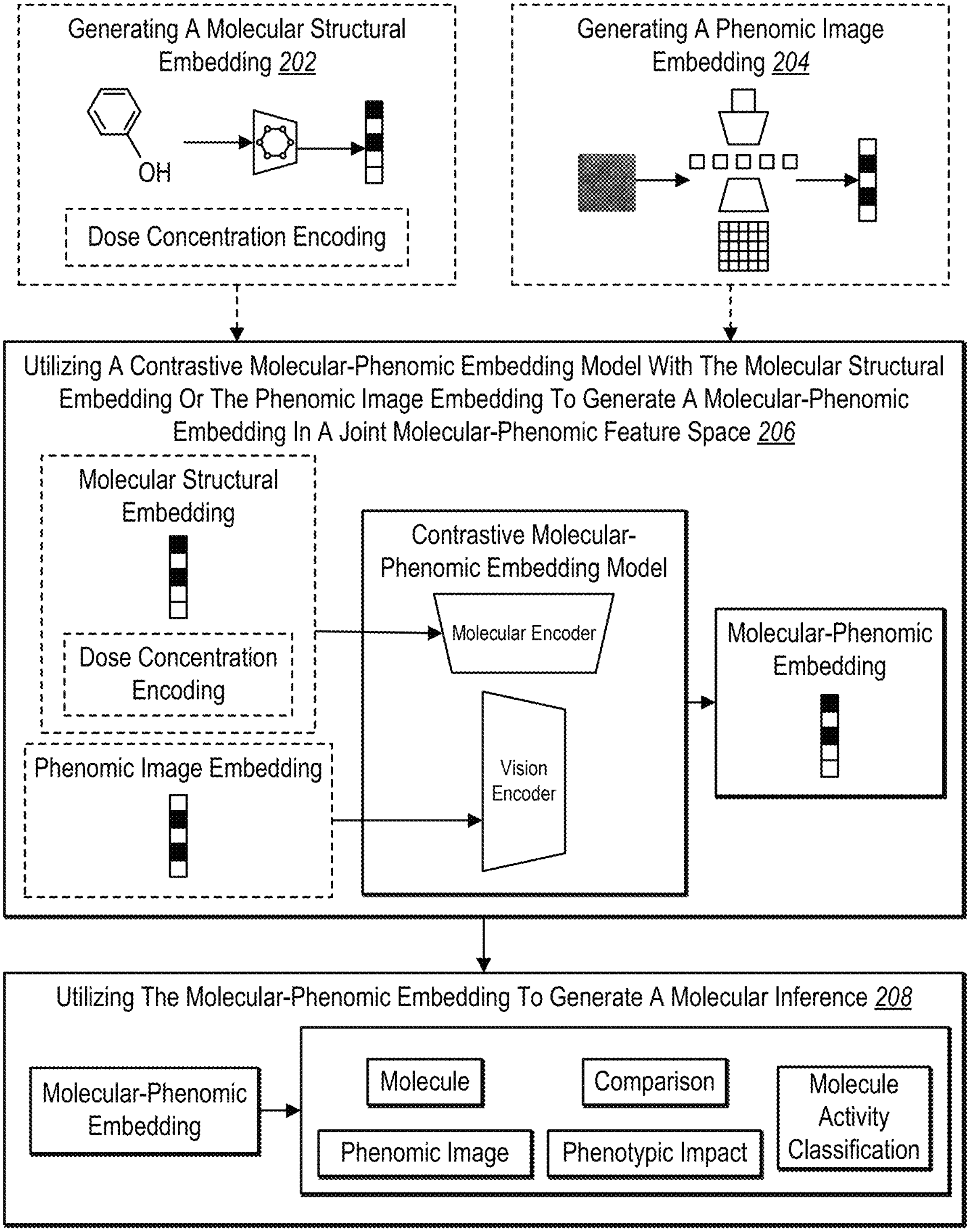
FIG. 2 illustrates an overview of a digital molecular-phenomic embedding system utilizing a contrastive molecular-phenomic embedding model for a variety of downstream tasks in accordance with one or more implementations.

Moreover, the digital molecular-phenomic embedding system 106 can utilize the contrastive molecular-phenomic embedding model to generate molecular-phenomic embeddings (from molecular structures and/or phenomic images) for utilizing in a variety of molecular inferences (e.g., biological and/or chemical inferences). For example, FIG. 2 illustrates an overview of the digital molecular-phenomic embedding system 106 utilizing a contrastive molecular-phenomic embedding model for a variety of downstream tasks. In particular, FIG. 2 illustrates the digital molecular-phenomic embedding system 106 generating a molecular structural embedding and/or a phenomic image embedding, utilizing a contrastive molecular-phenomic embedding model with the molecular structural embedding or the phenomic image embedding to generate a molecular-phenomic embedding in a joint molecular-phenomic feature space, and utilizing the molecular-phenomic embedding to generate a molecular inference.

Indeed, as shown in act 202 of FIG. 2, in some instances, the digital molecular-phenomic embedding system 106 generates a molecular structural embedding from a molecule structure. For example, the digital molecular-phenomic embedding system 106 can utilize a molecular structural embedding model to generate a structural embedding from a molecular structure. Indeed, a molecular structure can include various types of molecules utilized in phenotypic experiments to perturb or impact cellular morphology. For example, a molecular structure can include a chemical molecule (e.g., a drug compound), a genetic molecule, a protein molecule, and/or gene knockout data. As further shown in FIG. 2, in some cases, the molecular structural embedding is combined with a concentration dose encoding to generate a structural embedding that explicitly includes concentration dose information (e.g., a combined concentration structural embedding). Indeed, the digital molecular-phenomic embedding system 106 can generate a molecular structural embedding as described in greater detail below (e.g., in reference to FIGS. 3-5).

In some instances, as shown in act 204 of FIG. 2, the digital molecular-phenomic embedding system 106 generates a phenomic image embedding from a phenomic image. For example, the digital molecular-phenomic embedding system 106 generates phenomic image embedding from a phenomic image portraying a perturbed cell. In one or more implementations, the digital molecular-phenomic embedding system 106 utilizes a pretrained embedding model (e.g., a pretrained masked autoencoder model) that generates a phenomic image embedding (e.g., a phenomic image autoencoder embedding) that represents latent features of a phenomic image. Indeed, the digital molecular-phenomic embedding system 106 can generate a phenomic image embedding as described in greater detail below (e.g., in reference to FIGS. 3-5).

Furthermore, as shown in an act 206 of FIG. 2, the digital molecular-phenomic embedding system 106 (individually) utilizes the molecular structural embedding or the phenomic image embedding with encoders (of a contrastive molecular phenomic embedding model) to generate a molecular-phenomic embedding in the joint molecular-phenomic feature space. In particular, as shown in the act 206, in one or more implementations, the digital molecular-phenomic embedding system 106 utilizes a molecular structural embedding (and a concentration dose encoding) with a molecular encoder (e.g., structural encoder) of the contrastive molecular-phenomic embedding model to generate an embedding compatible within a joint molecular-phenomic feature space (as the molecular-phenomic embedding). In some instances, as shown in the act 206 of FIG. 2, the digital molecular-phenomic embedding system 106 utilizes a phenomic image embedding with a vision encoder of the contrastive molecular-phenomic embedding model to generate an embedding compatible within a joint molecular-phenomic feature space (as the molecular-phenomic embedding). Indeed, the digital molecular-phenomic embedding system 106 can generate a molecular-phenomic embedding from a molecular structural embedding and/or a phenomic image embedding as described in greater detail below (e.g., in reference to FIGS. 3-6).

Moreover, as shown in an act 208 of FIG. 2, the digital molecular-phenomic embedding system 106 utilizes the molecular-phenomic embedding (generated for a molecular structure and/or a phenomic image) for a variety of downstream tasks. For instance, as shown in the act 208, the digital molecular-phenomic embedding system 106 utilizes the molecular-phenomic embedding to generate one or more molecular inferences. Indeed, as shown in the act 208, the digital molecular-phenomic embedding system 106 utilizes the molecular-phenomic embeddings to determine similar molecules (e.g., via a comparison or retrieval), similar phenomic images (e.g., via a comparison or retrieval), comparisons between molecules and molecules and/or phenomic images and phenomic images, phenotypic impacts, and/or molecular activity classifications. For example, the digital molecular-phenomic embedding system 106 utilizes molecular-phenomic embeddings to determine a variety of molecular inferences as described in greater detail below (e.g., in reference to FIGS. 7 and 8).

As mentioned above, although existing systems can utilize computer-based models to extract and analyze digital signals for images portraying cells and molecular structures, these conventional systems often have a number of technical shortcomings with regard to computational inefficiencies, extraction inaccuracies, and inflexibilities in utilizing machine learning to align features (or digital signals) from molecular structures and microscopy images. For instance, some conventional systems utilize multi-modal models to combine samples from two or more domains to learn representations that predict sample properties via contrastive methods. However, many of these existing multi-modal models are inefficient. In particular, conventional systems oftentimes require large datasets of images and molecular structure pairings to train the multi-modal models to a useable state. Indeed, in many cases, conventional systems require a large dataset of training pairs to train a multi-modal model to accurately identify representational similarities between obscure, different features in both molecular structures and microscopy images. In many cases, conventional systems that build and train with large datasets of training pairs (of molecular structures and microscopy images) require an inefficient amount of computational resources and training time.

Despite utilizing extensive (and inefficient) time and computational resources to train, many conventional systems remain deficient in accuracy. For instance, many conventional systems result in low retrieval rates from multi-modal systems utilized for molecular structures and microscopy images. Moreover, many conventional systems suffer inaccurate retrieval as a result of noise from images and molecules that are inactive that do not capture biologically meaningful information. Indeed, such conventional systems often result in models that encode or retrieve embeddings that capture non-biologically meaningful variations that deter accurate outputs.

In addition to being inefficient and inaccurate, conventional systems are often inflexible. For example, oftentimes, conventional systems that utilize multi-modal modeling approaches to identify relationships between molecular structures and microscopy images are limited to one-dimensional comparisons. Indeed, in many cases, conventional systems attempt to identify relationships between molecules and microscopy images but cannot easily identify relationships between variations of the same molecules and microscopy images. In addition, many conventional systems cannot easily discern inactive molecules or inactivity in microscopy images as such effects are difficult to identify directly from a molecule structure or a microscopy image. Accordingly, many conventional systems result in rigid multi-modal models that are unable to consider molecule variations and/or inactivity of molecules or microscopy images.

As suggested by the foregoing, the digital molecular-phenomic embedding system 106 provides a variety of technical advantages relative to conventional systems. Indeed, the digital molecular-phenomic embedding system 106 can efficiently train multi-modal contrastive models to determine relationships between molecular structures and phenomic (or microscopy) images. In particular, unlike many conventional systems that require a significant number of training data pairs, the digital molecular-phenomic embedding system 106 reduces the number of paired training data points to train an accurate multi-modal contrastive model for molecular structures and phenomic images. For instance, by utilizing uni-modal pre-trained models to process the phenomic images (and molecular structures) to generate phenomic image embeddings and molecular structural embeddings that are subsequently used to encode embeddings in a joint feature space, the digital molecular-phenomic embedding system 106 matches zero-shot performance with many conventional systems with an order of magnitude fewer paired training samples. Accordingly, the digital molecular-phenomic embedding system 106 can match or improve accuracy compared to many conventional systems with less training data which improves training time speeds and reduces the utilization of computational resources during training.

In addition to improving efficiency, the digital molecular-phenomic embedding system 106 also improves the accuracy determining relationships between molecular structures and phenomic images through multi-modal contrastive models. In particular, the utilization of uni-modal pre-trained models to process the phenomic images (and molecular structures) to generate phenomic image embeddings and molecular structural embeddings that are subsequently used to encode embeddings in a joint feature space, the digital molecular-phenomic embedding system 106 improves the accuracy (e.g., accurate retrieval rates) from the joint feature space. In particular, in contrast to many conventional systems, the digital molecular-phenomic embedding system 106 generates (or utilizes) phenomic image embeddings and molecular structural embeddings to enable encoding and the comparing of granular data (otherwise not available) in the joint feature space to improve the performance of molecular-phenomic image contrastive learning models.

In addition, the digital molecular-phenomic embedding system 106 also improves accuracy by reducing noise and batching effects from phenomic image and molecular data that is subject to random batch effects that capture non-biologically meaningful variations. In particular, by generating (or utilizing) phenomic image embeddings (from a uni-modal pre-trained model), the digital molecular-phenomic embedding system 106 can control for noise and batch effects. Indeed, in one or more cases, the digital molecular-phenomic embedding system 106 combines phenomic image embeddings from phenomic images corresponding to a particular molecule (e.g., phenomic images resulting from lab experiments or simulations with a particular molecule perturbation) to alleviate noise in the latent space resulting from random perturbations in an experiment (or simulation) process outside of biologically meaningful variations.

Moreover, many conventional systems also struggle to infer a priori whether a molecule has a cellular effect which leads to noisy data with paired phenomic-molecular data having inactive perturbations that do not have a biological effect (or do not perturb cellular morphology). In contrast, to improve accuracy, the digital molecular-phenomic embedding system 106 utilizes a null distribution of the phenomic image embeddings (generated from a uni-modal pre-trained model) to, a priori, identify inactive paired phenomic-molecular data during training to reduce noisy data pairs in training the contrastive molecular-phenomic embedding model. Moreover, in one or more implementations, the digital molecular-phenomic embedding system 106 further utilizes a soft-weighted sigmoid locked loss to address the effects of inactive molecules by leveraging inter-sample similarities of the phenomic embeddings to weight a contrastive loss measure of the contrastive molecular-phenomic embedding model. Indeed, utilizing the above-mentioned approaches, the digital molecular-phenomic embedding system 106 improves embedding and retrieval accuracy of a contrastive molecular-phenomic embedding model.

Indeed, experimental results illustrated with respect to FIGS. 9-12 demonstrate a variety of technical advantages and accuracy improvements provided by one or more implementations of the digital molecular-phenomic embedding system in comparison to other existing systems.

In addition to efficiency and accuracy, the digital molecular-phenomic embedding system 106 also improves the flexibility of phenomic-molecular models. For instance, unlike many conventional systems that are limited to identifying relationships between molecular structures and microscopy images through one-dimensional comparisons, the digital molecular-phenomic embedding system 106 enables inferences (or relationships) between variations of a molecule and phenomic images. In particular, the digital molecular-phenomic embedding system 106 can utilize explicit concentration dose encoding with the molecular structural embedding to train a contrastive molecular phenomic embedding model to be dose aware. Moreover, in addition to explicit concentration dose encoding, while training, the digital molecular-phenomic embedding system 106 also implicitly utilizes concentration doses by utilizing loss measures separately for different doses of a molecule (e.g., treating molecules with different concentration doses as distinct classes in training). Indeed, by conditioning on explicit and implicit representations of dose concentration, the digital molecular-phenomic embedding system 106 improves the flexibility of capturing molecular impacts on cell morphology and improves generalization to previously unseen molecules and concentrations (via the contrastive molecular phenomic embedding model).

Furthermore, the digital molecular-phenomic embedding system 106 can utilize the efficient, accurate, and flexible contrastive molecular phenomic embedding model with phenomic images (or other microscopy representations) and/or molecular structures for a variety of practical applications. In particular, the accurate retrieval of phenomic images and/or molecular structures (with dosage granularity) from the joint feature space of the contrastive molecular phenomic embedding model enables the digital molecular-phenomic embedding system 106 to perform a variety of downstream tasks (e.g., molecular inferences) accurately and efficiently. For instance, the above-mentioned improvements enable the digital molecular-phenomic embedding system 106 to utilize molecular-phenomic embeddings (generated from the contrastive molecular phenomic embedding model) to determine similar molecules (e.g., via a comparison or retrieval), similar phenomic images (e.g., via a comparison or retrieval), comparisons between molecules and molecules and/or phenomic images and phenomic images, phenotypic impacts, and/or molecular activity classifications for a variety of phenomic images and/or molecular structures (with concentration dose awareness).

Figure 3:
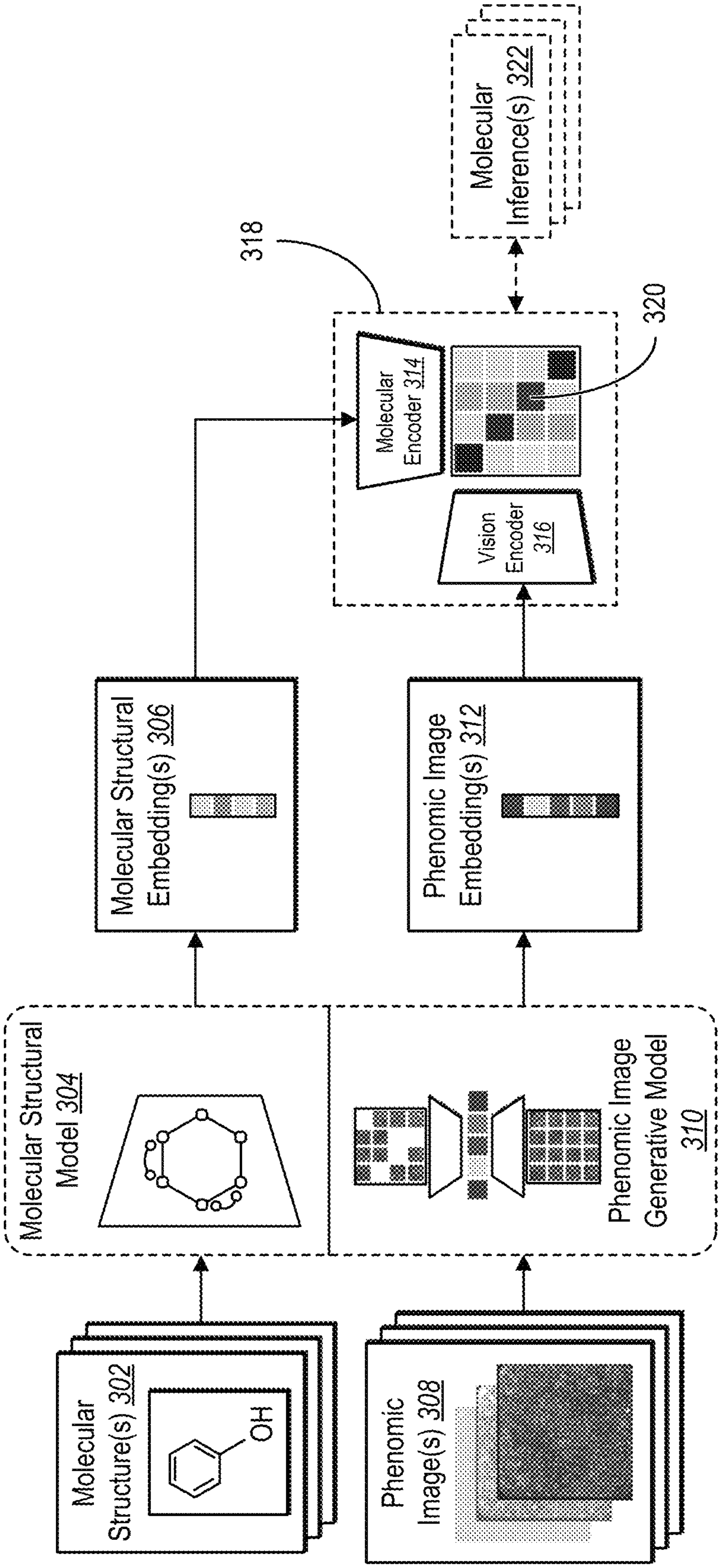
FIG. 3 illustrates an overview of an architecture a digital molecular-phenomic embedding system in accordance with one or more implementations.

As mentioned above, the digital molecular-phenomic embedding system 106 can generate molecular-phenomic embeddings in a joint feature space from molecular structures and/or phenomic images. For instance, FIG. 3 illustrates an overview of an architecture the digital molecular-phenomic embedding system 106 in accordance with one or more implementations herein. In particular, FIG. 3 illustrates the digital molecular-phenomic embedding system 106 utilizing a molecular structure and/or a phenomic image (with uni-modal pre-trained models) to generate molecular phenomic embeddings in a joint feature space.

For instance, as shown in FIG. 3, the digital molecular-phenomic embedding system 106 identifies a molecular structure(s) 302. Moreover, as shown in FIG. 3, the digital molecular-phenomic embedding system 106 utilizes the molecular structure(s) 302 with a molecular structural model 304 to generate a molecular structural embedding(s) 306.

As used herein, the term "molecular structure" (or sometimes referred to as "molecule") includes a chemical compound or structure that serves as a building block for a biological process, biochemical process, and/or medicinal treatment. Indeed, a molecular structure can include molecules (e.g., one or more atoms with bonds) that form a drug compound or medicine. In some cases, a molecule can include biomolecules, such as, but not limited to, proteins, gene-based molecules (e.g., nucleic acids DNA, RNA), gene knockout data, and/or lipids. Indeed, a molecular structure can include a molecular representation for a molecule, such as, but not limited to, a molecular formula, a structural formula, or a chemical notation. For example, a molecular representation can include a variety of digital representations, including, but not limited to, Simplified Molecular Input Line Entry System (SMILES), SMILES Arbitrary Target Specification (SMARTS), International Chemical Identifier (InChI), InChIKey, Molecular 2D/3D File Format (MOL2), Protein Data Bank Format (PDB), RDKit, XYZ Files, Canonical SMILES, Tensor Representations, and/or sequential attachment-based fragment embedding (SAFE) molecular representations as described in GENERATING LARGE-LANGUAGE MODEL COMPATIBLE SEQUENTIAL ATTACHMENT-BASED FRAGMENT EMBEDDING MOLECULAR REPRESENTATIONS, U.S. patent application Ser. No. 18/750,828, filed Jun. 21, 2024.

As used herein, the term "machine learning model" includes a computer algorithm or a collection of computer algorithms that can be trained and/or tuned based on inputs to approximate unknown functions. For example, a machine learning model can include a computer algorithm with branches, weights, or parameters that changed based on training data to improve for a particular task. Thus, a machine learning model can utilize one or more learning techniques (e.g., supervised or unsupervised learning) to improve in accuracy and/or effectiveness. Example machine learning models include various types of decision trees, support vector machines, Bayesian networks, random forest models, or neural networks (e.g., deep neural networks, generative adversarial neural networks, graph neural networks, convolutional neural networks, recurrent neural networks, or diffusion neural networks). Similarly, the term "machine learning data" refers to information, data, or files generated or utilized by a machine learning model. Machine learning data can include training data, machine learning parameters, or embeddings/predictions generated by a machine learning model.

Furthermore, as used herein, the term "molecular structural model" includes a computer model that generates a variety of molecular property identifiers or embeddings from input molecular structures. Indeed, a molecular structural model can include a machine learning model (e.g., a graph neural network) that generates one or more feature vector representations of a molecular structure to utilize with a variety of task heads to generate one or more inferences from the feature vector representations of the molecular structure. In one or more cases, the digital molecular-phenomic embedding system 106 generates a molecular structural embedding by generating (and utilizing) the one or more feature vector representations of an input molecular structure from a molecular structural model. In some cases, the molecular structural model can generate molecular fingerprints (as molecular structure embeddings) utilizing a molecular fingerprint generator as the molecular structural model.

As an example, the digital molecular-phenomic embedding system 106 can generate molecular structural embeddings by utilizing a molecular structural model (e.g., a graph neural network based molecular structural model) to generate graph representations (as embeddings) from an input molecular structure. Indeed, in one or more implementations, the digital molecular-phenomic embedding system 106 utilizes a graph neural network molecular structural model to generate a graph representation (as the molecular structural embedding) for an input molecular structure as described in TRAINING AND UTILIZING COMPOUND GRAPH NEURAL NETWORKS TO GENERATE BIOLOGICAL ACTIVITY PREDICTIONS FROM INPUT CHEMICAL COMPOUNDS, U.S. patent application Ser. No. 18/750,813, filed Jun. 21, 2024 (hereinafter U.S. patent application Ser. No. 18/750,813), which is incorporated herein by reference in its entirety.

In addition, as used herein, the term "molecular structural embedding" can include a feature vector or other numerical (or data) representation of a molecular structure. For instance, a molecular structural embedding can include an embedding (or feature vector) of a molecular structure generated by a machine learning model (e.g., a graph neural network as described above) to represent one or more latent features of the molecular structure. In one or more instances, a molecular structural embedding can include a graph representation that reflects nodes (e.g., node features) that correspond to atoms of an input molecule (or molecular structure) and edge (edge features) that correspond to bonds between atoms of the input molecule (e.g., as described in U.S. patent application Ser. No. 18/750,813).

In addition, as shown in FIG. 3, the digital molecular-phenomic embedding system 106 identifies a phenomic image(s) 308. As further shown in FIG. 3, the digital molecular-phenomic embedding system 106 utilizes the phenomic image(s) 308 with a phenomic image generative model 310 to generate a phenomic image embedding(s) 312.

As used herein, the term "microscopy representation" (or microscopy data) can include data that indicates or represents one or more characteristics of samples or other objects (e.g., cell structure samples, chemical objects, biological objects) obtained through microscopic instruments (e.g., a microscope, testing device). For example, a microscopy representation can include a phenomic image. Additionally, a microscopy representation can include transcriptomics data that indicates molecular structures expressed in a biological (or chemical) sample. For example, transcriptomics data can include an array or table of ribonucleic acid (RNA) or messenger RNA (mRNA) produced (e.g., an RNA count) in a cell or tissue sample for one or more perturbations. Although one or more implementations herein describe the digital molecular-phenomic embedding system 106 utilizing phenomic images, the digital molecular-phenomic embedding system 106 can utilize a variety of microscopy representations in accordance with one or more implementations herein.

Furthermore, as used herein, the term "phenomic image" (or "perturbation image"), can include a digital image portraying a cell (e.g., a cell after applying a molecule perturbation). For example, a phenomic image includes a digital image of a stem cell after application of a molecule perturbation (e.g., perturbing through applying a molecular structure) and further development of the cell. Thus, a phenomic image comprises pixels that portray a modified cell phenotype resulting from a particular cellular molecule perturbation (from a molecular structure).

Indeed, as used herein, the term "perturbation" (e.g., "cell perturbation") can include an alteration or disruption to a cell or the cell's environment (to elicit potential phenotypic changes to the cell) by applying a molecule or molecular structure. In particular, the term perturbation can include a gene perturbation (i.e., a gene-knockout perturbation) or a compound perturbation (e.g., a chemical molecule perturbation or a soluble factor perturbation). In one or more cases, these perturbations are accomplished by performing a perturbation experiment. A perturbation experiment can include a process for applying a molecular perturbation to a cell. A perturbation experiment can also include a process for developing/growing the perturbed cell into a resulting phenotype.

As an example, a gene perturbation can include gene-knockout perturbations (performed through a gene knockout experiment). For instance, a gene perturbation includes a gene-knockout in which a gene (or set of genes) is inactivated or suppressed in the cell (e.g., by CRISPR-Cas9 editing).

Furthermore, the term "compound perturbation" can include a cell perturbation using a compound molecular structure and/or soluble factor. For instance, a compound perturbation can include reagent profiling such as applying a small molecule to a cell and/or adding soluble factors to the cell environment. Additionally, a compound perturbation can include a cell perturbation utilizing the compound or soluble factor at a specified concentration. Indeed, compound perturbations performed with differing concentrations of the same molecule/soluble factor can constitute separate compound perturbations. A soluble factor perturbation is a compound perturbation that includes modifying the extracellular environment of a cell to include or exclude one or more soluble factors. Additionally, soluble factor perturbations can include exposing cells to soluble factors for a specified duration wherein perturbations using the same soluble factors for differing durations can constitute separate compound perturbations.

As used herein, the term "phenomic image embedding" (or phenomic autoencoder embeddings, phenomic perturbation autoencoder embeddings or phenomic perturbation embeddings) can include a numerical representation of a phenomic image. For example, a phenomic image embedding includes a vector representation of a phenomic image generated by a machine learning model (e.g., a phenomic image generative and/or encoding model, such as a masked autoencoder generative model, a generative adversarial neural network). Thus, a phenomic image embedding includes a feature vector generated by application of various machine learning (or encoder) layers (at different resolutions/dimensionality). Furthermore, in some implementations, the digital molecular-phenomic embedding system 106 can embed phenomic images into a low dimensional feature space via a generative machine learning model (e.g., a masked autoencoder model or channel-agnostic masked autoencoder model) to generate perturbation image embeddings (or phenomic perturbation autoencoder embeddings).

In some instances, the digital molecular-phenomic embedding system 106 can embed other microscopy representations (e.g., transcriptomics representations) into a low dimensional feature space via a generative machine learning model to generate microscopy representation embeddings (e.g., a numerical and/or feature vector representation of transcriptomics data). For instance, a microscopy representation embedding can include a vector representation of transcriptomics data generated by a machine learning model.

As used herein, the term "image embedding model" (or "phenomic image embedding model") can include a computer model that generates representations of a phenomic image. For example, an image embedding model can include a machine learning model (e.g., a phenomic image generative and/or encoding model, such as a masked autoencoder generative model, a generative adversarial neural network) that encodes (or embeds) a phenomic image into a latent space. In one or more implementations, the image embedding model includes unsupervised models and/or supervised models. In some instances, the image embedding model can include a masked autoencoder generative model.

In one or more implementations, the digital molecular-phenomic embedding system 106 applies a masked autoencoder generative model to a phenomic image of a cell to generate a phenomic image autoencoder embedding (as the phenomic image embedding). Indeed, the digital molecular-phenomic embedding system 106 can utilize a generative machine learning model (e.g., a masked autoencoder generative model) trained to generate predicted (or reconstructed) phenomic images from masked version of ground truth training phenomic images. In some cases, the digital molecular-phenomic embedding system 106 further utilizes (or applies) a masked autoencoder generative model that is trained utilizing a momentum-tracking optimizer to enable efficient training on large scale training image batches. Furthermore, the digital molecular-phenomic embedding system 106 can also utilize (or apply) a masked autoencoder generative model that utilizes Fourier transformation losses with multi-stage weighting to improve the accuracy of the generative machine learning model on the phenomic images during training. Indeed, the digital molecular-phenomic embedding system 106 can utilize (or apply) a masked autoencoder generative model to a phenomic image (or other microscopy representation) to generate a phenomic image embedding (or other microscopy representation embedding) as described in UTILIZING MASKED AUTOENCODER GENERATIVE MODELS TO EXTRACT MICROSCOPY REPRESENTATION AUTOENCODER EMBEDDINGS, U.S. patent application Ser. No. 18/545,399, filed Dec. 19, 2023, which is incorporated herein by reference in its entirety (hereinafter U.S. patent application Ser. No. 18/545,399).

In some instances, the digital molecular-phenomic embedding system 106 applies a supervised deep image embedding model (e.g., via a convolutional neural network model) to a phenomic image of a cell to generate a phenomic image embedding. For example, the digital molecular-phenomic embedding system 106 trains the supervised deep image embedding model to generate predicted perturbations from phenomic digital images. Indeed, the digital molecular-phenomic embedding system 106 utilizes neural network layers to generate vector representations of the phenomic digital images at different levels of abstraction and then utilize output layers to generate predicted perturbations. The digital molecular-phenomic embedding system 106 then trains the supervised deep image embedding model by comparing the predicted perturbations with ground truth perturbations. Moreover, the digital molecular-phenomic embedding system 106 can utilize the internal feature vectors generated by the supervised deep image embedding model (for an input phenomic image) as the phenomic image embeddings.

Moreover, as shown in FIG. 3, the digital molecular-phenomic embedding system 106 utilizes a contrastive molecular-phenomic embedding model 318 to generate molecular-phenomic embeddings in a joint feature space 320. For example, as shown in FIG. 3, the digital molecular-phenomic embedding system 106 utilizes the molecular structural embedding(s) 306 with a molecular encoder 314 (e.g., a structural encoder) of the contrastive molecular-phenomic embedding model 318 to generate an embedding in the joint feature space 320 (e.g., as a molecular-phenomic embedding). Moreover, as shown in FIG. 3, the digital molecular-phenomic embedding system 106 utilizes the phenomic image embedding(s) 312 with a vision encoder 316 of the contrastive molecular-phenomic embedding model 318 to generate an additional (or other) embedding in the joint feature space 320 (e.g., as a molecular-phenomic embedding).

As used herein, the term "contrastive molecular-phenomic embedding model" (or contrastive model) can include a machine learning model that combines samples from two or more domains (e.g., molecular structures and phenomic images or other microscopy representations) in a joint feature space to learn representations between the samples. For instance, a contrastive molecular-phenomic embedding model can learn to differentiate between similar and dissimilar data points by focusing on contrasts between data points for paired samples (e.g., pairings of molecular structures and phenomic images). Indeed, the digital molecular-phenomic embedding system 106 can utilize a contrastive molecular-phenomic embedding model to learn to promote similarities in a joint embedding (or feature) space between positive (similar) paired data points (e.g., positive molecular structure and phenomic image pairs) and demoting (or deemphasizing) negative (dissimilar) paired data points (e.g., negative molecular structure and phenomic image pairs).

In one or more instances, the digital molecular-phenomic embedding system 106 utilizes a vision encoder of the contrastive molecular-phenomic embedding model to generate molecular-phenomic embeddings from phenomic image embeddings in a joint feature space. Furthermore, the digital molecular-phenomic embedding system 106 can utilize a molecular encoder (e.g., a structural encoder) to generate molecular-phenomic embeddings from molecular structural embedding in the joint feature space. In one or more instances, a vision encoder and/or molecular encoder can include various machine learning models, such as a ResNet model or multi-layer perceptron model. Indeed, in one or more implementations, the digital molecular-phenomic embedding system 106 utilizes a contrastive molecular-phenomic embedding model that maps a molecular-phenomic embedding for a phenomic image and an additional molecular-phenomic embedding for a molecular structure closer in distance (in the joint feature space) when the phenomic image and molecular structure are related (or a positive pairing).

As used herein, the term "joint feature space" (sometimes referred to as "shared feature space," "joint molecular-phenomic feature space," "shared latent space," "joint latent space," or "joint molecular-phenomic latent space") can include a dimensional space (or matrix) in which data from different modalities (or sources) are represented in a common format (e.g., as molecular-phenomic embeddings). Indeed, in one or more cases, the digital molecular-phenomic embedding system 106 utilizes a contrastive molecular-phenomic embedding model to generate a joint feature space in which features from different modalities (e.g., a molecular structure, a phenomic image) are embedded or projected (as molecular-phenomic embeddings) such that similar concepts (from the different modalities) are placed closer together in the joint feature space (e.g., to represent relationships).

Indeed, as used herein, the term "molecular-phenomic embedding" can include feature vector or other numerical (or data) representation in a shared feature space for a molecular structure (via a molecular structural embedding) or a phenomic image or other microscopy representation (via a phenomic image embedding). For instance, the molecular-phenomic embedding can include a shared (or common) representation between different modalities (e.g., molecular structures and phenomic images). In one or more instances, the digital molecular-phenomic embedding system 106 utilizes molecular-phenomic embeddings to query between the different modalities (e.g., molecular structures and phenomic images) in a shared feature space and/or generate one or more additional molecular inferences (in accordance with one or more implementations herein).

For example, as shown in FIG. 3, the digital molecular-phenomic embedding system 106 can utilize molecular-phenomic embeddings from the joint feature space 320 to generate molecular inference(s) 322. In particular, the digital molecular-phenomic embedding system 106 can utilize generate molecular inference(s) 322 by determining similar molecules (e.g., via a comparison or retrieval), determining similar phenomic images (e.g., via a comparison or retrieval), performing comparisons between molecules and molecules and/or phenomic images and phenomic images, determining phenotypic impacts, and/or determining molecular activity classifications.

Although FIG. 3 illustrates the digital molecular-phenomic embedding system 106 utilizing both the molecular structure(s) 302 and the phenomic image(s) 308 as inputs to the contrastive molecular-phenomic embedding model 318, the digital molecular-phenomic embedding system 106 can individually utilize the input molecular structure(s) 302 or the phenomic image(s) 308 to generate a molecular-phenomic embedding in the joint feature space 320. Moreover, the digital molecular-phenomic embedding system 106 can generate molecular-phenomic embeddings in the joint feature space 320 from multiple molecular structures, multiple phenomic images, and/or a variety of molecular structure-phenomic image pairings.

As mentioned above, the digital molecular-phenomic embedding system 106 can combine molecular structural embeddings with concentration dose encodings to map a combined concentration structural embedding into a joint molecular-phenomic feature space. For example, FIG. 4 illustrates the digital molecular-phenomic embedding system 106 utilizing a contrastive molecular-phenomic embedding model to generate a molecular-phenomic embedding in a joint molecular-phenomic feature space from a molecular structure with an explicit concentration dose.

Figure 4:
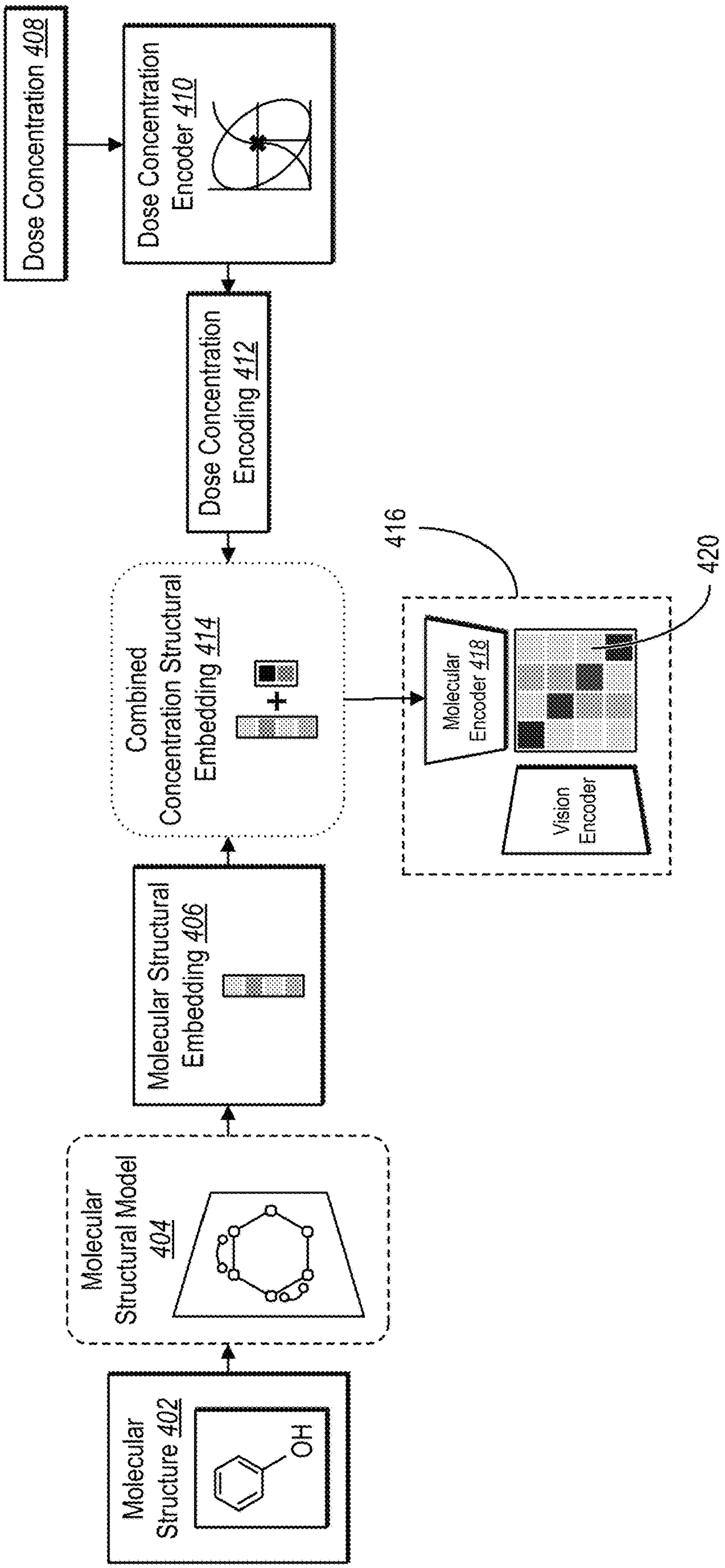
FIG. 4 illustrates a digital molecular-phenomic embedding system utilizing a contrastive molecular-phenomic embedding model to generate a molecular-phenomic embedding from a molecular structure with an explicit concentration dose in accordance with one or more implementations.

As shown in FIG. 4, the digital molecular-phenomic embedding system 106 utilizes a molecular structure 402 with a molecular structural model 404 to generate a molecular structural embedding 406 (in accordance with one or more implementations herein). In addition, as shown in FIG. 4, the digital molecular-phenomic embedding system 106 identifies a dose concentration 408 (corresponding to the molecular structure 402). Moreover, as shown in FIG. 4, the digital molecular-phenomic embedding system 106 utilizes a dose concentration encoder 410 to generate a dose concentration encoding 412 for the dose concentration 408. Furthermore, as shown in FIG. 4, the digital molecular-phenomic embedding system 106 utilizes combines the molecular structural embedding 406 and the dose concentration encoding 412 to generate a combined concentration structural embedding 414. Additionally, as illustrated in FIG. 4, the digital molecular-phenomic embedding system 106 utilizes the combined concentration structural embedding 414 with a molecular encoder 418 of the contrastive molecular-phenomic embedding model 416 to generate an embedding in the joint feature space 420 (e.g., as a molecular-phenomic embedding) in accordance with one or more implementations herein.

As used herein, the term "dose concentration" can include an amount of a molecular structure exposed (or administered) to a cell (or other biological matter). Indeed, a dose concentration can include an amount of a molecular structure (e.g., a molecular compound) administered during a phenotypic experiment. In one or more instances, the digital molecular-phenomic embedding system 106 utilizes a molecular dose concentration $c_i$ with a molecular encoder. For instance, the digital molecular-phenomic embedding system 106 can utilize different formulations for dosage concentrations (as encodings) $f'(c_i)$ (where f' maps $c_i$ into an encoding space $\mathbb{R}$). In one or more instances, the digital molecular-phenomic embedding system 106 can encode dosage concentrations as functional encodings f', such as, but not limited to, one-hot encodings, logarithm encodings, and/or sigmoid encodings.

Moreover, the digital molecular-phenomic embedding system 106 can generate a combined concentration structural embedding by combining a molecular structural embedding and a dose concentration encoding. In some cases, the digital molecular-phenomic embedding system 106 can combine the molecular structural embedding and the dose concentration encoding by concatenating the molecular structural embedding and the dose concentration encoding. In some instances, the digital molecular-phenomic embedding system 106 utilizes averaging, weighted sums, and/or element-wise operations to combine the molecular structural embedding and the dose concentration encoding.

As mentioned above, the digital molecular-phenomic embedding system 106 can train a contrastive molecular-phenomic embedding model to align relationships between molecular structures and phenomic images in a shared molecular-phenomic feature space. For example, FIG. 5 illustrates the digital molecular-phenomic embedding system 106 training a contrastive molecular-phenomic embedding model to generate molecular-phenomic embeddings in a shared molecular-phenomic feature space between molecular structures and phenomic images.

Figure 5:
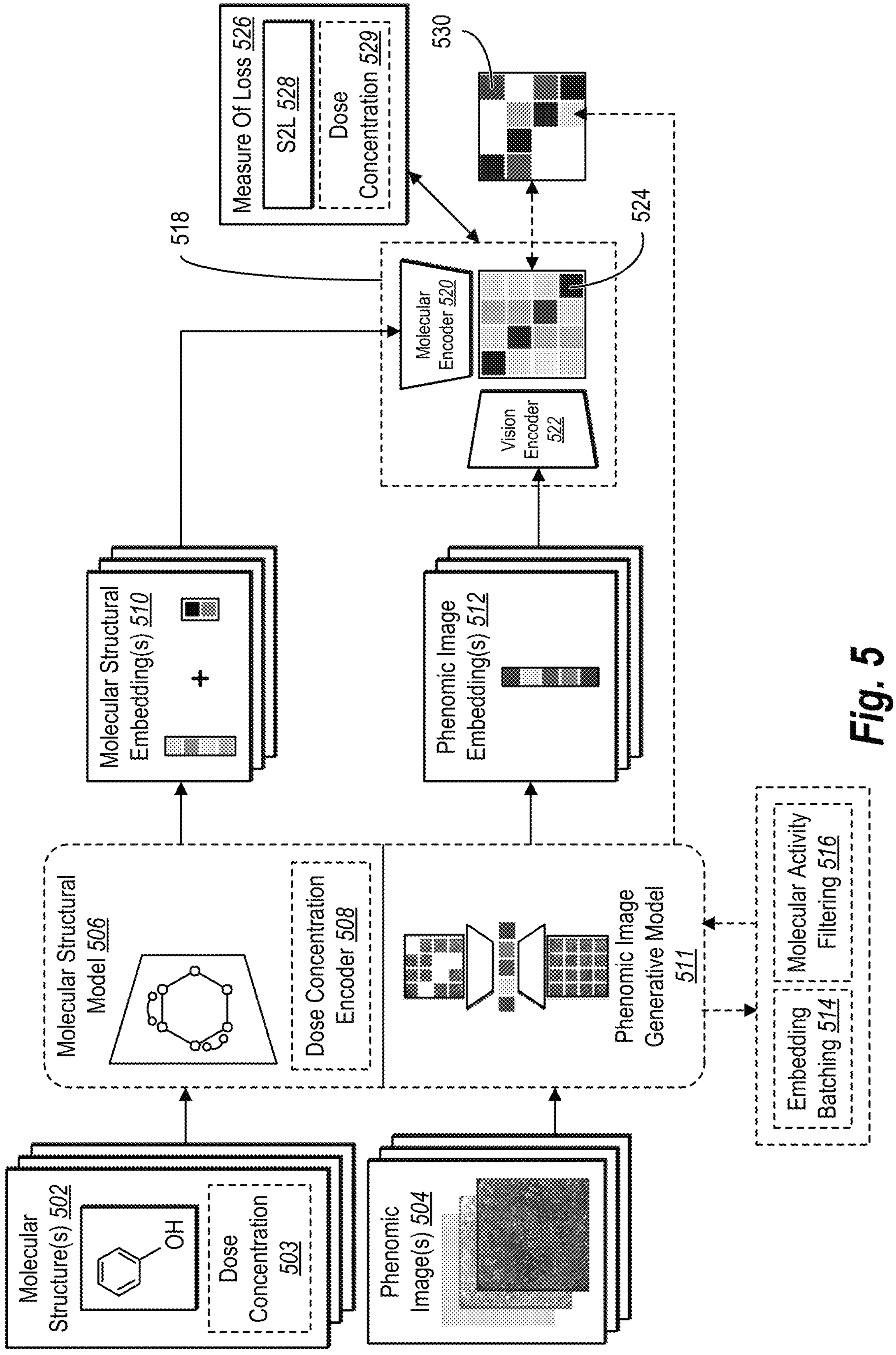
FIG. 5 illustrates a digital molecular-phenomic embedding system training a contrastive molecular-phenomic embedding model to generate molecular-phenomic embeddings in accordance with one or more implementations.

As shown in FIG. 5, the digital molecular-phenomic embedding system 106 identifies pairings between molecular structure(s) 502 and phenomic image(s) 504 (as training data). As mentioned above, the pairings between the molecular structure(s) 502 and the phenomic image(s) 504 include phenomic images portraying perturbations caused by a particular molecular structure. In addition, as shown in FIG. 5, the digital molecular-phenomic embedding system 106 can also include dose concentration 503 for the molecular structure(s) 502 corresponding to the phenomic image(s) 504 (e.g., the phenomic images portraying perturbations caused by a particular molecular structure at a particular dose concentration).

As further shown in FIG. 5, the digital molecular-phenomic embedding system 106 utilizes a molecular structural model 506 to generate a molecular structural embedding(s) 510 from the molecular structure(s) 502. Furthermore, as illustrated in FIG. 5, in some cases, the digital molecular-phenomic embedding system 106 can also utilize a dose concentration encoder 508 to generate a concentration encoding from the dose concentration 503 and combine the concentration encoding with an embedding of the molecular structure(s) (generated from the molecular structural model 506) to generate the molecular structural embedding(s) 510 (as a combined concentration structural embedding). Indeed, as further shown in FIG. 5, the digital molecular-phenomic embedding system 106 utilizes the molecular structural embedding(s) 510 with a molecular encoder 520 of the contrastive molecular-phenomic embedding model 518 to generate a molecular-phenomic embedding(s) in a shared feature space 524 for the molecular structural embedding(s) 510.

Furthermore, as shown in FIG. 5, the digital molecular-phenomic embedding system 106 utilizes a phenomic image generative model 511 to generate phenomic image embedding(s) 512 from the phenomic image(s) 504. In addition, as shown in FIG. 5, the digital molecular-phenomic embedding system 106 utilizes the phenomic image embedding(s) 512 with a vison encoder 522 of the of the contrastive molecular-phenomic embedding model 518 to generate a molecular-phenomic embedding(s) in a shared feature space 524 for the phenomic image embedding(s) 512.

Indeed, upon mapping the molecular structural embedding(s) 510 and the molecular-phenomic embedding(s) 512 in the shared feature space 524 (as described above), the digital molecular-phenomic embedding system 106 can determine a measure of loss (a contrastive loss) for the contrastive molecular-phenomic embedding model 518. In particular, the digital molecular-phenomic embedding system 106 can compare the molecular-phenomic embeddings of the phenomic image(s) 504 and the molecular structure(s) 502 (and dose concentration 503) to determine a measure of loss (e.g., based on a similarity or dissimilarity of the molecular-phenomic embeddings in the shared feature space 524). Furthermore, the digital molecular-phenomic embedding system 106 can utilize the measure of loss to modify parameters of the contrastive molecular-phenomic embedding model (e.g., the molecular encoder and/or vision encoder).

As an example, the digital molecular-phenomic embedding system 106 can modify parameters of the contrastive molecular-phenomic embedding model (e.g., the molecular encoder and/or vision encoder) to modify how the contrastive molecular-phenomic embedding model maps molecular-phenomic embeddings for phenomic images and/or molecular structures. For instance, the digital molecular-phenomic embedding system 106 can modify the parameters of the contrastive molecular-phenomic embedding model to cause the contrastive molecular-phenomic embedding model to generate molecular-phenomic embeddings for phenomic images and/or molecular structures such that distances between the molecular-phenomic embeddings in the shared feature space are reconfigured.

To illustrate, the digital molecular-phenomic embedding system 106 can modify the parameters of the contrastive molecular-phenomic embedding model to minimize (or reduce) a measure of loss (or error) for the mappings of the molecular-phenomic embeddings corresponding to the phenomic image(s) 504 and the molecular structure(s) 502 (and dose concentration 503). Indeed, the digital molecular-phenomic embedding system 106 can iteratively modify parameters of the contrastive molecular-phenomic embedding model to push (or map) molecular-phenomic embeddings corresponding to the positive pairs of the phenomic image(s) 504 and the molecular structure(s) 502 closer in distance in the shared feature space 524. Moreover, in one or more instances, the digital molecular-phenomic embedding system 106 can iteratively modify parameters of the contrastive molecular-phenomic embedding model to push (or map) molecular-phenomic embeddings corresponding to the negative pairs of the phenomic image(s) 504 and the molecular structure(s) 502 (e.g., incorrect pairs) further apart in distance in the shared feature space 524. In some cases, the digital molecular-phenomic embedding system 106 utilizes back propagation of the measure of loss 526 to modify parameters of the contrastive molecular-phenomic embedding model (e.g., to train the contrastive molecular-phenomic embedding model).

In some implementations, the digital molecular-phenomic embedding system 106 determines a measure of loss (contrastive loss) to modify the contrastive molecular-phenomic embedding model by utilizing a retrieval approach. For example, the digital molecular-phenomic embedding system 106 generates the molecular-phenomic embeddings of the phenomic images and the molecular structures (and corresponding dose concentrations) in a shared feature space. Furthermore, the digital molecular-phenomic embedding system 106 can utilize the molecular-phenomic embedding corresponding to a phenomic image to retrieve, from the shared feature space, molecular-phenomic embeddings of molecular structures (and dose concentrations) predicted to match with (or to be similar to) the molecular-phenomic embedding corresponding to the phenomic image. Additionally, the digital molecular-phenomic embedding system 106 can compare the retrieved molecular structures (and dose concentrations) to ground truth molecular structures (and dose concentrations) corresponding to the phenomic image to determine a measure of loss.

Furthermore, the digital molecular-phenomic embedding system 106 can utilize the measure of loss to modify parameters of the contrastive molecular-phenomic embedding model with an objective to learn molecular-phenomic embeddings for the phenomic images and molecular structures (and dose concentrations) that result in accurate retrieval rates (e.g., a threshold retrieval rate) between the phenomic images and molecular structures. In particular, in one or more instances, the digital molecular-phenomic embedding system 106 can utilize the measure of loss to modify the parameters of the contrastive molecular-phenomic embedding model to increase a likelihood of positive pair retrieval from the contrastive molecular-phenomic embedding generator model's shared feature space. Indeed, the digital molecular-phenomic embedding system 106 can train the contrastive molecular-phenomic embedding model by retrieving molecular-phenomic embeddings corresponding to molecular structures (and dose concentrations) in response to sample molecular-phenomic embeddings for phenomic images or, alternatively, retrieving molecular-phenomic embeddings corresponding to phenomic images in response to sample molecular-phenomic embeddings for molecular structures (and dose concentrations) in the shared feature space. Indeed, utilizing retrieval for training the contrastive molecular-phenomic embedding model is described in greater detail below (e.g., with reference to FIG. 6).

In some instances, the digital molecular-phenomic embedding system 106 can train the contrastive molecular-phenomic embedding model utilizing positive pairs between phenomic images and molecular structures (with dose concentrations) and/or negative pairs between phenomic images and molecular structures (with dose concentrations). For example, the digital molecular-phenomic embedding system 106 can modify parameters of the contrastive molecular-phenomic embedding model to increase a likelihood of retrieval of a positive pairing between phenomic images and molecular structures (with dose concentrations) from molecular-phenomic embeddings in the shared feature space. In some cases, the digital molecular-phenomic embedding system 106 can modify parameters of the contrastive molecular-phenomic embedding model to decrease a likelihood of retrieval of a negative pairing between phenomic images and molecular structures (with dose concentrations) from molecular-phenomic embeddings in the shared feature space.

As further shown in FIG. 5, in some cases, the digital molecular-phenomic embedding system 106 determines an inter-sample similarity aware loss (S2L) 528 as the measure of loss 526 (contrastive loss). Indeed, as shown in FIG. 5, the digital molecular-phenomic embedding system 106 weighs the measure of loss 526 determined (as described above) for the contrastive molecular-phenomic embedding model 518 (between molecular-phenomic embeddings) by utilizing a similarity distance of a corresponding phenomic image embedding to other phenomic image embeddings in a phenomic image embedding feature space 530. For instance, the digital molecular-phenomic embedding system 106 can determine a similarity distance measure between a phenomic image embedding (from a positive pair of molecular-phenomic embeddings in the shared feature space) and other phenomic image embeddings in the phenomic image embedding feature space 530. Moreover, the digital molecular-phenomic embedding system 106 can utilize the similarity distance measure with the measure of loss 526 to generate an inter-sample similarity aware loss (S2L) 528 that weighs a contrastive loss more significantly to distinguish a pair of molecular-phenomic embeddings when the phenomic image embedding similarity distance measure indicates a distinct phenotypic representation.

For example, the digital molecular-phenomic embedding system 106 can determine a contrastive measure of loss that is weighted (as an S2L loss) to further increase the distance between positive pair samples of molecular structures and phenomic images (as molecular-phenomic embeddings in the shared feature space) and other molecular-phenomic embeddings when an underlying phenomic image embedding similarity distance measure indicates a distinct phenotypic representation. In addition, the digital molecular-phenomic embedding system 106 can determine a contrastive measure of loss that is weighted (as the S2L loss) to reduce a distance between positive pair molecular-phenomic embedding samples and other molecular-phenomic embeddings when an underlying phenomic image embedding similarity distance measure indicates a non-distinct phenotypic representation. Furthermore, in some cases, the digital molecular-phenomic embedding system 106 determines a contrastive measure of loss that is weighted (as the S2L loss) to reduce a distance between positive pair molecular-phenomic embedding samples and other molecular-phenomic embeddings when an underlying phenomic image embedding similarity distance measure indicates that a corresponding molecular structure is inactive (through similarities with other phenomic images of inactive molecular structures). For instance, the digital molecular-phenomic embedding system 106 determines an S2L loss for the contrastive molecular-phenomic embedding model as described below (e.g., with reference to FIG. 6 and function (2)).

Furthermore, as shown in FIG. 5, the digital molecular-phenomic embedding system 106 can also utilize dose concentration 529 (implicitly) during training to determine the measure of loss 526. For instance, the digital molecular-phenomic embedding system 106 can determine a measure of loss (or S2L loss) for molecular structures with different dose concentrations as distinct classes (as a dose aware S2L loss). Indeed, the digital molecular-phenomic embedding system 106 can push sample pairs of molecular-phenomic embeddings (of molecular structure with different dose concentrations and corresponding phenomic images) further apart in the shared feature space proportional to similarities between the phenomic image embeddings (of the phenomic images). In particular, the digital molecular-phenomic embedding system 106 can determine a contrastive loss (e.g., an S2L loss) that distinguishes between molecular structures with different dose concentrations to emphasize distinct phenotypic representations from underlying phenomic image embeddings of the different dose concentrations).

As further shown in FIG. 5, the digital molecular-phenomic embedding system 106 can utilize embedding batching 514 with the phenomic image generative model 511 while training the contrastive molecular-phenomic embedding model 518. For example, the digital molecular-phenomic embedding system 106 can batch phenomic images belonging to a particular molecular structure (e.g., a particular perturbation or phenomic experiment) by combining phenomic embeddings corresponding to the phenomic images. Indeed, the digital molecular-phenomic embedding system 106 can batch phenomic image embeddings to reduce the inducement of noise in a latent space as a result of random perturbations in a phenomic experiment process (e.g., to emphasize biologically meaningful variations from phenomic images). By batching the phenomic image embeddings, the digital molecular-phenomic embedding system 106 can enable a contrastive molecular-phenomic embedding model to capture molecular features affecting cell morphology through biologically meaningful variations from phenomic images while reducing noise from other unmeaningful variations.

For instance, the digital molecular-phenomic embedding system 106 can combine the phenomic image embeddings (for embedding batching) (from a phenomic image generative model) utilizing a variety of approaches. For example, the digital molecular-phenomic embedding system 106 can utilize approaches, such as, but not limited to, averaging the phenomic image embeddings, concatenation of the phenomic image embeddings, utilizing transformer attention-based approaches, and/or max and/or min pooling of the phenomic image embeddings. For instance, in one or more implementations, the digital molecular-phenomic embedding system 106 generates a batched phenomic image embedding by averaging samples, $z_x$, generated with the same molecular structure (or perturbation) $m_i$ (for a particular dose concentration) over multiple phenomic experiments (or simulations) $\epsilon_i$. In particular, the digital molecular-phenomic embedding system 106 can average phenomic image embeddings corresponding to a particular molecular structure (or perturbation) $m_i$ in accordance with the following function:

$$\frac{1}{N}\sum\nolimits_{i\in N}^{1} z_{x_i} \tag{1}$$

Additionally, as shown in FIG. 5, the digital molecular-phenomic embedding system 106 can utilize molecular activity filtering 516 with the phenomic image generative model 511 while training the contrastive molecular-phenomic embedding model 518. For instance, the digital molecular-phenomic embedding system 106 can utilize phenomic image embedding(s) generated from the phenomic image(s) to identify training pairs corresponding to inactive molecules (from the molecular structure(s) 502). Indeed, the digital molecular-phenomic embedding system 106 can under sample the inactive molecule samples (e.g., molecular structure and phenomic image pairs) while training the contrastive molecular-phenomic embedding model 518. In particular, by under sampling inactive molecule samples, the digital molecular-phenomic embedding system 106 can limit (or reduce) noise in training created from training pairs corresponding to molecules that have no (or minimal) effect on cell morphology that lead to misannotations (under the assumption that data-pairs have an underlying biological relationship).

For example, to under sample (or filter) inactive molecules, the digital molecular-phenomic embedding system 106 extracts phenomic image embeddings and determines a relative activity of each molecular structure m (and dose concentration c) (e.g., perturbation), $(m_i, c_i)\in(M, C)$. In particular, the digital molecular-phenomic embedding system 106 can utilize a rank of similarity measures (e.g., cosine similarities) between replicates produced for a molecular structure (as a perturbation) against a null distribution. Indeed, the digital molecular-phenomic embedding system 106 can establish a null distribution by determining (or calculating) similarity measures (cosine similarities) from (random) pairs of phenomic image embeddings generated with molecular structure perturbations (and dose concentrations) ($m_j$, $c_j$), ($m_k$, $c_k$). Moreover, the digital molecular-phenomic embedding system 106 can determine a p-value from the determined similarity measures and filter sample pairs that are likely to belong to the null distribution with a molecular activity threshold y. For example, in some instances, the digital molecular-phenomic embedding system 106 can utilize a p value cutoff $\psi \in \Psi'$ to quantify (or determine) molecular activity. Indeed, in one or more instances, the digital molecular-phenomic embedding system 106 identifies molecules that do not meet (e.g., are less than or less than or equal to) the p value cutoff $\psi$ as active molecules. Moreover, in one or more implementations, the digital molecular-phenomic embedding system 106 identifies molecules that satisfy (e.g., are greater than or greater than or equal to) the p value cutoff $\psi$ as inactive molecules.

Figure 6:
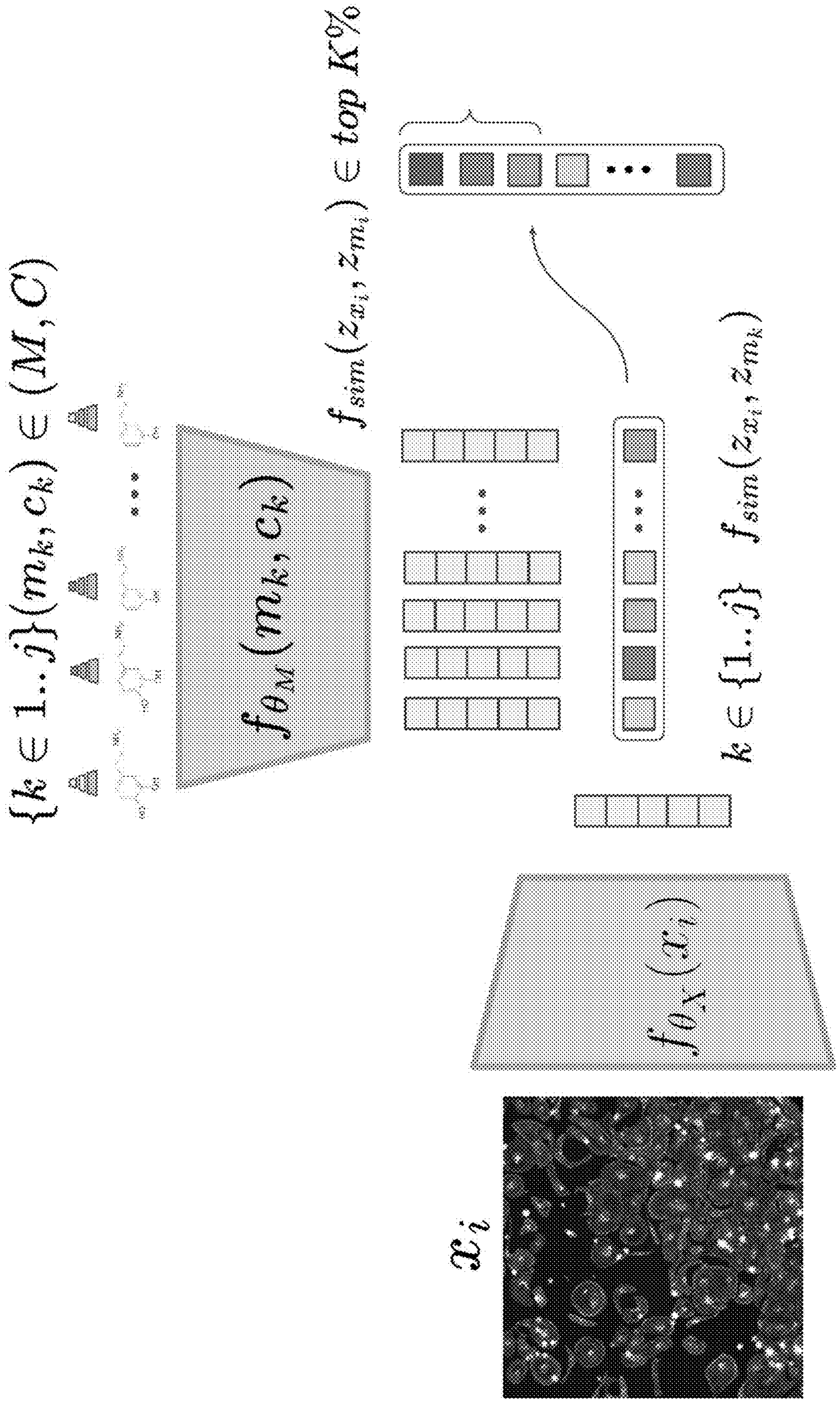
FIG. 6 illustrates a digital molecular-phenomic embedding system utilizing a retrieval approach with a contrastive molecular-phenomic embedding model in accordance with one or more implementations.

Moreover, FIG. 6 illustrates the digital molecular-phenomic embedding system 106 utilizing a retrieval approach with a contrastive molecular-phenomic embedding model (e.g., for training, screening, and/or inference). In particular, the digital molecular-phenomic embedding system 106 can utilize the contrastive molecular-phenomic embedding model to learn a joint latent space (or shared feature space) that maps data from phenomic images (portraying phenomic experiments of treated cells) and corresponding molecular structural data (e.g., molecular perturbations) in a shared latent space. Indeed, in one or more embodiments, the digital molecular-phenomic embedding system 106 identifies a set of phenomic experiments E defined as a tuple (X, M, C, $\Psi$). Moreover, each experiment $\epsilon \in \varepsilon$ can include data samples $x_i \in X$ (e.g., as phenomic images) and data samples $m_i \in M$ (as molecular structures or molecule perturbations) obtained at varying dosage concentrations $c_i \in C$ with a molecular activity threshold $\Psi$ (e.g., for under sampling training data based on molecular inactivity as described in FIG. 5).

Indeed, FIG. 6 illustrates the digital molecular-phenomic embedding system 106 performing phenomolecular retrieval (using a contrastive molecular-phenomic embedding model in accordance with one or implementations herein). In particular, as shown in FIG. 6, for a phenomic image $x_i$, the digital molecular-phenomic embedding system 106 can identify a matching molecular structure $m_i$ (i.e., a molecular perturbation) (and a dose concentration $c_i$) that induces the morphological effects (portrayed or depicted in the phenomic image $x_i$). Indeed, as further shown in FIG. 6, the digital molecular-phenomic embedding system 106 generates embeddings (e.g., molecular-phenomic embeddings) for the molecular structures $m_i$ and corresponding dosage concentrations $c_i$ (as ($m_1$, $c_1$), . . . , ($m_k$, $c_k$)) (e.g., molecular structural embeddings in accordance with one or more implementations herein) utilizing the function fem ($m_k$, $c_k$) to map the samples into a joint latent space $\mathbb{R}^d$. In addition, as shown in FIG. 6, the digital molecular-phenomic embedding system 106 generates an embedding (e.g., a molecular-phenomic embedding) for the phenomic image $x_i$ (e.g., a phenomic image embedding in accordance with one or more implementations herein) utilizing the function $f_{\theta_X}(x_i)$ to map the samples into the joint latent space $\mathbb{R}^d$.

Furthermore, as shown in FIG. 6, the digital molecular-phenomic embedding system 106 can determine a similarity measurement ($f_{sim}$) between generated molecular-phenomic embeddings $z_{x_i}$ and $z_{m_k}$ utilizing the function $f_{sim}(z_{x_i}, z_{m_k})$. Moreover, as shown in FIG. 6, the digital molecular-phenomic embedding system 106 utilizes the similarity measurements $f_{sim}(z_{x_i}, z_{m_k})$ to rank ($m_1$, $c_1$), . . . , ($m_k$, $c_k$) to retrieve a top K % of molecular structures (with dose concentrations) for the phenomic image $x_i$. Furthermore, as shown in FIG. 6, the digital molecular-phenomic embedding system 106 trains the contrastive molecular phenomic embedding model to learn functions $f_{\theta_M}$(m, c) and $f_{\theta_X}$(x) to result in accurate (or high) retrieval rates (e.g., by satisfying a threshold retrieval rate) of ($m_i$, $c_i$) utilized to perturb the phenomic image $x_i$. In some implementations, during training, the digital molecular-phenomic embedding system 106 determines a measure of loss (in accordance with one or more implementations herein) by determining whether the ground truth sample pair of the phenomic image and molecular structure (and dose concentration) appears in the retrieved top K % (from the above described retrieval).

Although FIG. 6 illustrates utilizing a single phenomic image $x_i$, the digital molecular-phenomic embedding system 106 can perform the retrieval approach illustrated in FIG. 6 for multiple phenomic images. In some instances, the digital molecular-phenomic embedding system 106 can utilize, within the retrieval approach illustrated in FIG. 6, multiple phenomic images corresponding to the same molecular structures and dose concentrations. In some implementations, the digital molecular-phenomic embedding system 106 can utilize, within the retrieval approach illustrated in FIG. 6, multiple phenomic images corresponding to different combinations of molecular structures and/or dose concentrations (e.g., from multiple phenomic experiments).

As described above, the digital molecular-phenomic embedding system 106 determines a measure of loss (a contrastive loss) for the contrastive molecular-phenomic embedding model. For instance, the digital molecular-phenomic embedding system 106 can utilizes a measure of contrastive loss to improve (or maximize) a joint likelihood of a phenomic image $x_i$ and a paired molecular structure $m_i$. For example, for a set of N×N (random) training samples ($x_1$, $m_1$, $c_1$), . . . , ($x_N$, $m_N$, $c_N$) that include N positive samples at kth index and (N−1)×N negative samples, the digital molecular-phenomic embedding system 106 determines a measure of loss for the contrastive molecular-phenomic embedding model to improve (or maximize) the likelihood of positive training sample pairs while reducing (or minimizing) the likelihood of negative training sample pairs.

As an example, the digital molecular-phenomic embedding system 106 can determine an inter-sample similarity aware loss (S2L) as the contrastive measure of loss (e.g., a soft-weighted sigmoid locked loss). For instance, the digital molecular-phenomic embedding system 106 can leverage inter-sample similarities and robustness (from phenomic images) to label noise to mitigate non-impactful and/or inactive molecular perturbations while training the contrastive molecular-phenomic embedding model. For example, the set of N×N (random) training samples ($x_1$, $m_1$, $c_1$), . . . , ($x_N$, $m_N$, $c_N$) that include N positive samples at kth index and (N−1)×N negative samples, the digital molecular-phenomic embedding system 106 can determine an inter-sample similarity aware loss ($\mathcal{L}_{S2L}$) in accordance with the following function:

$$\mathcal{L}_{S2L} = -\frac{1}{N}\sum_{i=1}^{N}\sum_{j=1}^{N}\log\left[\frac{w_{i,j}^{x}}{1+\exp\left(-\alpha z_{x_i}\cdot z_{m_j}+b\right)} + \frac{\left(1-w_{i,j}^{x}\right)}{1+\exp\left(\alpha z_{x_i}\cdot z_{m_j}+b\right)}\right] \quad (2)$$

In the above mentioned function (2), the digital molecular-phenomic embedding system 106 can utilize molecular-phenomic embeddings $z_{x_i}$ (from phenomic images) and molecular-phenomic embeddings $z_{m_j}$ (from molecular structures). In addition, with reference to the function (2), the digital molecular-phenomic embedding system 106 can utilize a learnable temperature and bias parameters a and b for a calibrated sigmoid function (e.g., of the S2L loss). In one or more instances, the digital molecular-phenomic embedding system 106 can utilize dose concentrations with the molecular structures to determine the inter-sample similarity aware loss ($\mathcal{L}_{S2L}$).

Furthermore, in reference to the function (2), the digital molecular-phenomic embedding system 106 utilizes an inter-sample similarity function (weight)

$$w_{i,j}^{x}$$

determined (or generated) from phenomic image embeddings (e.g., using phenomic images with a phenomic image generative model in accordance with one or more implementations herein). For example, to determine the inter-sample similarity function (weight)

$$w_{i,j}^{x},$$

the digital molecular-phenomic embedding system 106 can utilize similarity measurements (e.g., distances) between phenomic image embeddings in a phenomic image embedding space. Indeed, the digital molecular-phenomic embedding system 106 can utilize the inter-sample similarity function (weight)

$$w_{i,j}^{x}$$

for the inter-sample similarity aware loss (S2L) as a soft multi-label training oriented loss (e.g., with continuous labels that are determined by sample similarity in the phenomic image embedding space).

In one or more instances, to determine the inter-sample similarity function (weight)

$$w_{i,j}^{x},$$

the digital molecular-phenomic embedding system 106 can utilize a similarity measure distance between phenomic image embeddings in a phenomic image embedding space. For instance, the digital molecular-phenomic embedding system 106 can utilize cosine similarities and/or L2 distances. In one or more implementations, the digital molecular-phenomic embedding system 106 determines the inter-sample similarity function (weight)

$$w_{i,j}^{x}$$

by utilizing an arctangent of L2 distances between phenomic image embeddings in a phenomic image embedding space. To illustrate, the digital molecular-phenomic embedding system 106 can determine inter sample distances utilizing an arctangent of L2 distances between phenomic image embeddings in accordance with the following function:

$$\arctan(z_{x_i} - z_{x_j}\|_2^2/c) * \frac{4}{\pi} - 1 \tag{3}$$

In the above mentioned function (3), the digital molecular-phenomic embedding system 106 can utilize a constant c indicating a median L2 distance (or other similarity distance measurement) between a null set of phenomic image embeddings. In some implementations, the digital molecular-phenomic embedding system 106 utilizes similarities below a threshold k (e.g., a number of training samples or index) to 0 (e.g., $\lceil w \rceil^k$). Indeed, utilizing an arctangent of L2 distances separate inactive molecules from other molecule pairs to identify inactive molecules (for under sampling inactive molecule training data) and for sample similarities in the determination of the S2L loss.

As used herein, the term "contrastive loss" can include a loss function with an objective to learn an embedding space in which similar data points are close in distance and dissimilar data points are further apart in distance. Indeed, the digital molecular-phenomic embedding system 106 can determine a contrastive loss using positive pairs (e.g., phenomic image embedding and molecular structural embeddings that are related) and negative pairs (e.g., phenomic image embedding and molecular structural embeddings that are not related or have no annotated relation). In some cases, the digital molecular-phenomic embedding system 106 can utilize a softmax of similarity distances as a contrastive loss.

In addition, as used herein, the term "similarity measurement" (or "similarity distance") can include a metric or value indicating likeness, relatedness, or similarity. For instance, a similarity measurement includes a metric indicating relatedness between two embeddings (e.g., between two molecular-phenomic embeddings). To illustrate, the digital molecular-phenomic embedding system 106 can determine a similarity measure by comparing two feature vectors in the molecular-phenomic shared feature space. In some instances, a similarity measurement can include similarity logits and/or dissimilarity logits. Thus, a similarity measurement can include a cosine similarity between feature vectors or a measure of distance (e.g., Euclidian distance, L2 distance) in a feature space.

Moreover, as used herein, the term "molecule activity classification" can include a determination of whether a molecule is active or inactive (e.g., causes a biologically meaningful perturbation). For instance, the digital molecular-phenomic embedding system 106 can determine a molecule activity classification by labeling (or determining) a molecular structure as active or inactive in accordance with one or more implementations herein.

Although one or more implementations describes the digital molecular-phenomic embedding system 106 utilizing molecular structure and phenomic image data, the digital molecular-phenomic embedding system 106 can train the contrastive molecular-phenomic embedding model (in accordance with one or more implementations herein) on gene-knockout data. For example, the digital molecular-phenomic embedding system 106 can utilize a gene embedding model to generate a gene embedding and align the gene embedding to a corresponding phenomic image embedding (in a shared feature space) utilizing a contrastive loss in accordance with one or more implementations herein. For example, the digital molecular-phenomic embedding system 106 can utilize a gene embedding model, such as, but not limited to, RNA sequencing models, isoform sequencing models, and/or protein sequence transformer-based models.

Indeed, the digital molecular-phenomic embedding system 106 can train the contrastive molecular-phenomic embedding model (in accordance with one or more implementations herein) to identify relationships between gene-knockout data (e.g., as a molecular structure) and phenomic images. In some cases, the digital molecular-phenomic embedding system 106 utilize gene-knockout data as molecular structure data in accordance with one or more implementations. In some embodiments, the digital molecular-phenomic embedding system 106 utilizes gene-knockout data as an additional modality in the contrastive molecular-phenomic embedding model by training the contrastive molecular-phenomic embedding model on gene-knockout data utilizing an additional contrastive loss (in accordance with one or more implementations herein) in conjunction to molecular structural embeddings for molecules.

As mentioned above, the digital molecular-phenomic embedding system 106 can utilize molecular-phenomic embeddings (generated by a contrastive molecular-phenomic embedding model for molecular structures and/or phenomic images) for a variety of tasks. Indeed, the digital molecular-phenomic embedding system 106 can utilize the molecular-phenomic embeddings to generate a variety of molecular inferences. For example, FIGS. 7 and 8 illustrate the digital molecular-phenomic embedding system 106 utilizing molecular-phenomic embeddings.

Figure 7:
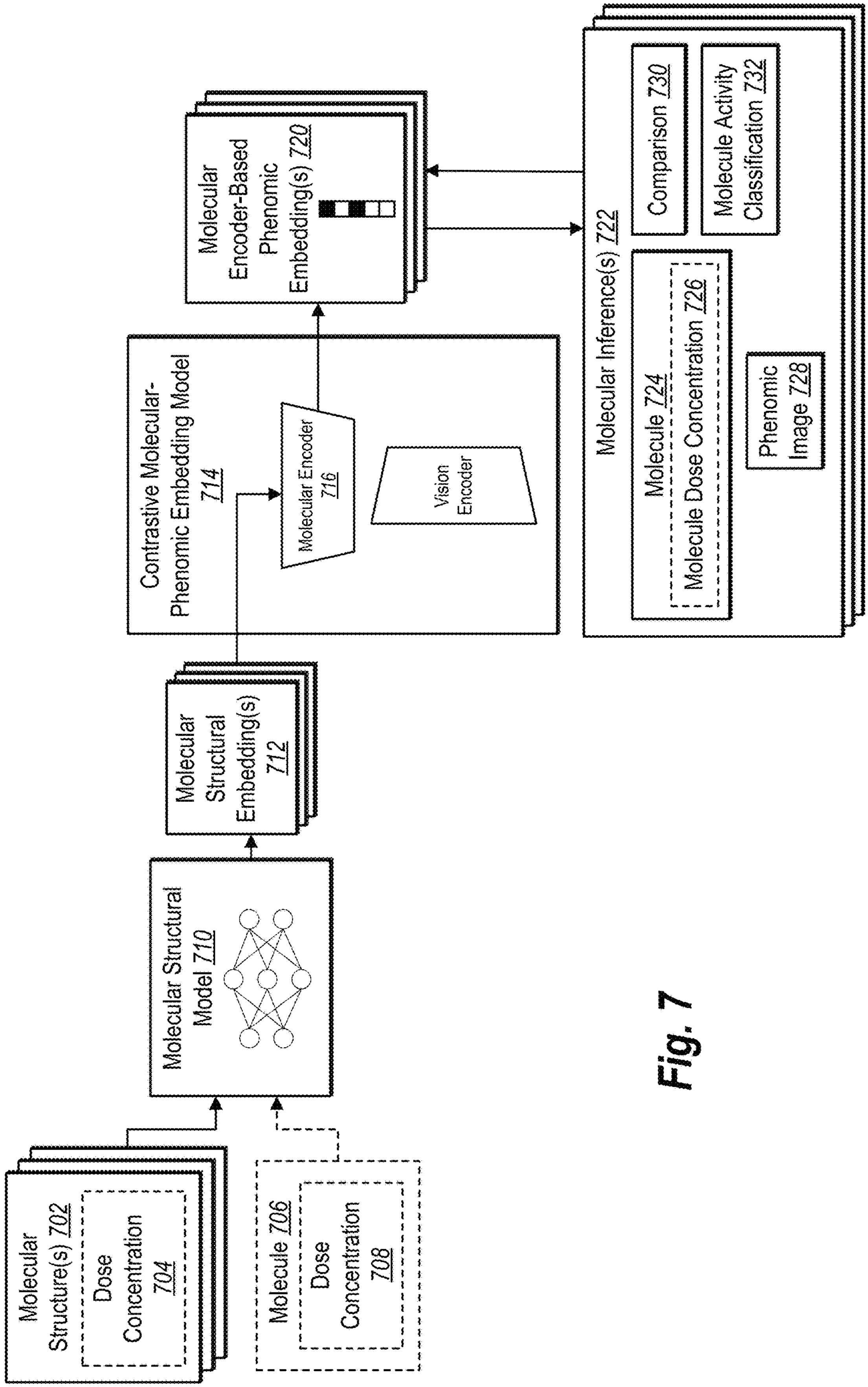
FIG. 7 illustrates a digital molecular-phenomic embedding system determining molecular inferences from molecular-phenomic embeddings in relation to a molecular structure in accordance with one or more implementations.
Figure 8:
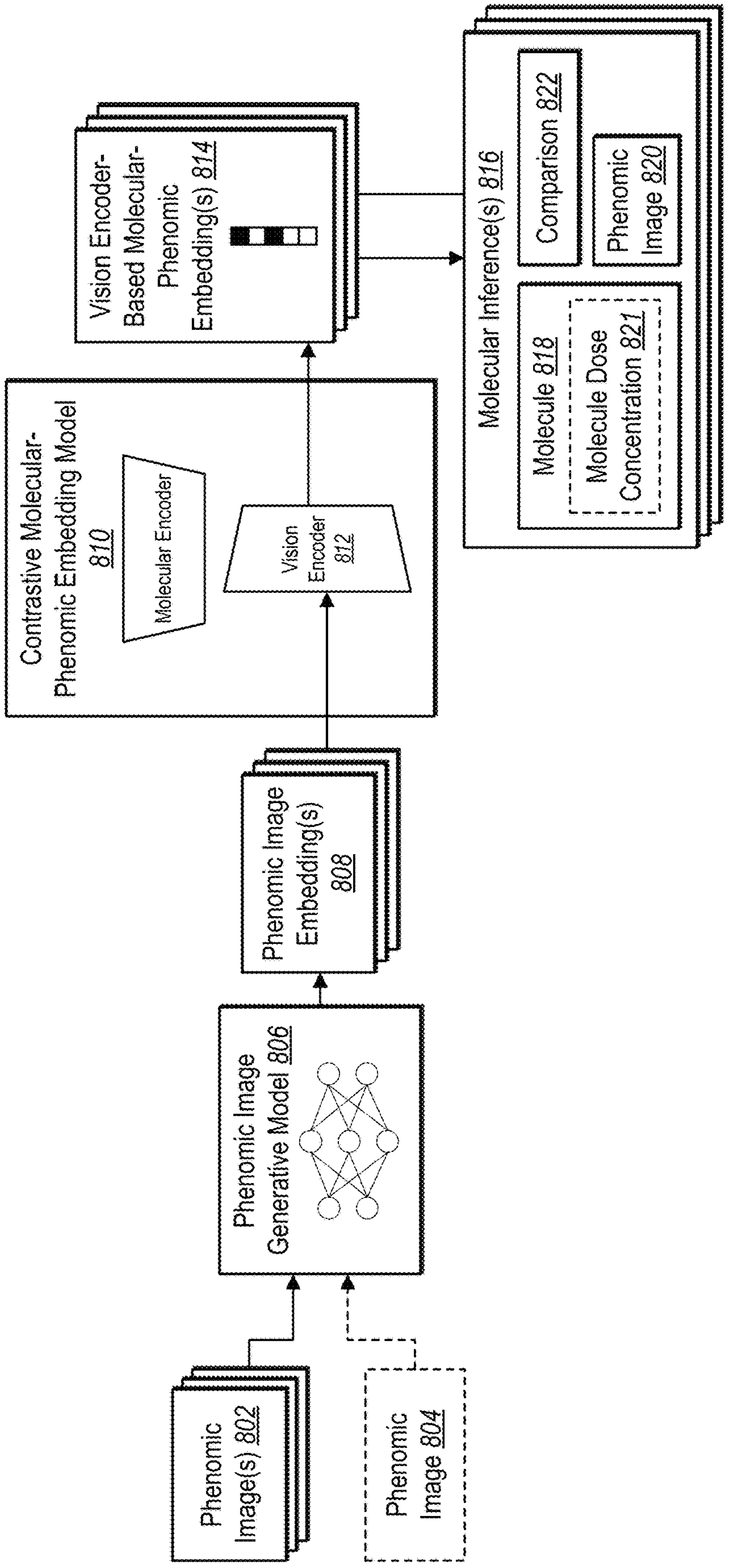
FIG. 8 illustrates a digital molecular-phenomic embedding system determining molecular inferences from molecular-phenomic embeddings in relation to a phenomic image in accordance with one or more implementations.

For instance, FIG. 7 illustrates the digital molecular-phenomic embedding system 106 determining (or generating) molecular inferences from molecular-phenomic embeddings in relation to a molecular structure. As shown in FIG. 7, the digital molecular-phenomic embedding system 106 utilizes molecular structure(s) 702 (e.g., from a molecular structure library) with a molecular structural model 710 to generate molecular structural embedding(s) 712 to utilize with a molecular encoder 716 (of a trained contrastive molecular-phenomic embedding model 714) to generate a molecular encoder-based molecular-phenomic embedding(s) 720 (in accordance with one or more implementations herein). In some instances, as shown in FIG. 7, the digital molecular-phenomic embedding system 106 utilizes the molecular structure(s) 702 corresponding to a particular dose concentration 704 to generate the molecular encoder-based molecular-phenomic embedding(s) 720 (in accordance with one or more implementations herein). As further shown in FIG. 7, the digital molecular-phenomic embedding system 106 utilizes the molecular encoder-based molecular-phenomic embedding(s) 720 generated from the molecular structure(s) 702 to generate a variety of molecular inference(s) 722.

In some instances, as shown in FIG. 7, the digital molecular-phenomic embedding system 106 can generate molecular inferences from singular input molecules. For example, as shown in FIG. 7, the digital molecular-phenomic embedding system 106 can receive a molecule 706 (with a dose concentration 708). Furthermore, the digital molecular-phenomic embedding system 106 can utilize the molecule 706 with the molecular structural model 710 to generate the molecular structural embedding(s) 712. Furthermore, the digital molecular-phenomic embedding system 106 can utilize the molecular structural embedding(s) 712 to generate the molecular encoder-based molecular-phenomic embedding(s) 720 (in accordance with one or more implementations herein). Indeed, as shown in FIG. 7, the digital molecular-phenomic embedding system 106 can generate molecular inference(s) 722 for the input molecule 706 by utilizing the molecular encoder-based molecular-phenomic embedding(s) 720 generated for the molecule 706 (and the dose concentration 708).

For example, the digital molecular-phenomic embedding system 106 can utilize the molecular encoder-based molecular-phenomic embedding(s) 720 generated from the molecular structure(s) 702 (or the molecule 706) to select a phenomic image 728 (as the molecular inference(s) 722). In particular, the digital molecular-phenomic embedding system 106 can utilize a retrieval approach and/or other similarity measure-based approach (in accordance with one or more implementations herein) to identify one or more molecular-phenomic embeddings for phenomic images that match with (or are similar to) the molecular encoder-based molecular-phenomic embedding(s) 720 of the molecular structure(s) 702 (or the molecule 706). Moreover, the digital molecular-phenomic embedding system 106 can associate, tag, or display the selected phenomic images based on the similarity distances in a shared feature space. Indeed, in some cases, the digital molecular-phenomic embedding system 106 queries a library of phenomic images (e.g., a library of phenotypic experiment media data) with mapped (or assigned) molecular-phenomic embeddings to select one or more phenomic images for the molecular structure(s) 702 (or the molecule 706) (utilizing a distance comparison in the shared feature space). In particular, the digital molecular-phenomic embedding system 106 can select one or more phenomic images (as described above) to indicate a predicted phenotypic impact (e.g., as displayed in the phenomic images) for the molecular structure(s) 702 (or the molecule 706).

In some instances, the digital molecular-phenomic embedding system 106 can utilize the molecular encoder-based molecular-phenomic embedding(s) 720 generated from the molecular structure(s) 702 (or the molecule 706) to generate the phenomic image 728 (as the molecular inference(s) 722). For example, the digital molecular-phenomic embedding system 106 can utilize the molecular encoder-based molecular-phenomic embedding(s) 720 determined for the molecular structure(s) 702 (or the molecule 706) with an image generative model (e.g., a diffusion neural network, a generative adversarial network) to generate a phenomic image (or other microscopy representation) depicting a cellular perturbation (e.g., a perturbation caused by the molecular structure(s) 702 and/or the molecule 706). For example, the digital molecular-phenomic embedding system 106 can utilize an image generative model trained to generate phenomic images depicting a cellular perturbation that is likely for the molecular-phenomic embedding (e.g., by decoding the molecular-phenomic embedding) corresponding to the input molecular structure(s) 702 (or the molecule 706).

In one or more implementations, the digital molecular-phenomic embedding system 106 can utilize the molecular encoder-based molecular-phenomic embedding(s) 720 generated from the molecular structure(s) 702 (or the molecule 706) to select a molecule 724 (as the molecular inference(s) 722). For example, the digital molecular-phenomic embedding system 106 can utilize a retrieval approach and/or other similarity measure-based approach (in accordance with one or more implementations herein) to identify one or more molecular-phenomic embeddings for one or more additional molecules (or molecular structures) similar to (or matching with) the molecular encoder-based molecular-phenomic embedding(s) 720 of the molecular structure(s) 702 (or the molecule 706). Moreover, the digital molecular-phenomic embedding system 106 can associate, tag, or display the selected one or more additional molecules (or molecular structures) based on the similarity distance (in a shared feature space).

In some cases, the digital molecular-phenomic embedding system 106 queries a library of molecular structures (e.g., a molecule compound library) with mapped (or assigned) molecular-phenomic embeddings (generated as described above) to select one or more molecular structures for the molecular structure(s) 702 (or the molecule 706) (e.g., utilizing a distance comparison in a shared feature space). In particular, the digital molecular-phenomic embedding system 106 can select one or more molecular structures (as described above) as molecules that match (or are predicted to have similar phenotypic impacts as) the molecular structure(s) 702 (or the molecule 706).

As an example, with reference to FIG. 7, the digital molecular-phenomic embedding system 106 can utilize molecular structure(s) 702 as a library of molecular structures (e.g., candidate molecular structures). Furthermore, upon receiving a query for matching molecules with the input molecule 706, the digital molecular-phenomic embedding system 106 can utilize the molecular encoder-based molecular-phenomic embedding(s) 720 for the molecule 706 and the one or more (candidate) molecular structure(s) 702 to identify the matching molecule 724. Indeed, the digital molecular-phenomic embedding system 106 can identify a candidate molecule from the molecular structure(s) 702 that corresponds to a molecular-phenomic embedding with a similarity distance to the molecular-phenomic embedding of the molecule 706 that satisfies a threshold similarity distance to identify the molecule 724. In some cases, the digital molecular-phenomic embedding system 106 utilizes a threshold retrieval percentage to select one or more candidate molecules from the molecular structure(s) 702 for the molecule 706 to identify the molecule 724 (e.g., a top K % retrieval as described above with reference to FIG. 6).

In addition, the digital molecular-phenomic embedding system 106 can also utilize the molecular encoder-based molecular-phenomic embedding(s) 720 generated from the molecular structure(s) 702 (or the molecule 706) to select the molecule 724 with a molecule dose concentration 726 (as the molecular inference(s) 722). For example, the digital molecular-phenomic embedding system 106 can utilize a retrieval approach and/or other similarity measure-based approach (in accordance with one or more implementations herein) to identify one or more molecular-phenomic embeddings for one or more additional molecules (or molecular structures) similar to (or that match with) the molecular encoder-based molecular-phenomic embedding(s) 720 of the molecular structure(s) 702 with dose concentration 704 (or the molecule 706 with dose concentration 708). Moreover, the digital molecular-phenomic embedding system 106 can associate, tag, or display the selected one or more additional molecules (or molecular structures) based on a similarity distance (in a shared feature space). For instance, the digital molecular-phenomic embedding system 106 can determine similarity distances between molecular-phenomic embeddings of molecules with specific dose concentrations to select candidate molecular structures with particular dose concentrations (as a match to an input molecule with a dose concentration). In some cases, the digital molecular-phenomic embedding system 106 can identify additional molecules with different dose concentrations as a match to a molecule with a particular dose concentration (indicating that the molecules are predicted to possess similar phenotypic impacts with different dose concentration levels). Indeed, the digital molecular-phenomic embedding system 106 can encode dose concentrations as part of the molecular-phenomic embedding(s) 720 and utilize the dose concentrations to query (or select) matching (or similar) molecules with a specific dose concentration in accordance with one or more implementations herein.

In some cases, the digital molecular-phenomic embedding system 106 can utilize different molecule dose concentrations corresponding to the molecule 724 to generate a (graded) response curve for the molecule 724 to a target (e.g., a target perturbation and/or phenomic image perturbation). Indeed, the digital molecular-phenomic embedding system 106 can generate a response curve that maps a responsiveness to a target in terms of varying dose concentrations. In one or more implementations, the digital molecular-phenomic embedding system 106 utilizes the response curves to identify an effective concentration for a molecule (e.g., a half maximal effective concentration (EC50) or other maximal effective concentration) from the dose concentrations.

In some instances, the digital molecular-phenomic embedding system 106 can utilize the molecular encoder-based molecular-phenomic embedding(s) 720 generated from the molecular structure(s) 702 (or the molecule 706) to generate the molecule 724 (e.g., with a molecule dose concentration 726) as the molecular inference(s) 722. For example, the digital molecular-phenomic embedding system 106 can utilize the molecular encoder-based molecular-phenomic embedding(s) 720 determined for the molecular structure(s) 702 (or the molecule 706) with a molecular structure generative model (e.g., a generative flow network, a generative adversarial network) to generate a molecular structure predicted to be similar to and/or a variation of the molecular structure(s) 702 and/or the molecule 706. In some cases, the digital molecular-phenomic embedding system 106 can utilize the molecular encoder-based molecular-phenomic embedding(s) 720 with a molecular structure generative model to generate a novel molecular structure predicted to have a similar phenotypic impact as the molecular structure(s) 702 (or the molecule 706) (e.g., with dose concentrations). For example, the digital molecular-phenomic embedding system 106 can utilize a molecular structure generative model trained to generate molecule structures that is predicted to represent the molecular-phenomic embedding (e.g., by decoding the molecular-phenomic embedding) corresponding to the input molecular structure(s) 702 (or the molecule 706).

In some cases, as shown in FIG. 7, the digital molecular-phenomic embedding system 106 can utilize the molecular encoder-based molecular-phenomic embedding(s) 720 to generate a comparison 730 as the molecular inference(s) 722. For example, the digital molecular-phenomic embedding system 106 can utilize the molecular-phenomic embedding(s) 720 to generate the comparisons 730 as biological relationship data (e.g., for a tech-bio exploration system 1304 as described in FIG. 13) that maps relationships between molecular compounds, phenotypic experiments (via phenomic images and/or other microscopy representations), and/or for various tech-bio exploration tools. As an example, the digital molecular-phenomic embedding system 106 can, as the comparisons 730, generate perturbation heatmaps from the molecular encoder-based molecular-phenomic embedding(s) 720 as described in UTILIZING MACHINE LEARNING MODELS TO SYNTHESIZE PERTURBATION DATA TO GENERATE PERTURBATION HEATMAP GRAPHICAL USER INTERFACES, U.S. patent application Ser. No. 18/526,707, filed Dec. 1, 2023 (hereinafter "US application No. '707").

In addition, as shown in FIG. 7, the digital molecular-phenomic embedding system 106 can utilize molecular encoder-based molecular-phenomic embedding(s) 720 to determine a molecule activity classification 732 as the molecular inference(s) 722. For example, the digital molecular-phenomic embedding system 106 can identify one or more phenomic images corresponding to the molecular structure(s) 702 (or the molecule 706). Moreover, the digital molecular-phenomic embedding system 106 can utilize phenomic image embeddings from the identified one or more phenomic images to determine activity or inactivity by determining, via a null distribution of phenomic embeddings, that a particular molecule results in non-distinct (or distinct) phenomic image embeddings (as described above). Based on the digital molecular-phenomic embedding system 106 determining that the molecular structure(s) 702 (or the molecule 706) corresponds to non-distinct phenomic image embeddings, the digital molecular-phenomic embedding system 106 can determine the molecule activity classification 732 indicating the molecular structure(s) 702 (or the molecule 706) as inactive.

Moreover, the digital molecular-phenomic embedding system 106 can utilize molecular-phenomic embeddings to train or finetune a variety of biological activity prediction models. For instance, the digital molecular-phenomic embedding system 106 can utilize molecular-phenomic embeddings (generated in accordance with one or more implementations herein) as an input to a variety of biological activity prediction models. As an example, the digital molecular-phenomic embedding system 106 can utilize the molecular-phenomic embedding as a fingerprint to finetune a biological activity prediction model as described in U.S. patent application Ser. No. 18/750,813.

Additionally, the digital molecular-phenomic embedding system 106 can utilize a molecular-phenomic embedding (generated in accordance with one or more implementations herein) to determine a mechanism-of-action for the molecular structure(s) 702 (or the molecule 706). For instance, the digital molecular-phenomic embedding system 106 can identify a phenomic image (or phenomic image embedding) corresponding to the molecular-phenomic embedding and identify a mechanism-of-action corresponding to the phenomic image (or phenomic image embedding). In some instances, the digital molecular-phenomic embedding system 106 utilizes the molecular-phenomic embeddings as microscopy representation embeddings to determine mechanism-of actions as described in GENERATING A MECHANISM OF ACTION REPRESENTATION FROM CELL REPRESENTATION EMBEDDINGS TO PREDICT A MECHANISM OF ACTION FOR A PERTURBATION, U.S. patent application Ser. No. 18/663,819, filed May 14, 2024, which is incorporated herein by reference in its entirety (hereinafter U.S. patent application Ser. No. 18/663,819).

Additionally, FIG. 8 illustrates the digital molecular-phenomic embedding system 106 determining (or generating) molecular inferences from molecular-phenomic embeddings in relation to a phenomic image. As shown in FIG. 8, the digital molecular-phenomic embedding system 106 utilizes phenomic image(s) 802 (e.g., from a library of phenomic images) with a phenomic image generative model 806 to generate phenomic image embedding(s) 808 to utilize with a vision encoder 812 (of a trained contrastive molecular-phenomic embedding model 810) to generate vision encoder-based molecular-phenomic embedding(s) 814 (in accordance with one or more implementations herein). As further shown in FIG. 8, the digital molecular-phenomic embedding system 106 utilizes the vision encoder-based molecular-phenomic embedding(s) 814 to generate a variety of molecular inference(s) 816.

Furthermore, in some instances, as shown in FIG. 8, the digital molecular-phenomic embedding system 106 can generate molecular inferences from a singular input phenomic image. For example, as shown in FIG. 8, the digital molecular-phenomic embedding system 106 can receive a phenomic image 804. Moreover, the digital molecular-phenomic embedding system 106 can utilize the phenomic image 804 with the phenomic image generative model 806 to generate the phenomic image embedding(s) 808. Moreover, the digital molecular-phenomic embedding system 106 can utilize the phenomic image embedding(s) 808 to generate the vision encoder-based molecular-phenomic embedding(s) 814 (in accordance with one or more implementations herein). Indeed, as shown in FIG. 8, the digital molecular-phenomic embedding system 106 can generate molecular inference(s) 816 for the input phenomic image 804 by utilizing the vision encoder-based molecular-phenomic embedding(s) 814 generated for the phenomic image 804.

In some cases, the digital molecular-phenomic embedding system 106 utilizes the vision encoder-based molecular-phenomic embedding(s) 814 to select a molecule 818 (e.g., with a molecule dose concentration 821) as the molecular inference(s) 816. For example, the digital molecular-phenomic embedding system 106 can utilize a retrieval approach and/or other similarity measure-based approach (in accordance with one or more implementations herein) to identify one or more molecular-phenomic embeddings for molecular structures (with dose concentrations) that match with (or are similar to) the vision encoder-based molecular-phenomic embedding(s) 814 of the phenomic image(s) 802 (or the phenomic image 804). Moreover, the digital molecular-phenomic embedding system 106 can associate, tag, or display the selected molecular structures (and dose concentrations) based on the similarity distance (in a shared feature space).

Indeed, in some cases, the digital molecular-phenomic embedding system 106 queries a library of molecular structures (e.g., a molecule compound library) with mapped (or assigned) molecular-phenomic embeddings to select one or more molecular structures (e.g., with dose concentrations) for the phenomic image(s) 802 (or the phenomic image 804) (utilizing a distance comparison with the vision encoder-based molecular-phenomic embedding(s) 814 in a shared feature space). In particular, the digital molecular-phenomic embedding system 106 can select one or more molecular structures (as described above) to a predicted molecular structure that is likely to produce a phenotypic impact as depicted in the phenomic image(s) 802 (or the phenomic image 804). As described above, in some cases, the digital molecular-phenomic embedding system 106 utilizes a threshold retrieval percentage to select one or more candidate molecular structures (with dose concentrations) corresponding to molecular-phenomic embeddings in comparison to a molecular-phenomic embedding of a phenomic image (e.g., a top K % retrieval as described above in reference to FIG. 6).

In one or more implementations, the digital molecular-phenomic embedding system 106 utilizes the vision encoder-based molecular-phenomic embedding(s) 814 generated from the phenomic image(s) 802 (or the phenomic image 804) to generate the molecule 818 (e.g., with the molecule dose concentration 821) as the molecular inference(s) 816. For example, the digital molecular-phenomic embedding system 106 can utilize the vision encoder-based molecular-phenomic embedding(s) 814 with a molecular structure generative model (or molecule generative model) (e.g., a generative flow network, a generative adversarial network) to generate a molecular structure predicted to have a phenotypic impact similar to the phenotypic impact depicted in the phenomic image(s) 802 (or the phenomic image 804).

In one or more instances, as shown in FIG. 8, the digital molecular-phenomic embedding system 106 can utilize the vision encoder-based molecular-phenomic embedding(s) 814 to select a phenomic image 820 (or other microscopy representation) (as the molecular inference(s) 816). For instance, the digital molecular-phenomic embedding system 106 can utilize a retrieval approach and/or other similarity measure-based approach (in accordance with one or more implementations herein) to identify one or more molecular-phenomic embeddings for one or more additional phenomic images (or other microscopy representations) similar to (or matching with) the vision encoder-based molecular-phenomic embedding(s) 814 of the phenomic image(s) 802 (or the phenomic image 804). Moreover, the digital molecular-phenomic embedding system 106 can associate, tag, or display the selected one or more additional phenomic images based on the similarity distance (in a shared feature space).

In one or more implementations, the digital molecular-phenomic embedding system 106 queries a library of phenomic images with mapped (or assigned) molecular-phenomic embeddings (generated as described above) to select one or more phenomic images for the phenomic image(s) 802 (or the phenomic image 804) (e.g., utilizing distance comparisons to the vision encoder-based molecular-phenomic embedding(s) 814 in a shared feature space). In particular, the digital molecular-phenomic embedding system 106 can select one or more phenomic images (as described above) as phenomic images that match (or are predicted to have a similar depicted phenotypic impact or cell perturbation as) the phenomic image(s) 802 (or the phenomic image 804).

As an example, with reference to FIG. 8, the digital molecular-phenomic embedding system 106 can utilize phenomic image(s) 802 as a library of phenomic images (e.g., candidate phenomic images). Additionally, based on receiving a query for matching phenomic images with the input phenomic image 804, the digital molecular-phenomic embedding system 106 can utilize the vision encoder-based molecular-phenomic embedding(s) 814 for the phenomic image(s) 802 (or the phenomic image 804) to identify the matching phenomic image 820. In particular, the digital molecular-phenomic embedding system 106 can identify a candidate phenomic image from the phenomic image(s) 802 that corresponds to a molecular-phenomic embedding with a similarity distance to the molecular-phenomic embedding of the phenomic image 804 that satisfies a threshold similarity distance to identify the phenomic image 820. In some implementations, the digital molecular-phenomic embedding system 106 utilizes a threshold retrieval percentage to select one or more candidate phenomic images from the phenomic image(s) 802 for the phenomic image 804 to identify the phenomic image 820 (e.g., a top K % retrieval as described above in reference to FIG. 6).

Moreover, the digital molecular-phenomic embedding system 106 can utilize the vision encoder-based molecular-phenomic embedding(s) 814 to generate the phenomic image 820 (as the molecular inference(s) 816). For example, the digital molecular-phenomic embedding system 106 can utilize the molecular-phenomic embedding(s) 814 determined for the phenomic image(s) 802 (or the phenomic image 804) with an image generative model (e.g., a diffusion neural network, a generative adversarial network) to generate a phenomic image (or other microscopy representation) depicting a cellular perturbation similar to the cellular perturbation depicted in the phenomic image(s) 802 (or the phenomic image 804). For example, the digital molecular-phenomic embedding system 106 can utilize an image generative model trained to generate phenomic images depicting a cellular perturbation that is likely represented in the molecular-phenomic embedding (e.g., by decoding the molecular-phenomic embedding) corresponding to the input phenomic image(s) 802 (or the phenomic image 804).

In addition, the digital molecular-phenomic embedding system 106 can utilize the vision encoder-based molecular-phenomic embedding(s) 814 to generate a comparison 822 as the molecular inference(s) 816. For instance, the digital molecular-phenomic embedding system 106 can utilize the vision encoder-based molecular-phenomic embedding(s) 814 to generate the comparison 822 as biological relationship data (e.g., for a tech-bio exploration system 1304 as described in FIG. 13) that maps relationships between molecular compounds, phenotypic experiments (via phenomic images and/or other microscopy representations), and/or for various tech-bio exploration tools (as described above). Indeed, as described above, the digital molecular-phenomic embedding system 106 can, as the comparison 822, generate perturbation heatmaps from the molecular-phenomic embedding(s) 814 as described in US application No. '707.

Moreover, the digital molecular-phenomic embedding system 106 can utilize the vision encoder-based molecular-phenomic embedding(s) 814 to train or finetune a variety of biological activity prediction models. For instance, the digital molecular-phenomic embedding system 106 can utilize molecular-phenomic embeddings (generated in accordance with one or more implementations herein) as an input to a variety of biological activity prediction models. As an example, the digital molecular-phenomic embedding system 106 can utilize the molecular-phenomic embedding(s) 814 to generate graphical user interfaces, phenomic image correction, and/or other tasks as described in U.S. patent application Ser. No. 18/545,399.

In addition, the digital molecular-phenomic embedding system 106 can utilize the vision encoder-based molecular-phenomic embedding(s) 814 to determine molecular activity classifications in accordance with one or more implementations herein. Moreover, the digital molecular-phenomic embedding system 106 can utilize the vision encoder-based molecular-phenomic embedding(s) 814 to determine mechanism-of-action predictions in accordance with one or more implementations herein (e.g., using the molecular-phenomic embedding(s) 814 as microscopy representation embeddings as described in U.S. patent application Ser. No. 18/663,819).

Experimenters utilized an implementation of a contrastive molecular-phenomic embedding model to assess phenomolecular retrieval in comparison to various existing baseline models and in ablation studies. As part of the experiments, the experimenters used a training dataset consisting of fluorescent microscopy images paired with molecular structures and concentrations (used as perturbants) to assess model phenomolecular retrieval capabilities on three datasets of escalating generalization complexity (e.g., unseen microscopy images and molecules, previously unseen phenomics experiments and molecules split by the corresponding molecular scaffold, and an open source dataset as described in M. M. Fay et al., Rxrx3: Phenomics Map of Biology, *Biorxiv*, pages 2023-02, 2023). Indeed, the experimenters considered a variety of modalities to evaluate their impacts (e.g., images of cells representing phenomic experiments, phenomic image embeddings in accordance with one or more implementations herein, fingerprints representing binary presence of molecular substructures, and molecular structural embeddings in accordance with one or more implementations herein).

Figure 9A:
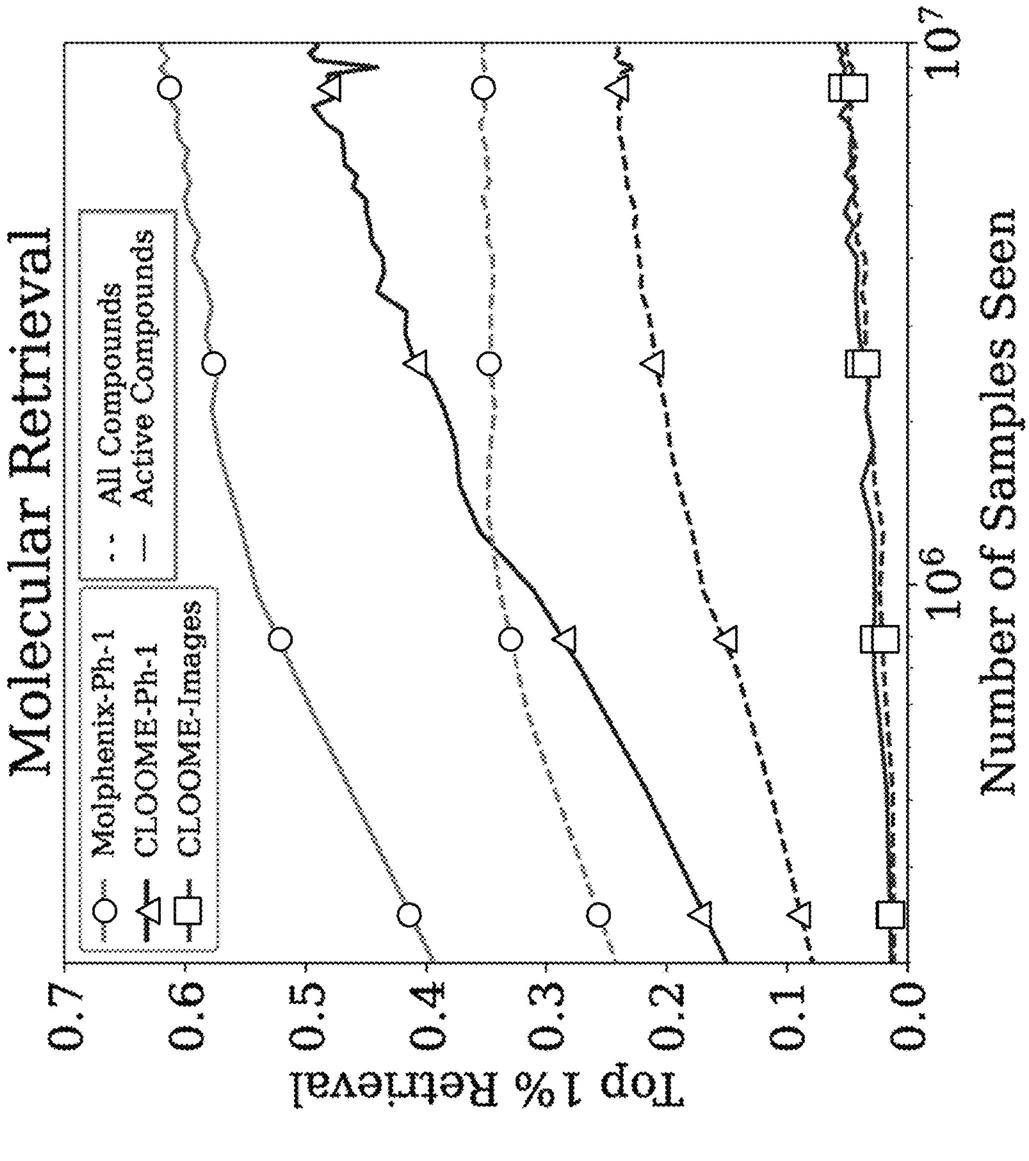

As a baseline model, the experimenters utilized an implementation of CLOOME as described in A. Sanchez-Fernandez et. al., CLOOME: Contrastive Learning Unlocks Bioimaging Databases for Queries with Chemical Structures, *Nature*, (2023). Furthermore, the experimenters carried out evaluations in two different settings: (1) cumulative concentrations, and (2) held-out concentrations, testing the models' ability to generalize to new molecular doses. For example, FIG. 9A illustrates recall accuracy on molecules and an active subset for CLOOME and an implementation of the digital molecular-phenomic embedding system (MolPhenix). As shown in FIG. 9A, utilizing phenomic image embeddings (Ph-1) (instead of phenomic images) significantly improves both active and all molecule retrieval. In addition, as shown in FIG. 9A, utilizing phenomic embeddings with the implementation of the digital molecular-phenomic embedding system (MolPhenix) further improves molecule retrieval. Indeed, in some instances, an implementation of the digital molecular-phenomic embedding system (MolPhenix) achieves an average improvement of eight times compared to CLOOME.

Furthermore, the experimenters conducted evaluations using various components (e.g., phenomic image embeddings (Ph-1), molecular structural embeddings (Mol-1), and/or explicit concentration in accordance with one or more implementations herein) on various contrastive learning methods (e.g., CLIP, Hopfield-CLIP, InfoLOOB, CLOOME, DCL, CWCL, SigLip) and an implementation of the digital molecular-phenomic embedding system (MolPhenix). The evaluations were conducted on unseen images, unseen images and unseen molecules, and unseen datasets (for zero-shot retrieval). Furthermore, the evaluations were conducted for cumulative concentrations for active molecules, for held-out concentration for active molecules, for cumulative concentrations for active and inactive molecules, and for held-out concentrations for active and inactive molecules. Indeed, the experimenters collected recall accuracy for a top-1% and top-5% retrieval (using the above-mentioned approaches). From the conducted evaluations, in many cases, the implementation of the digital molecular-phenomic embedding system (S2L) resulted in an improved performance in recall accuracies.

As an example, FIG. 9B illustrates recall accuracy results for top-1% and top-5% retrieval from evaluations conducted for cumulative concentrations for active molecules. As shown in the table of FIG. 9B, the implementation of the digital molecular-phenomic embedding system (MolPhenix) resulted in a highest recall accuracy performance across a majority of circumstances (as denoted by highlight). Moreover, with reference to FIG. 9B, bold entries denote best performance when the loss function is fixed.

As further shown in Table 1 (below), an implementation of the digital molecular-phenomic embedding system (MolPhenix) (using phenomic image embeddings and molecular structural embeddings in accordance with one or more implementations herein) results in an improvement in accuracy retrieval compared to CLOOME (using images and phenomic image embeddings) for a variety of sample data (e.g., active molecules, all molecules, unseen images, unseen images and molecules, unseen datasets (zero-shot)).

TABLE 1

| | | Active Molecules | | | All Molecules | | |
|---|---|---|---|---|---|---|---|
| Method | Modality | Unseen Im. | Unseen Im. + Mol. | Unseen Dataset | Unseen Im. | Unseen Im. + Mol. | Unseen Dataset |
| CLOOME | Images & Muli-FPS | .0756 ± .0042 | .0787 ± .0065 | .0528 ± .0057 | .0547 ± .0028 | .0661 ± .0020 | .0223 ± .0014 |
| CLOOME | Ph-1 & Multi-FPS | .4659 ± .0042 | .5057 ± .0014 | .2065 ± .0146 | .3009 ± .0053 | .2474 ± .0013 | .1337 ± .0045 |
| MolPhenix | Ph-1 & Mol-1 | **.9689 ± .0017** | **.7733 ± .0036** | **.5860 ± .0082** | **.5583 ± .0007** | **.3824 ± .0016** | **.2809 ± .0060** |

Furthermore, Table 2 (below) illustrates a top-1% recall accuracy of an implementation of the digital molecular-phenomic embedding system in comparison to several baseline models while omitting explicit dose concentrations. Indeed, as shown in Table 2, the experimenters evaluated the performance of the implementation of the digital molecular-phenomic embedding system utilizing an inter-sample similarity aware loss (S2L) in comparison to various baseline losses, such as InfoLOOB (as described in B. Poole et. al., On Variational Bounds of Mutual Information, International Conference on Machine Learning, pages 5171-5180, PMLR (2019)), CLOOME, CWCL (as described in R. S. Srinivasa, et. al., CWCL: Cross Modal Transfer with Continuously Weighted Contrastive Loss, Advances in Neural Information Processing System, 36 (2023)), and SigLip (as described in X. Zhai et. al., Sigmoid Loss for Language Image Pre-Training, Proceedings of the IEEE/CVF International Conference on Computer Vision, pages 11975-11986 (2023)). As illustrated in Table 2, the implementation of the digital molecular-phenomic embedding system (S2L) resulted in an improvement in retrieval rates.

TABLE 2

| Loss | Active Molecules: Unseen Im. | Active Molecules: Unseen Im. + Mol. | Active Molecules: Unseen Dataset | All Molecules: Unseen Im. | All Molecules: Unseen Im. + Mol. | All Molecules: Unseen Dataset |
|---|---|---|---|---|---|---|
| InfoLOOB | .3351 ± .0011 | .4206 ± .0031 | .1563 ± .0028 | .1746 ± .0003 | .1860 ± .0029 | .0745 ± .0019 |
| CLOOME | .3572 ± .0026 | .4348 ± .0039 | .1658 ± .0063 | .1968 ± .0029 | .2005 ± .0026 | .0911 ± .0022 |
| CWCL | .7091 ± .0045 | .6529 ± .0020 | .3556 ± .0094 | .3635 ± .0064 | .2696 ± .0019 | .1526 ± .0058 |
| SigLip | .7763 ± .0045 | .6401 ± .0065 | .3396 ± .0042 | .3729 ± .0039 | .2544 ± .0014 | .1470 ± .0038 |
| S2L | **.9097 ± .0020** | **.6759 ± .0012** | **.4181 ± .0012** | **.4688 ± .0009** | **.2852 ± .0001** | **.1838 ± .0007** |

Furthermore, Table 3 (below) illustrates a top-1% recall accuracy across different concentration encoding choices using various implementations of the digital molecular-phenomic embedding system (e.g., explicitly encoding molecular concentration with one-hot, logarithm, and sigmoid-based encodings. As illustrated in Table 3, utilizing explicit and implicit dose concentration encoding with an implementation of the digital molecular-phenomic embedding system resulted in an improvement in retrieval rates.

TABLE 3

| Implicit | Explicit | Active Molecules: Unseen Im. | Active Molecules: Unseen Im. + Mol. | Active Molecules: Unseen Dataset | All Molecules: Unseen Im. | All Molecules: Unseen Im. + Mol. | All Molecules: Unseen Dataset |
|---|---|---|---|---|---|---|---|
| No | No | .7350 ± .0071 | .6509 ± .0104 | .3333 ± .0004 | .3610 ± .0025 | .2668 ± .0034 | .1532 ± .0007 |
| Yes | No | .9097 ± .0020 | .6759 ± .0012 | .4181 ± .0012 | .4688 ± .0009 | .2852 ± .0001 | .1838 ± .0007 |
| Yes | sigmoid | .9423 ± .0011 | .7155 ± .0016 | .4573 ± .0022 | .5071 ± .0024 | .3441 ± .0026 | .2144 ± .0026 |
| Yes | logarithm | .9426 ± .0066 | .7451 ± .0050 | .4727 ± .0056 | .5183 ± .0027 | .3700 ± .0036 | .2275 ± .0032 |
| Yes | one-hot | **.9430 ± .0029** | **.7490 ± .0052** | **.4850 ± .0020** | **.5433 ± .0030** | **.3819 ± .0032** | **.2384 ± .0049** |

Additionally, experimenters evaluated impacts of utilizing an implementation of the digital molecular-phenomic embedding system with various training batch sizes and model sizes. Increasing batch sizes resulted in an improvement in performance. Furthermore, increasing model size also resulted in an improvement in performance. This improvement in performance indicates scalability of the model implementation of digital molecular-phenomic embedding system.

Figure 10:
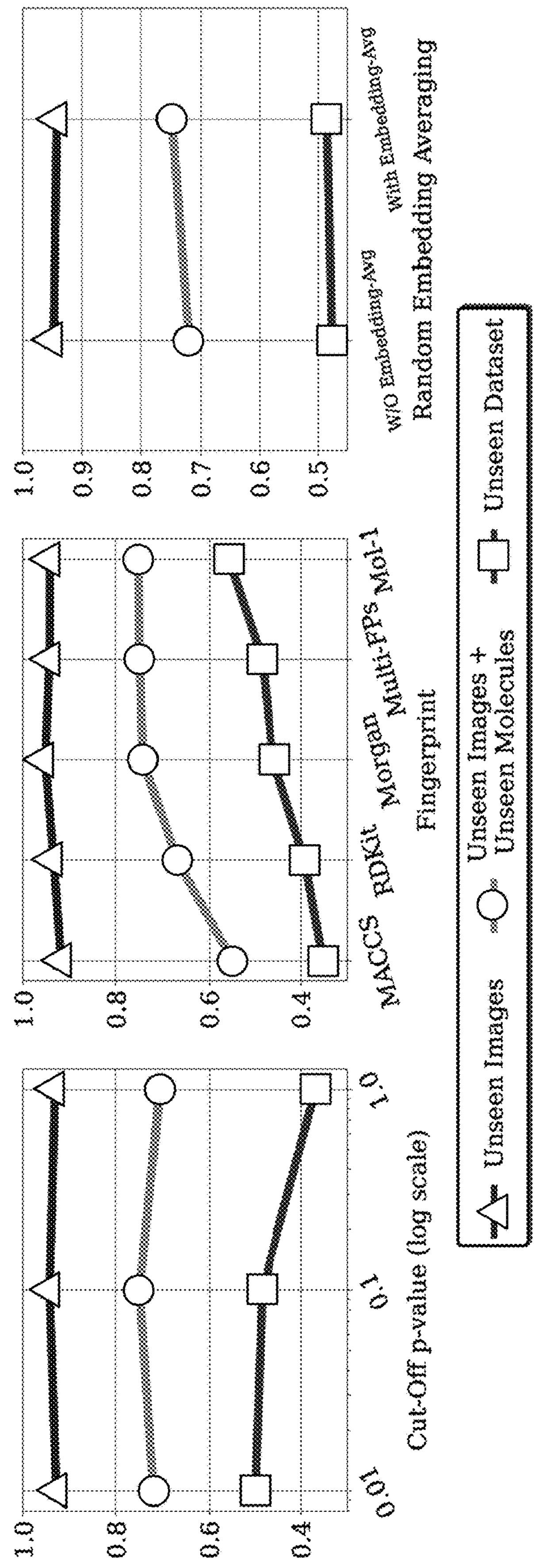

Furthermore, the experimenters conducted ablation studies with various implementations of the digital molecular-phenomic embedding system utilizing varying cutoff p values (for molecular activity), molecular structural embedding types, and phenomic image embedding averaging. For instance, the experimenters evaluated implementations of the digital molecular-phenomic embedding system utilizing molecular structural embedding types (e.g., molecular fingerprints), such as, RDKIT (as described in G. Landrum et al., RDKIT: A Software Suite for Cheminformatics, Computational Chemistry, and Predictive Modeling, Greg Landrum, 8 (31.10): 5281 (2013)), MACCS (K. Kuwahara et al., Analysis of the Effects of Related Fingerprints on Molecular Similarity using an Eigenvalue Entropy Approach, Journal of Cheminformatics, 13:1-12 (2021), MORGAN3 (D. Rogers et al., Extended-Connectivity Fingerprints, Journal of Chemical Information and Modeling, 50 (5): 742-754 (2010)), and molecular structural embeddings (Mol-1) (e.g., using graph based models in accordance with one or more implementations herein). Indeed, FIG. 10 illustrates recall accuracy across the above-mentioned components with an improvement in recall accuracy for several implementations of the digital molecular-phenomic embedding system.

Figure 11:
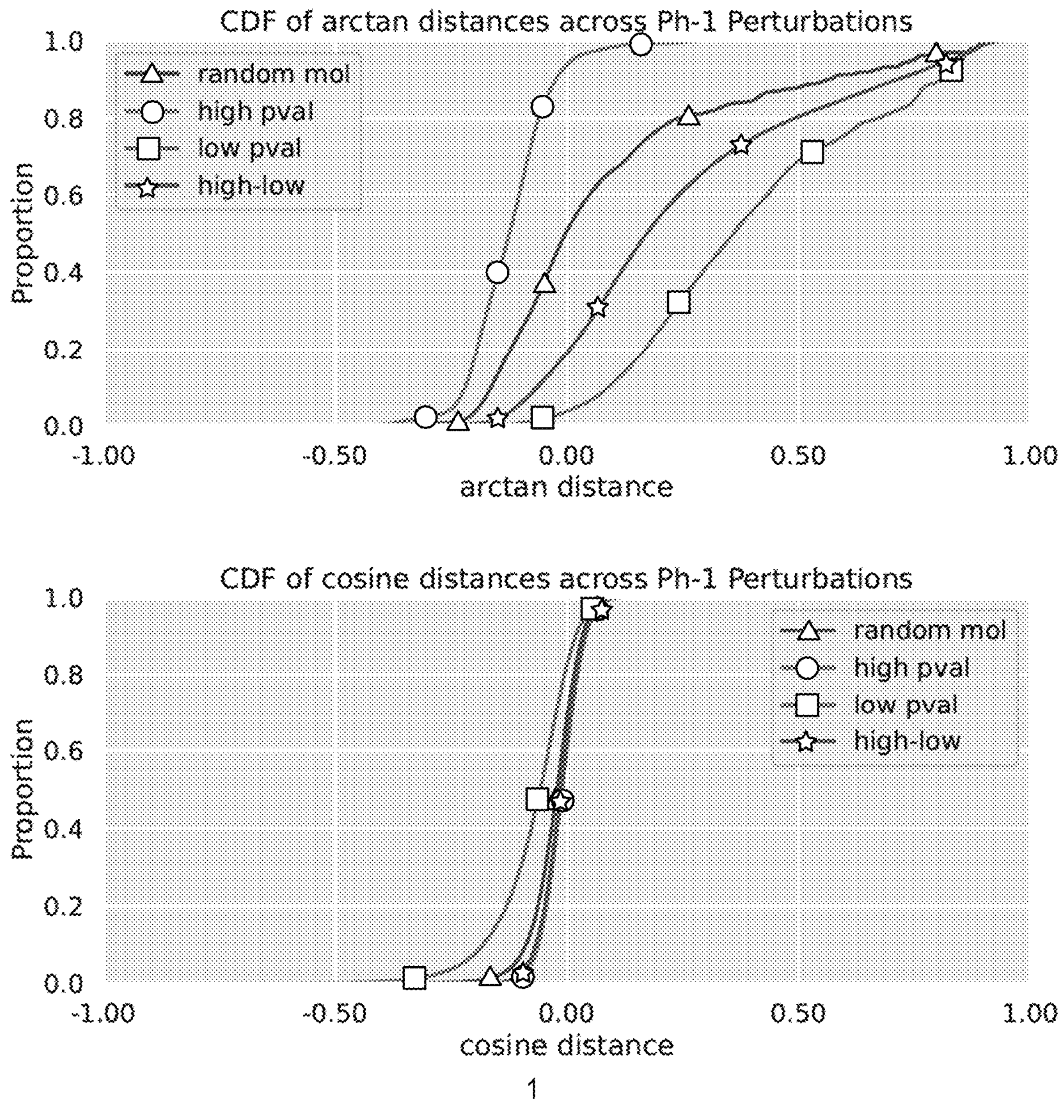

Additionally, the experimenters conducted comparisons between utilizing arctangent and cosine similarities in effectiveness of separating inactive molecules from other molecular pairs. For example, FIG. 11 illustrates plotted cumulative densities of distance metrics for cosine similarity and arctangent of L2 distance between embeddings for embedding distances between random molecules (random mol), distances between molecules with high p-values (high pval), distances between active molecules with low p-values (low pval), and distances between active and inactive molecules (high-low). As shown in FIG. 11, using arctangent similarities results in well separated curves which can improve model training informing to identify inactive molecules (and active molecules) (e.g., for S2L losses).

Figure 12:
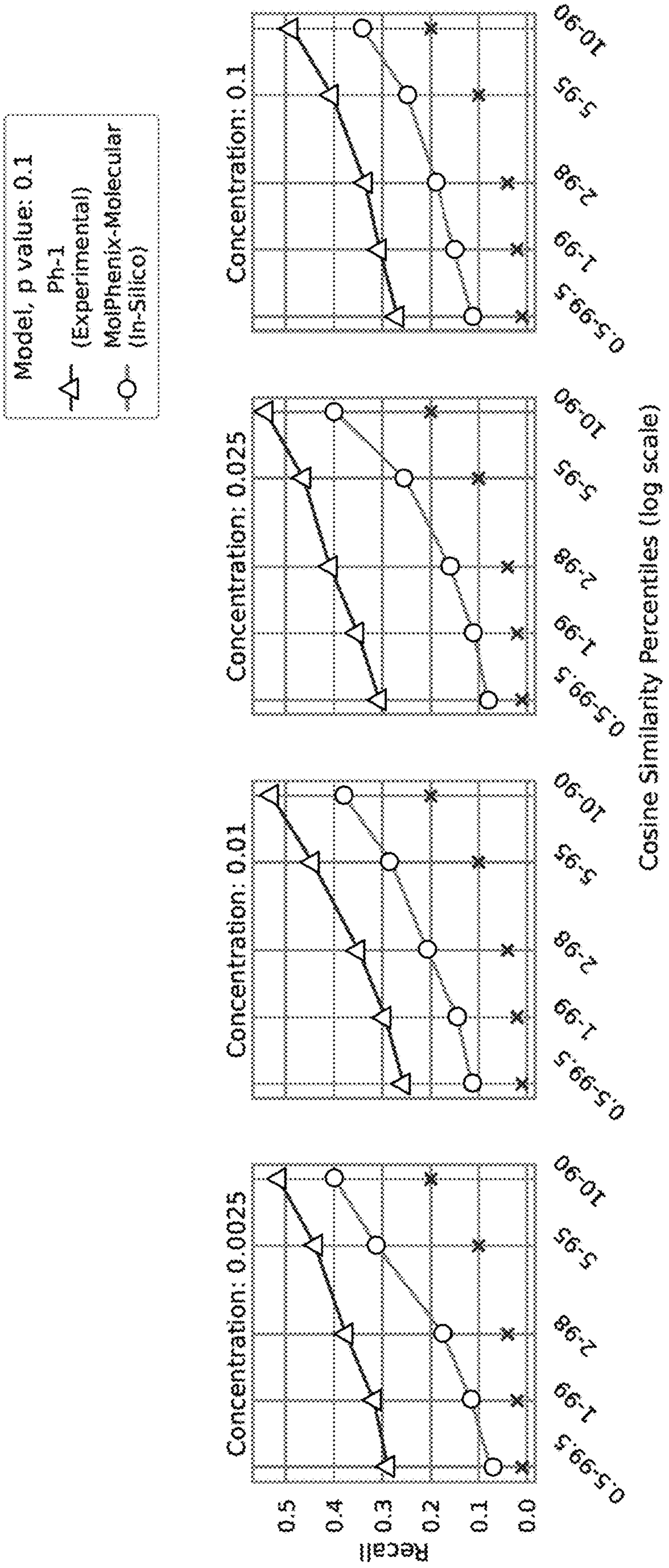

Furthermore, the experimenters conducted whether an implementation of the digital molecular-phenomic embedding system can be used to identify biological relationships without conducting the underlying experiments. In particular, the experimenters evaluated an implementation of the digital molecular-phenomic embedding system on a subset of ChEMBL with curated pairs of gene knockouts and molecular perturbants (as described in D. Mendez et. al., ChEMBL: Towards Direct Deposition of Bioassay Data, Nucleic Acids Research, 47(D1):D930-D940 (2019). Indeed, the experimenters used an implementation of the digital molecular-phenomic embedding system to embed phenomics experiments from gene knockouts using the vision encoder. Moreover, to perform in-silico screening, the experimenters used an implementation of the digital molecular-phenomic embedding system to embed the molecular structures associated with positive pairs using the molecular encoder. Moreover, the experimenters assessed the capability of the implementation of the digital molecular-phenomic embedding system in identifying known associations between gene knockouts and molecular structures using cosine similarities (across four concentrations) in comparison to a null distribution of pairs of gene knockouts and molecules with no annotated relationships). FIG. 12 illustrates total recall of recovered known interactions (from the above mentioned evaluation). Indeed, in FIG. 12, the charts illustrate a baseline recall (plotted as x's in the charts), MolPhenix-Molecular (In-Silico) indicates molecular encoding of chemical compounds and vision encoding for gene knockout phenomics experiments (from an implementation of the digital molecular-phenomic embedding system), and Ph-1 (Experimental) indicates phenomics embedding encoding of phenomic experiments for both the molecular perturbation (e.g., phenomic images) and gene knockouts from an implementation of the digital molecular-phenomic embedding system). As shown in FIG. 12, utilizing phenomics embedding encoding of phenomic experiments for both the molecular perturbation (e.g., phenomic images) and gene knockouts from an implementation of the digital molecular-phenomic embedding system) results in a recovery of a significant fraction of observed interactions demonstrating that the implementation of the digital molecular-phenomic embedding system is capable of recovering known interactions.

Figure 13:
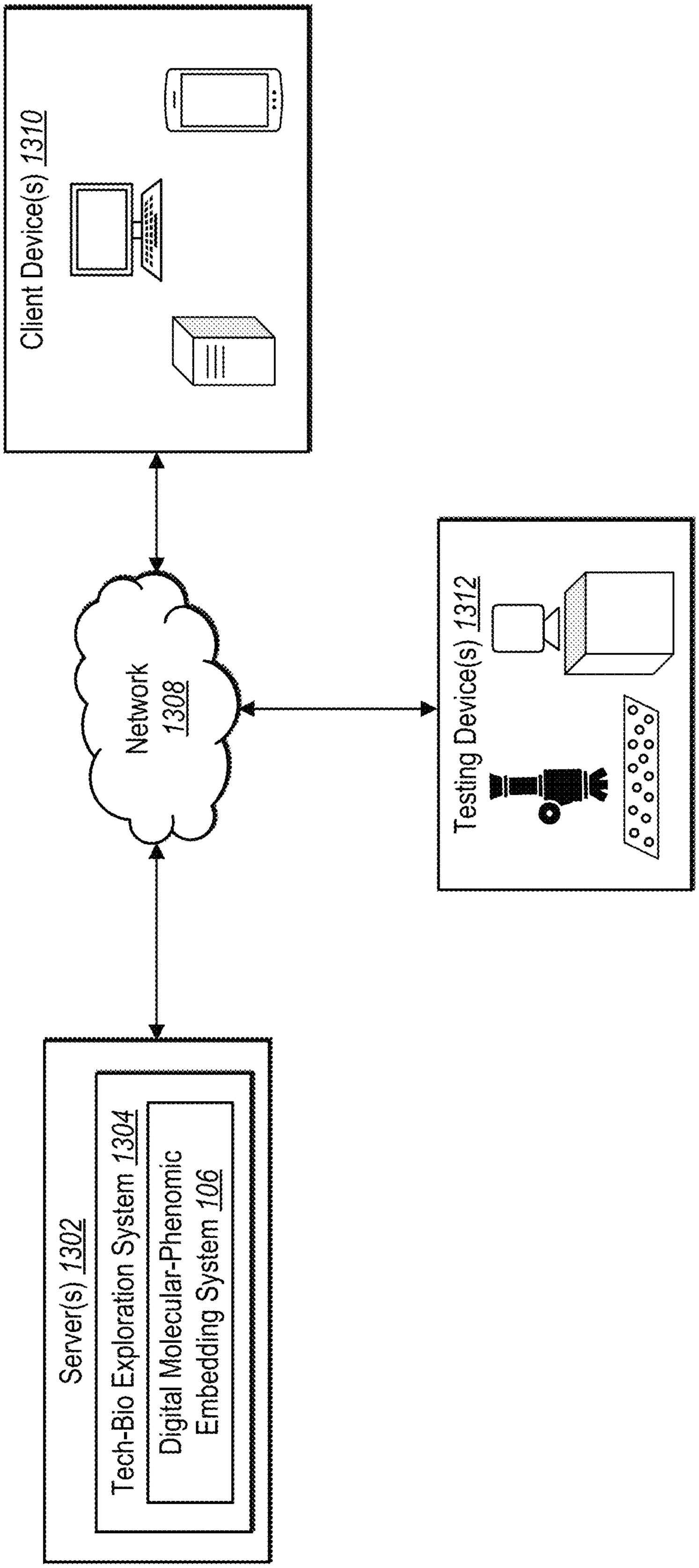
FIG. 13 illustrates a schematic diagram of a system environment in which a digital molecular-phenomic embedding system can operate in accordance with one or more implementations.

FIG. 13 illustrates a schematic diagram of a system environment in which the digital molecular-phenomic embedding system 106 can operate in accordance with one or more embodiments. As shown in FIG. 13, the environment includes server(s) 1302 (which includes a tech-bio exploration system 1304 and the digital molecular-phenomic embedding system 106), a network 1308, client device(s) 1310, and testing device(s) 1312. As further illustrated in FIG. 13, the various computing devices within the environment can communicate via the network 1308. Although FIG. 13 illustrates the digital molecular-phenomic embedding system 106 being implemented by a particular component and/or device within the environment, the digital molecular-phenomic embedding system 106 can be implemented, in whole or in part, by other computing devices and/or components in the environment (e.g., the client device(s) 1310). Additional description regarding the illustrated computing devices is provided with respect to FIG. 16 below.

As shown in FIG. 13, the server(s) 1302 can include the tech-bio exploration system 1304. In some embodiments, the tech-bio exploration system 1304 can determine, store, generate, and/or display tech-bio information including molecular compounds, phenomic images, gene knockouts, maps of biology, biology experiments from various sources, and/or machine learning tech-bio predictions. For instance, the tech-bio exploration system 1304 can analyze data signals corresponding to various treatments or interventions (e.g., compounds or biologics) and the corresponding relationships in genetics, proteomics, phenomics (i.e., cellular phenotypes), and invivomics (e.g., expressions or results within a living animal of in-vivo experiments involving chemical compounds). In one or more embodiments, the server(s) 1302 comprises a data server. In some implementations, the server(s) 1302 comprises a communication server or a web-hosting server.

For instance, the tech-bio exploration system 1304 can generate and access experimental results corresponding to gene sequences, protein shapes/folding, protein/compound interactions, phenotypes resulting from various interventions or perturbations (e.g., gene knockout sequences or compound treatments), and/or in-vivo experimentation on various treatments in living animals. By analyzing these signals (e.g., utilizing various machine learning models), the tech-bio exploration system 1304 can generate or determine a variety of predictions and inter-relationships for improving treatments/interventions.

To illustrate, the tech-bio exploration system 1304 can generate maps of biology indicating biological inter-relationships or similarities between these various input signals to discover potential new treatments. For example, the tech-bio exploration system 1304 can utilize machine learning and/or maps of biology to identify a similarity between a first gene associated with disease treatment and a second gene previously unassociated with the disease based on a similarity in resulting phenotypes from gene knockout experiments. The tech-bio exploration system 1304 can then identify new treatments based on the gene similarity (e.g., by targeting molecular compounds the impact the second gene). Similarly, the tech-bio exploration system 1304 can analyze signals from a variety of sources (e.g., protein interactions, molecular interactions, or in-vivo experiments) to predict efficacious treatments based on various levels of biological data.

The tech-bio exploration system 1304 can generate GUIs comprising dynamic user interface elements to convey tech-bio information and receive user input for intelligently exploring tech-bio information. Indeed, as mentioned above, the tech-bio exploration system 1304 can generate GUIs displaying different maps of biology that intuitively and efficiently express complex interactions between different biological systems for identifying improved treatment solutions. Furthermore, the tech-bio exploration system 1304 can also electronically communicate tech-bio information between various computing devices.

As shown in FIG. 13, the tech-bio exploration system 1304 can include a system that facilitates various models or algorithms for generating maps of biology (e.g., maps or visualizations illustrating similarities or relationships between genes, proteins, diseases, compounds, and/or treatments) and discovering new treatment options over one or more networks. For example, the tech-bio exploration system 1304 collects, manages, and transmits data across a variety of different entities, accounts, and devices. In some cases, the tech-bio exploration system 1304 is a network system that facilitates access to (and analysis of) tech-bio information within a centralized operating system. Indeed, the tech-bio exploration system 1304 can link data from different network-based research institutions to generate and analyze maps of biology.

As shown in FIG. 13, the tech-bio exploration system 1304 can include a system that comprises the digital molecular-phenomic embedding system 106 that can utilize a contrastive molecular-phenomic embedding model that learns joint latent space embeddings between molecular structures and phenomic images to generate molecular-phenomic embeddings that represent molecular impacts on cellular functions in accordance with one or more implementations herein. Furthermore, the tech-bio exploration system can utilize molecular-phenomic embeddings with (e.g., as inputs or as components) of a variety of tech-bio exploration tools, such as, but not limited to, bio-activity heatmap models as described in UTILIZING MACHINE LEARNING MODELS TO SYNTHESIZE PERTURBATION DATA TO GENERATE PERTURBATION HEATMAP GRAPHICAL USER INTERFACES, U.S. patent application Ser. No. 18/526,707, filed Dec. 1, 2023, ADMET prediction models and/or drug-likeness matching tools as described in UTILIZING COMPOUND-PROTEIN MACHINE LEARNING REPRESENTATIONS TO GENERATE BIOACTIVITY PREDICTIONS, U.S. patent application Ser. No. 18/505,728, filed Nov. 9, 2023, compound exploration program models as described in UTILIZING BIOLOGICAL MACHINE LEARNING REPRESENTATIONS AND A LANGUAGE MACHINE LEARNING MODEL FOR INITIATING COMPOUND EXPLORATION PROGRAMS, U.S. patent application Ser. No. 18/521,910, filed Nov. 28, 2023, digital maps of biology models as described in UTILIZING MACHINE LEARNING AND DIGITAL EMBEDDING PROCESSES TO GENERATE DIGITAL MAPS OF BIOLOGY AND USER INTERFACES FOR EVALUATING MAP EFFICACY, U.S. patent application Ser. No. 18/392,989, filed Dec. 21, 2023, and/or microscopy representation autoencoder models as described in UTILIZING MASKED AUTOENCODER GENERATIVE MODELS TO EXTRACT MICROSCOPY REPRESENTATION AUTOENCODER EMBEDDINGS, U.S. patent application Ser. No. 18/545,399, filed Dec. 19, 2023, each of which are incorporated by reference in their entirety herein.

As also illustrated in FIG. 13, the environment includes the client device(s) 1310. For example, the client device(s) 1310 may include, but is not limited to, a mobile device (e.g., smartphone, tablet) or other type of computing device, including those explained below with reference to FIG. 16. Additionally, the client device(s) 1310 can include a computing device associated with (and/or operated by) user accounts for the tech-bio exploration system 1304. Moreover, the environment can include various numbers of client devices that communicate and/or interact with the tech-bio exploration system 1304 and/or the digital molecular-phenomic embedding system 106.

Furthermore, in one or more implementations, the client device(s) 1310 includes a client application. The client application can include instructions that (upon execution) cause the client device(s) 1310 to perform various actions. For example, a user of a user account can interact with the client application on the client device(s) 1310 to initiate, generate, or access one or more molecular-phenomic embeddings and/or molecular inferences from molecular-phenomic embeddings (e.g., via prompts) in accordance with one or more implementations herein.

As further shown in FIG. 13, the environment includes the network 1308. As mentioned above, the network 1308 can enable communication between components of the environment. In one or more embodiments, the network 1308 may include a suitable network and may communicate using a various number of communication platforms and technologies suitable for transmitting data and/or communication signals, examples of which are described with reference to FIG. 16. Furthermore, although FIG. 13 illustrates computing devices communicating via the network 1308, the various components of the environment can communicate and/or interact via other methods (e.g., communicate directly).

In one or more implementations, the digital molecular-phenomic embedding system 106 generates and accesses molecular structures, phenomic images, molecular-phenomic embeddings, and/or models (in accordance with one or more implementations herein). As shown, in FIG. 13, the digital molecular-phenomic embedding system 106 can communicate with testing device(s) 1312 to utilize, obtain, analyze, generate, and/or store this information. For example, the tech-bio exploration system 1304 can interact with the testing device(s) 1312 that include intelligent robotic devices and camera devices for generating and capturing digital images of cellular phenotypes resulting from different perturbations (e.g., genetic knockouts or compound treatments of stem cells). Similarly, the testing device(s) 1312 can include camera devices and/or other sensors (e.g., heat or motion sensors) capturing real-time information from animals as part of in-vivo experimentation (e.g., biomarker data). The tech-bio exploration system 1304 can also interact with a variety of other testing device(s) such as devices for determining, generating, or extracting gene sequences or protein information.

FIGS. 1-13, the corresponding text, and the examples provide a number of different systems, computer-implemented methods, and non-transitory computer readable media for utilizing molecular-phenomic embeddings in accordance with one or more implementations herein. In addition to the foregoing, embodiments can also be described in terms of flowcharts comprising acts for accomplishing a particular result. For example, FIGS. 14 and 15 illustrate flowcharts of example sequences of acts in accordance with one or more embodiments.

Figure 14:
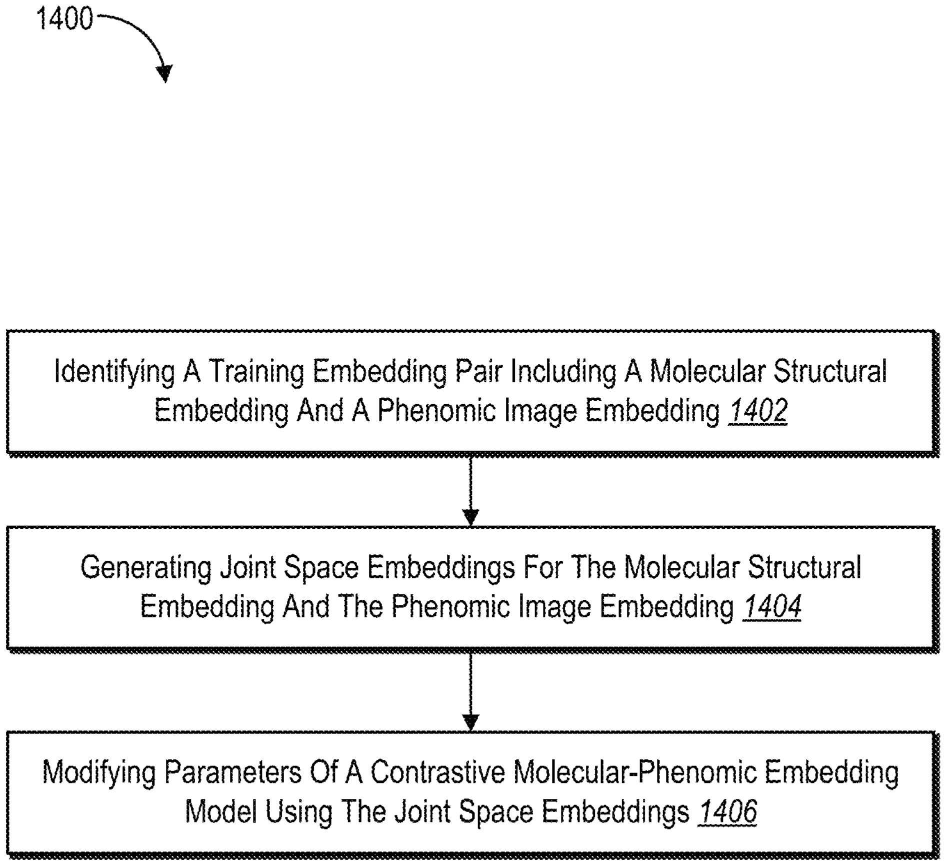
FIG. 14 illustrates an example series of acts for training a contrastive molecular-phenomic embedding model in accordance with one or more implementations.
Figure 15:
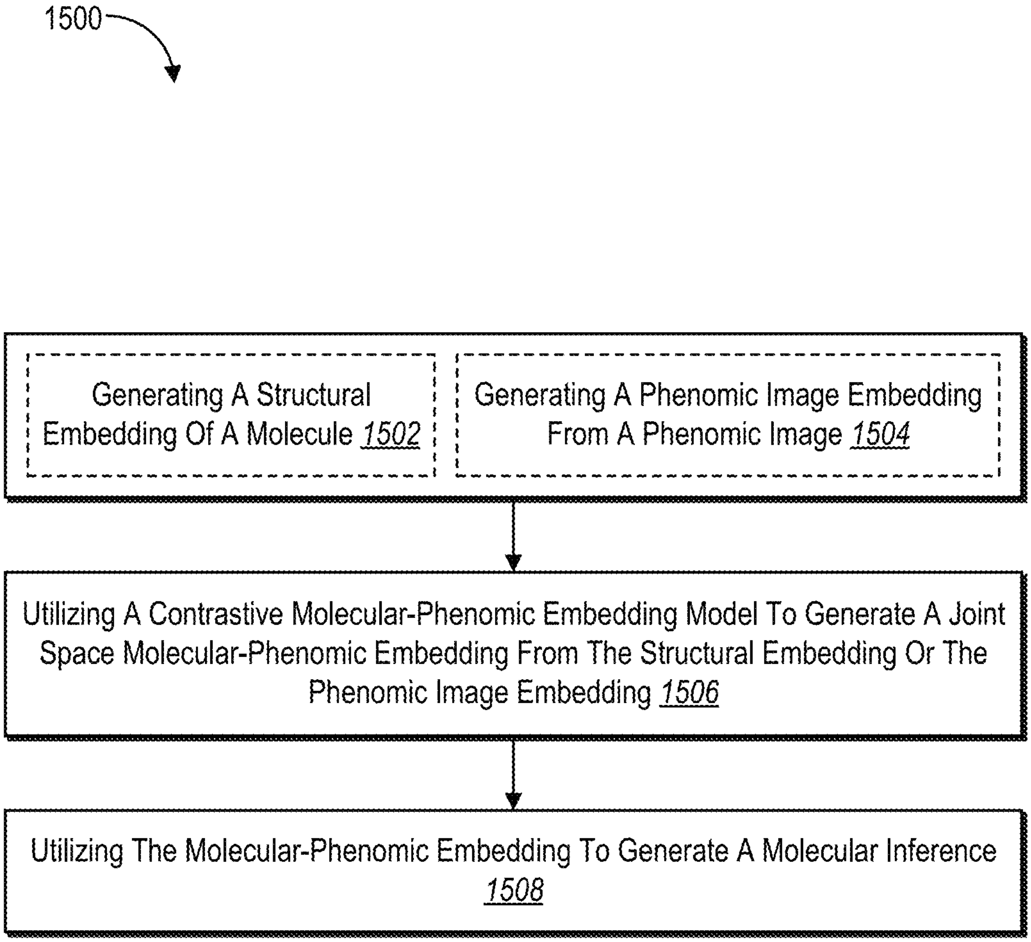
FIG. 15 illustrates an example series of acts for generating molecular inferences from molecular-phenomic embeddings in accordance with one or more implementations.

While FIGS. 14 and/or 15 illustrates acts according to some embodiments, alternative embodiments may omit, add to, reorder, combine, and/or modify any of the acts shown in FIGS. 14 and/or 15. The acts of FIGS. 14 and/or 15 can be performed as part of a (computer-implemented) method. Alternatively, a non-transitory computer readable medium can comprise instructions, that when executed by one or more processors, cause a computing device to perform the acts of FIGS. 14 and/or 15. In still further embodiments, a system can perform the acts of FIGS. 14 and/or 15. Additionally, the acts described herein may be repeated or performed in parallel with one another or in parallel with different instances of the same or other similar acts.

For instance, FIG. 14 illustrates an example series of acts for training a contrastive molecular-phenomic embedding model in accordance with one or more implementations. For example, as shown in FIG. 14, the series of acts 1400 can include an act 1402 of identifying a training embedding pair include a molecular structural embedding and a phenomic image embedding, an act 1404 of generating joint space embeddings for the molecular structural embedding and the phenomic image embedding, and an act 1406 of modifying parameters of a contrastive molecular-phenomic embedding model using the joint space embeddings.

In one or more instances, the series of acts 1400 can include identifying a training embedding pair comprising a molecular structural embedding of a molecule and a phenomic image embedding generated from applying a pre-trained embedding model to a phenomic image of a cell, generating, utilizing a contrastive molecular-phenomic embedding model, a first embedding from the phenomic image embedding, generating, utilizing the contrastive molecular-phenomic embedding model, a second embedding from the molecular structural embedding, and modifying parameters of the contrastive molecular-phenomic embedding model by comparing the first embedding and the second embedding.

Moreover, the series of acts 1400 can include generating the phenomic image embedding by utilizing a batch of phenomic image embeddings from applying the pre-trained embedding model to a plurality of phenomic images of the cell.

Additionally, the series of acts 1400 can include generating training embedding pairs for the contrastive molecular-phenomic embedding model by identifying an additional molecular structural embedding corresponding to an additional phenomic image embedding and/or filtering the additional molecular structural embedding as an inactive molecule by comparing the additional molecular structural embedding to a null distribution of phenomic image embeddings associated to one or more molecular structural embeddings.

In addition, the series of acts 1400 can include identifying the phenomic image embedding as a phenomic image autoencoder embedding generated from applying a masked autoencoder generative model to the phenomic image of the cell.

Furthermore, the series of acts 1400 can include modifying the parameters of the contrastive molecular-phenomic embedding model by determining a measure of contrastive loss from a similarity distance between the first embedding and the second embedding as a positive pair and/or utilizing the measure of contrastive loss to modify the parameters of the contrastive molecular-phenomic embedding model to increase a likelihood of positive pair retrieval from the contrastive molecular-phenomic embedding model. Additionally, the series of acts 1400 can include determining the measure of contrastive loss by utilizing an inter-sample similarity aware loss that weighs the measure of contrastive loss based on similarity measurements between the phenomic image embedding and additional phenomic image embeddings. In addition, the series of acts 1400 can include determining a measure of contrastive loss from a similarity distance between the first embedding and the second embedding as a positive pair utilizing an inter-sample similarity aware loss that weighs the measure of contrastive loss based on similarity measurements between the phenomic image embedding and additional phenomic image embeddings. Moreover, the series of acts 1400 can include determining the similarity measurements between the phenomic image embedding and additional phenomic image embeddings utilizing arctangents of similarity distances between the phenomic image embedding and additional phenomic image embeddings.

Additionally, the series of acts 1400 can include generating, utilizing the contrastive molecular-phenomic embedding model, the second embedding from the molecular structural embedding and a molecular concentration encoding corresponding to the molecular structural embedding. Moreover, the series of acts 1400 can include determining a first measure of contrastive loss between the first embedding and the second embedding corresponding to the molecular structural embedding with the molecular concentration encoding, determining a second measure of contrastive loss between a third embedding corresponding to an additional phenomic image embedding and a fourth embedding corresponding to the molecular structural embedding with an additional molecular concentration encoding, and/or utilizing the first measure of contrastive loss and the second measure of contrastive loss to modify the parameters of the contrastive molecular-phenomic embedding model.

Furthermore, the series of acts 1400 can include generating, utilizing a visual encoder of the contrastive molecular-phenomic embedding model, the first embedding from the phenomic image embedding. In addition, the series of acts 1400 can include generating, utilizing a molecular encoder of the contrastive molecular-phenomic embedding model, the second embedding from the molecular structural embedding.

Furthermore, FIG. 15 illustrates an example series of acts for generating molecular inferences from molecular-phenomic embeddings in accordance with one or more implementations. For instance, as shown in FIG. 15, the series of acts 1500 can include an act 1502 of generating a structural embedding of a molecule and/or an act 1504 of generating a phenomic image embedding from a phenomic image. Furthermore, as shown in FIG. 15, the series of acts 1500 can include an act 1506 of utilizing a contrastive molecular-phenomic embedding model to generate a joint space molecular-phenomic embedding from the structural embedding or the phenomic image embedding and an act 1508 of utilizing the molecular-phenomic embedding to generate a molecular inference.

For example, the series of acts 1500 can include generating, utilizing a structural embedding model (e.g., a neural network), a structural embedding of a molecule, generating, utilizing a structural encoder of a contrastive molecular-phenomic embedding model with the structural embedding, a molecular-phenomic embedding in a joint molecular-phenomic feature space, wherein the structural encoder is jointly trained with a vision encoder of the contrastive molecular-phenomic embedding model to map molecular structural embeddings and phenomic image autoencoder embeddings generated from a masked autoencoder generative model to the joint molecular-phenomic feature space, and utilizing the molecular-phenomic embedding to generate a molecular inference for the molecule.

Furthermore, in some cases, the series of acts 1500 include generating, utilizing a masked autoencoder generative model, a phenomic image embedding from a phenomic image of a perturbed cell, generating, from the phenomic image embedding utilizing a vision encoder of a contrastive molecular-phenomic embedding model, a molecular-phenomic embedding in a joint molecular-phenomic feature space, and utilizing the molecular-phenomic embedding to identify a molecule corresponding to the phenomic image of the perturbed cell.

In addition, the series of acts 1500 can include generating a concentration dose encoding for a concentration dose of the molecule, generating a combined concentration structural embedding by combining the concentration dose encoding and the structural embedding of the molecule, and/or generating the molecular-phenomic embedding by utilizing the combined concentration structural embedding with the structural encoder of the contrastive molecular-phenomic embedding model.

Furthermore, the series of acts 1500 can include generating the molecular inference for the molecule by selecting a phenomic image depicting a similar phenotypic impact in relation to the molecule from a comparison of the molecular-phenomic embedding to an additional molecular-phenomic embedding generated from a phenomic image embedding corresponding to the phenomic image.

In addition, the series of acts 1500 can include generating the molecular inference by utilizing the molecular-phenomic embedding with an image generative model to generate a phenomic image of a cell depicting a cell perturbation.

Moreover, the series of acts 1500 can include generating the molecular inference by selecting an additional molecule similar to the molecule based on a comparison between the molecular-phenomic embedding to an additional molecular-phenomic embedding generated from an additional structural embedding of the additional molecule.

Additionally, the series of acts 1500 can include generating the molecular inference by generating an activity classification for the molecule utilizing the molecular-phenomic embedding. Furthermore, the series of acts 1500 can include generating the activity classification by utilizing the molecular-phenomic embedding and a null distribution of embeddings generated from phenomic image autoencoder embeddings.

Moreover, the series of acts 1500 can include utilizing a contrastive molecular-phenomic embedding model that is trained to map molecular structural embeddings and phenomic image autoencoder embeddings to the joint molecular-phenomic feature space utilizing an inter-sample similarity aware loss that weighs a measure of contrastive loss based on similarity measurements between the phenomic image autoencoder embeddings.

Furthermore, the series of acts 1500 can include identifying the molecule corresponding to the phenomic image of the perturbed cell by comparing the molecular-phenomic embedding and an additional molecular-phenomic embedding associated with the molecule. For example, the additional molecular-phenomic embedding is generated in the joint molecular-phenomic feature space utilizing a structural encoder of the contrastive molecular-phenomic embedding model.

Additionally, the series of acts 1500 can include identifying the molecule and a concentration dose corresponding to the molecule for the phenomic image of the perturbed cell based on the molecular-phenomic embedding.

Moreover, the series of acts 1500 can include generating a molecular structure by utilizing the molecular-phenomic embedding with a molecular structure generative model.

In addition, the series of acts 1500 can include utilizing a contrastive molecular-phenomic embedding model that is trained to map molecular structural embeddings and phenomic image autoencoder embeddings to the joint molecular-phenomic feature space utilizing an inter-sample similarity aware loss that weighs a measure of contrastive loss based on similarity measurements between the phenomic image autoencoder embeddings.

Embodiments of the present disclosure may comprise or utilize a special purpose or general-purpose computer including computer hardware, such as, for example, one or more processors and system memory, as discussed in greater detail below. Implementations within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., a memory, etc.), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, implementations of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed by a processor, cause a general-purpose computer, special purpose computer, or special purpose processing device to perform a certain function or group of functions. In some implementations, computer-executable instructions are executed on a general-purpose computer to turn the general-purpose computer into a special purpose computer implementing elements of the disclosure. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multiprocessor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Implementations of the present disclosure can also be implemented in cloud computing environments. In this description, "cloud computing" is defined as a model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In this description and in the claims, a "cloud-computing environment" is an environment in which cloud computing is employed.

Figure 16:
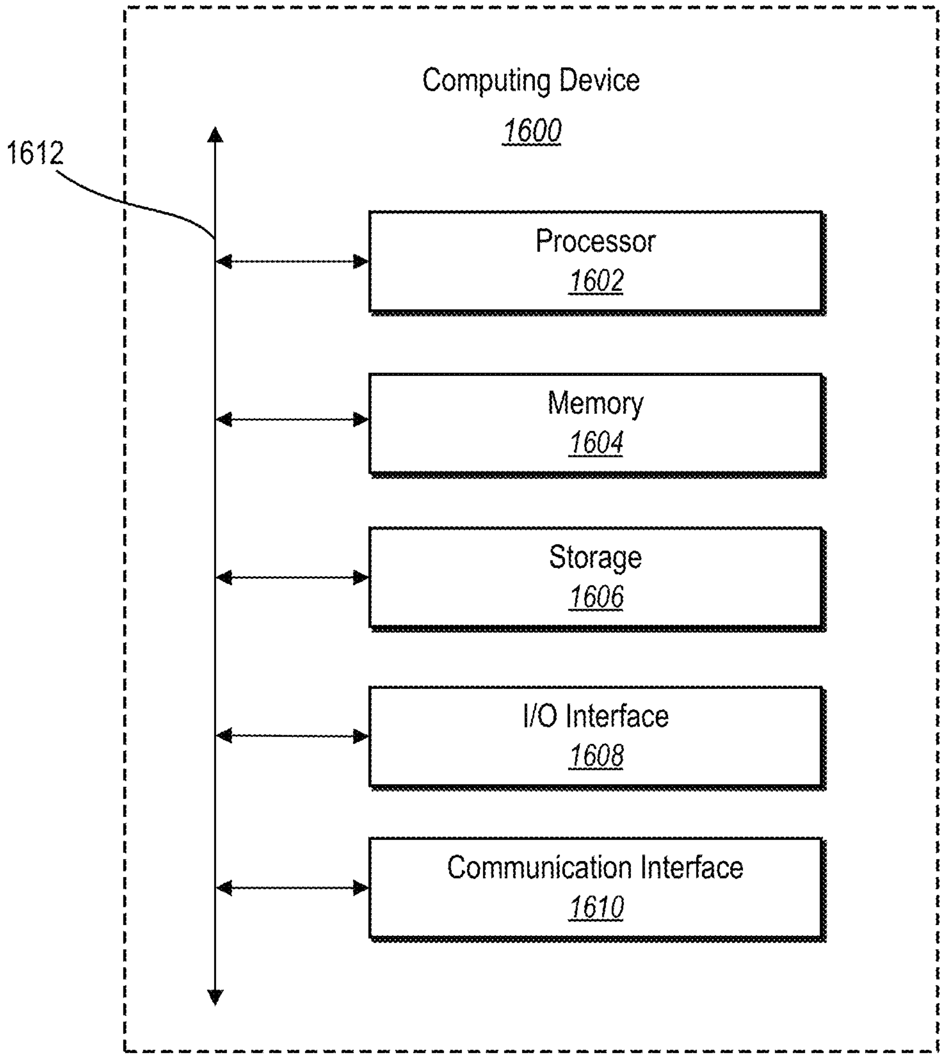
FIG. 16 illustrates a block diagram of an example computing device for implementing one or more embodiments of the present disclosure.

FIG. 16 illustrates a block diagram of exemplary computing device 1600 (e.g., the server(s) 1302 and/or the client device(s) 1310) that may be configured to perform one or more of the processes described above. One will appreciate that server(s) 1302 and/or the client device(s) 1310 may comprise one or more computing devices such as computing device 1600. As shown by FIG. 16, computing device 1600 can comprise processor 1602, memory 1604, storage device 1606, I/O interface 1608, and communication interface 1610, which may be communicatively coupled by way of communication infrastructure 1612. While an exemplary computing device 1600 is shown in FIG. 16, the components illustrated in FIG. 16 are not intended to be limiting. Additional or alternative components may be used in other implementations. Furthermore, in certain implementations, computing device 1600 can include fewer components than those shown in FIG. 16. Components of computing device 1600 shown in FIG. 16 will now be described in additional detail.

In particular implementations, processor 1602 includes hardware for executing instructions, such as those making up a computer program. As an example and not by way of limitation, to execute instructions, processor 1602 may retrieve (or fetch) the instructions from an internal register, an internal cache, memory 1604, or storage device 1606 and decode and execute them. In particular implementations, processor 1602 may include one or more internal caches for data, instructions, or addresses. As an example and not by way of limitation, processor 1602 may include one or more instruction caches, one or more data caches, and one or more translation lookaside buffers (TLBs). Instructions in the instruction caches may be copies of instructions in memory 1604 or storage device 1606.

Memory 1604 may be used for storing data, metadata, and programs for execution by the processor(s). Memory 1604 may include one or more of volatile and non-volatile memories, such as Random Access Memory ("RAM"), Read Only Memory ("ROM"), a solid state disk ("SSD"), Flash, Phase Change Memory ("PCM"), or other types of data storage. Memory 1604 may be internal or distributed memory.

Storage device 1606 includes storage for storing data or instructions. As an example and not by way of limitation, storage device 1606 can comprise a non-transitory storage medium described above. Storage device 1606 may include a hard disk drive (HDD), a floppy disk drive, flash memory, an optical disc, a magneto-optical disc, magnetic tape, or a Universal Serial Bus (USB) drive or a combination of two or more of these. Storage device 1606 may include removable or non-removable (or fixed) media, where appropriate. Storage device 1606 may be internal or external to computing device 1600. In particular implementations, storage device 1606 is non-volatile, solid-state memory. In other implementations, Storage device 1606 includes read-only memory (ROM). Where appropriate, this ROM may be a mask programmed ROM, programmable ROM (PROM), erasable PROM (EPROM), electrically erasable PROM (EEPROM), electrically alterable ROM (EAROM), or flash memory or a combination of two or more of these.

I/O interface 1608 allows a user to provide input to, receive output from, and otherwise transfer data to and receive data from computing device 1600. I/O interface 1608 may include a mouse, a keypad or a keyboard, a touch screen, a camera, an optical scanner, network interface, modem, other known I/O devices or a combination of such I/O interfaces. I/O interface 1608 may include one or more devices for presenting output to a user, including, but not limited to, a graphics engine, a display (e.g., a display screen), one or more output drivers (e.g., display drivers), one or more audio speakers, and one or more audio drivers. In certain implementations, I/O interface 1608 is configured to provide graphical data to a display for presentation to a user. The graphical data may be representative of one or more graphical user interfaces and/or any other graphical content as may serve a particular implementation.

Communication interface 1610 can include hardware, software, or both. In any event, communication interface 1610 can provide one or more interfaces for communication (such as, for example, packet-based communication) between computing device 1600 and one or more other computing devices or networks. As an example and not by way of limitation, communication interface 1610 may include a network interface controller (NIC) or network adapter for communicating with an Ethernet or other wire-based network or a wireless NIC (WNIC) or wireless adapter for communicating with a wireless network, such as a WI-FI.

Additionally or alternatively, communication interface 1610 may facilitate communications with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, communication interface 1610 may facilitate communications with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination thereof.

Additionally, communication interface 1610 may facilitate communications various communication protocols. Examples of communication protocols that may be used include, but are not limited to, data transmission media, communications devices, Transmission Control Protocol ("TCP"), Internet Protocol ("IP"), File Transfer Protocol ("FTP"), Telnet, Hypertext Transfer Protocol ("HTTP"), Hypertext Transfer Protocol Secure ("HTTPS"), Session Initiation Protocol ("SIP"), Simple Object Access Protocol ("SOAP"), Extensible Mark-up Language ("XML") and variations thereof, Simple Mail Transfer Protocol ("SMTP"), Real-Time Transport Protocol ("RTP"), User Datagram Protocol ("UDP"), Global System for Mobile Communications ("GSM") technologies, Code Division Multiple Access ("CDMA") technologies, Time Division Multiple Access ("TDMA") technologies, Short Message Service ("SMS"), Multimedia Message Service ("MMS"), radio frequency ("RF") signaling technologies, Long Term Evolution ("LTE") technologies, wireless communication technologies, in-band and out-of-band signaling technologies, and other suitable communications networks and technologies.

Communication infrastructure 1612 may include hardware, software, or both that couples components of computing device 1600 to each other. As an example and not by way of limitation, communication infrastructure 1612 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

In the foregoing specification, the invention has been described with reference to specific example embodiments thereof. Various embodiments and aspects of the invention(s) are described with reference to details discussed herein, and the accompanying drawings illustrate the various embodiments. The description above and drawings are illustrative of the invention and are not to be construed as limiting the invention. Numerous specific details are described to provide a thorough understanding of various embodiments of the present invention.

The present invention may be embodied in other specific forms without departing from its spirit or essential characteristics. The described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel to one another or in parallel to different instances of the same or similar steps/acts. The scope of the invention is, therefore, indicated by the appended claims rather than by the foregoing description. All changes that come within the meaning and range of equivalency of the claims are to be embraced within their scope.

What is claimed is:

1. A computer-implemented method comprising:

identifying a training embedding pair comprising a molecular structural embedding of a molecule and a phenomic image embedding generated from applying a pre-trained embedding model to a phenomic image of a cell;

generating, utilizing a contrastive molecular-phenomic embedding model, a first embedding from the phenomic image embedding;

generating, utilizing the contrastive molecular-phenomic embedding model, a second embedding from the molecular structural embedding; and modifying parameters of the contrastive molecular-phenomic embedding model by comparing the first embedding and the second embedding.

2. The computer-implemented method of claim 1, further comprising generating the phenomic image embedding by utilizing a batch of phenomic image embeddings from applying the pre-trained embedding model to a plurality of phenomic images of the cell.

3. The computer-implemented method of claim 1, further comprising generating training embedding pairs for the contrastive molecular-phenomic embedding model by:

identifying an additional molecular structural embedding corresponding to an additional phenomic image embedding; and filtering the additional molecular structural embedding as an inactive molecule by comparing the additional molecular structural embedding to a null distribution of phenomic image embeddings associated to one or more molecular structural embeddings.

4. The computer-implemented method of claim 1, further comprising modifying the parameters of the contrastive molecular-phenomic embedding model by:

determining a measure of contrastive loss from a similarity distance between the first embedding and the second embedding as a positive pair utilizing an inter-sample similarity aware loss that weighs the measure of contrastive loss based on similarity measurements between the phenomic image embedding and additional phenomic image embeddings; and utilizing the measure of contrastive loss to modify the parameters of the contrastive molecular-phenomic embedding model to increase a likelihood of positive pair retrieval from the contrastive molecular-phenomic embedding model.

5. The computer-implemented method of claim 1, further comprising identifying the phenomic image embedding as a phenomic image autoencoder embedding generated from applying a masked autoencoder generative model to the phenomic image of the cell.

6. The computer-implemented method of claim 4, further comprising determining the similarity measurements between the phenomic image embedding and additional phenomic image embeddings utilizing arctangents of similarity distances between the phenomic image embedding and additional phenomic image embeddings.

7. The computer-implemented method of claim 1, further comprising generating, utilizing the contrastive molecular-phenomic embedding model, the second embedding from the molecular structural embedding and a molecular concentration encoding corresponding to the molecular structural embedding.

8. The computer-implemented method of claim 7, further comprising:

determining a first measure of contrastive loss between the first embedding and the second embedding corresponding to the molecular structural embedding with the molecular concentration encoding;

determining a second measure of contrastive loss between a third embedding corresponding to an additional phenomic image embedding and a fourth embedding corresponding to the molecular structural embedding with an additional molecular concentration encoding; and utilizing the first measure of contrastive loss and the second measure of contrastive loss to modify the parameters of the contrastive molecular-phenomic embedding model.

9. The computer-implemented method of claim 1, further comprising:

generating, utilizing a visual encoder of the contrastive molecular-phenomic embedding model, the first embedding from the phenomic image embedding; and generating, utilizing a molecular encoder of the contrastive molecular-phenomic embedding model, the second embedding from the molecular structural embedding.

10. A system comprising:

at least one processor; and at least one non-transitory computer-readable storage medium storing instructions that, when executed by the at least one processor, cause the system to:

identify a training embedding pair comprising a molecular structural embedding of a molecule and a phenomic image embedding generated from applying a pre-trained image embedding model to a phenomic image of a cell;

generate, utilizing a contrastive molecular-phenomic embedding model, a first embedding from the phenomic image embedding;

generate, utilizing the contrastive molecular-phenomic embedding model, a second embedding from the molecular structural embedding; and modify parameters of the contrastive molecular-phenomic embedding model by comparing the first embedding and the second embedding.

11. The system of claim 10, wherein the instructions cause the system to generate training embedding pairs for the contrastive molecular-phenomic embedding model by:

identifying an additional molecular structural embedding corresponding to an additional phenomic image embedding; and filtering the additional molecular structural embedding as an inactive molecule by comparing the additional molecular structural embedding to a null distribution of phenomic image embeddings associated to one or more molecular structural embeddings.

12. The system of claim 10, wherein the instructions cause the system to modify the parameters of the contrastive molecular-phenomic embedding model by:

determining a measure of contrastive loss from a similarity distance between the first embedding and the second embedding as a positive pair; and utilizing the measure of contrastive loss to modify the parameters of the contrastive molecular-phenomic embedding model to increase a likelihood of positive pair retrieval from the contrastive molecular-phenomic embedding model.

13. The system of claim 12, wherein the instructions cause the system to determine the measure of contrastive loss by utilizing an inter-sample similarity aware loss that weighs the measure of contrastive loss based on similarity measurements between the phenomic image embedding and additional phenomic image embeddings.

14. The system of claim 10, wherein the instructions cause the system to generate, utilizing the contrastive molecular-phenomic embedding model, the second embedding from the molecular structural embedding and a molecular concentration encoding corresponding to the molecular structural embedding.

15. The system of claim 14, wherein the instructions cause the system to:

determine a first measure of contrastive loss between the first embedding and the second embedding corresponding to the molecular structural embedding with the molecular concentration encoding;

determine a second measure of contrastive loss between a third embedding corresponding to an additional phenomic image embedding and a fourth embedding corresponding to the molecular structural embedding with an additional molecular concentration encoding; and utilize the first measure of contrastive loss and the second measure of contrastive loss to modify the parameters of the contrastive molecular-phenomic embedding model.

16. A non-transitory computer-readable medium storing instructions that, when executed by at least one processor, cause a computing device to:

identify a training embedding pair comprising a molecular structural embedding of a molecule and a phenomic image embedding generated from applying a pre-trained image embedding model to a phenomic image of a cell;

generate, utilizing a contrastive molecular-phenomic embedding model, a first embedding from the phenomic image embedding;

generate, utilizing the contrastive molecular-phenomic embedding model, a second embedding from the molecular structural embedding; and modify parameters of the contrastive molecular-phenomic embedding model by comparing the first embedding and the second embedding.

17. The non-transitory computer-readable medium of claim 16, wherein the instructions cause the computing device to generate training embedding pairs for the contrastive molecular-phenomic embedding model by:

identify an additional molecular structural embedding corresponding to an additional phenomic image embedding; and filter the additional molecular structural embedding as an inactive molecule by comparing the additional molecular structural embedding to a null distribution of phenomic image embeddings associated to one or more molecular structural embeddings.

18. The non-transitory computer-readable medium of claim 16, wherein the instructions cause the computing device to modify the parameters of the contrastive molecular-phenomic embedding model by:

determine a measure of contrastive loss from a similarity distance between the first embedding and the second embedding as a positive pair by utilizing an inter-sample similarity aware loss that weighs the measure of contrastive loss based on similarity measurements between the phenomic image embedding and additional phenomic image embeddings; and utilize the measure of contrastive loss to modify the parameters of the contrastive molecular-phenomic embedding model to increase a likelihood of positive pair retrieval from the contrastive molecular-phenomic embedding model.

19. The non-transitory computer-readable medium of claim 16, wherein the instructions cause the computing device to generate, utilizing the contrastive molecular-phenomic embedding model, the second embedding from the molecular structural embedding and a molecular concentration encoding corresponding to the molecular structural embedding.

20. The non-transitory computer-readable medium of claim 16, wherein the instructions cause the computing device to:

determine a first measure of contrastive loss between the first embedding and the second embedding corresponding to the molecular structural embedding with a molecular concentration encoding;

determine a second measure of contrastive loss between a third embedding corresponding to an additional phenomic image embedding and a fourth embedding corresponding to the molecular structural embedding with an additional molecular concentration encoding; and utilize the first measure of contrastive loss and the second measure of contrastive loss to modify the parameters of the contrastive molecular-phenomic embedding model.

* * * * *